(12) United States Patent
Ryan

(10) Patent No.: US 8,771,956 B2
(45) Date of Patent: *Jul. 8, 2014

(54) MODULATION OF HUMAN MOUSE DOUBLE MINUTE 2 HOMOLOG ACTIVITY

(71) Applicant: Ryogen LLC, Suffern, NY (US)

(72) Inventor: James Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,263

(22) Filed: Nov. 19, 2012

(65) Prior Publication Data

US 2013/0137756 A1 May 30, 2013

Related U.S. Application Data

(60) Division of application No. 13/116,140, filed on May 26, 2011, now Pat. No. 8,313,910, which is a division of application No. 12/795,864, filed on Jun. 8, 2010, now Pat. No. 7,964,357, which is a continuation of application No. 10/608,403, filed on Jun. 27, 2003, now Pat. No. 7,754,424.

(51) Int. Cl.
*C12N 9/48* (2006.01)

(52) U.S. Cl.
USPC ........................................ 435/6.12; 536/23.1

(58) Field of Classification Search
USPC ....................................................... 435/6.12
See application file for complete search history.

(56) References Cited

U.S. PATENT DOCUMENTS

| | | | |
|---|---|---|---|
| 5,411,860 | A | 5/1995 | Vogelstein |
| 6,184,212 | B1 | 2/2001 | Miraglia |
| 7,754,424 | B1 | 7/2010 | Ryan |
| 7,964,357 | B1 | 6/2011 | Ryan |
| 8,058,052 | B1 | 11/2011 | Ryan |
| 8,313,910 | B1 * | 11/2012 | Ryan ............................ 435/6.12 |

OTHER PUBLICATIONS

Andersen et al., 1996, Mammalian Genome 7:780-783.
Bureau et al., 1995, Genomics 28:109-112.
Fang et al., 1999, J Cell Biol 147: 823-830.
Kinzler, 1999, NCBI Locus NM_002392.
Muzny et al., 2003, NCBI Locus ACO25423, gi:14578057.
Oliner et al., 1992, Nature 358:80-83.
Oliner et al., 1999, NCBI Locus NM-002392, gi:4505136.
Rehli et al., 1995, J. Biol. Chem. 270: 15644-15649.
Ries et al., 2000, Cell 103: 321-330.
Sigalas et al., 1996, Nature Med. 9:912-917 cf 2:912-917.
Tan et al., 1989, J. Biol. Chem. 264: 13165-13170.
Watson et al., 1992, "Recombinant DNA" 2nd Ed. Scientific American, New York. pp. 137-138.
Zauberman, 1995, Nucleic Acids Res 23: 2584-2592.
Non-Final Rejection dated Dec. 1, 2004 for U.S. Appl. No. 10/608,463, filed Jun. 27, 2003.
Final Rejection dated May 25, 2005 for U.S. Appl. No. 10/608,463, filed Jun. 27, 2003.
Non-Final Rejection dated Mar. 8, 2006 for U.S. Appl. No. 10/608,463, filed Jun. 27, 2003.
Final Rejection dated Aug. 25, 2006 for U.S. Appl. No. 10/608,463, filed Jun. 27, 2003.
Final Rejection dated Apr. 16, 2009 for U.S. Appl. No. 10/608,463, filed Jun. 27, 2003.
Non-Final Rejection dated May 14, 2008 for U.S. Appl. No. 10/608,463, filed Jun. 27, 2003.
Final Rejection dated Jan. 2, 2009 for U.S. Appl. No. 10/608,463, filed Jun. 27, 2003.
Notice of Allowance dated Feb. 23, 2010 for U.S. Appl. No. 10/608,463, filed Jun. 27, 2003.
Amendment After Allowance dated May 16, 2010 for U.S. Appl. No. 10/608,463, filed Jun. 27, 2003.
Notice of Allowance, dated Feb. 11, 2011 for U.S. Appl. No. 12/795,864, filed Jun. 8, 2010.
Notice of Allowance, dated Jul. 6, 2011 for U.S. Appl. No. 12/795,909, filed Jun. 8, 2010.
Non-Final Rejection, dated Feb. 1, 2012 for U.S. Appl. No. 13/116,140, filed May 26, 2011.
Notice of Allowance, dated Jun. 19, 2012 for U.S. Appl. No. 13/116,140, filed May 26, 2011.
Notice of Allowance, dated Aug. 23, 2012 for U.S. Appl. No. 13/244,474, filed Sep. 24, 2011.

* cited by examiner

*Primary Examiner* — Tekchand Saidha
(74) *Attorney, Agent, or Firm* — Cheryl H. Agris; Agris & Von Natzmer, LLP

(57) ABSTRACT

The invention is directed to isolated genomic polynucleotide fragments that encode human carboxypeptidase M and human mouse double minute 2 homolog, vectors and hosts containing these fragments and fragments hybridizing to non-coding regions as well as antisense oligonucleotides to these fragments. The invention is further directed to methods of using these fragments to obtain human carboxypeptidase M and human mouse double minute 2 homolog and to diagnose, treat, prevent and/or ameliorate a pathological disorder.

2 Claims, No Drawings

SEQUENCE LISTING

<160> NUMBER OF SEQ ID NOS: 4

<210> SEQ ID NO 1
<211> LENGTH: 443
<212> TYPE: PRT
<213> ORGANISM: Homo sapiens

<400> SEQUENCE: 1

| Met | Asp | Phe | Pro | Cys | Leu | Trp | Leu | Gly | Leu | Leu | Pro | Leu | Val | Ala |
| 1   |     |     |     | 5   |     |     |     |     | 10  |     |     |     |     | 15  |

| Ala | Leu | Asp | Phe | Asn | Tyr | His | Arg | Gln | Glu | Gly | Met | Glu | Ala | Phe | Leu |
|     |     |     | 20  |     |     |     |     | 25  |     |     |     |     | 30  |     |     |

| Lys | Thr | Val | Ala | Gln | Asn | Tyr | Ser | Ser | Val | Thr | His | Leu | His | Ser | Ile |
|     |     |     | 35  |     |     |     |     | 40  |     |     |     |     | 45  |     |     |

| Gly | Lys | Ser | Val | Lys | Gly | Arg | Asn | Leu | Trp | Val | Leu | Val | Gly | Arg |
|     | 50  |     |     |     |     | 55  |     |     |     |     | 60  |     |     |     |

| Phe | Pro | Lys | Glu | His | Arg | Ile | Gly | Ile | Pro | Glu | Phe | Lys | Tyr | Val | Ala |
| 65  |     |     |     |     | 70  |     |     |     |     | 75  |     |     |     |     | 80  |

| Asn | Met | His | Gly | Asp | Glu | Thr | Val | Gly | Arg | Glu | Leu | Leu | Leu | His | Leu |
|     |     |     |     | 85  |     |     |     |     | 90  |     |     |     |     | 95  |     |

| Ile | Asp | Tyr | Leu | Val | Thr | Ser | Asp | Gly | Lys | Asp | Pro | Glu | Ile | Thr | Asn |
|     |     |     | 100 |     |     |     |     | 105 |     |     |     |     | 110 |     |     |

| Leu | Ile | Asn | Ser | Thr | Arg | Ile | His | Ile | Met | Pro | Ser | Met | Asn | Pro | Asp |
|     |     |     | 115 |     |     |     |     | 120 |     |     |     |     | 125 |     |     |

| Gly | Phe | Glu | Ala | Val | Lys | Lys | Pro | Asp | Cys | Tyr | Tyr | Ser | Ile | Gly | Arg |
|     | 130 |     |     |     |     | 135 |     |     |     |     | 140 |     |     |     |     |

| Glu | Asn | Tyr | Asn | Gln | Tyr | Asp | Leu | Asn | Arg | Asn | Phe | Pro | Asp | Ala | Phe |
| 145 |     |     |     |     | 150 |     |     |     |     | 155 |     |     |     |     | 160 |

| Glu | Tyr | Asn | Asn | Val | Ser | Arg | Gln | Pro | Glu | Thr | Val | Ala | Val | Met | Lys |
|     |     |     |     | 165 |     |     |     |     | 170 |     |     |     |     | 175 |     |

| Trp | Leu | Lys | Thr | Glu | Thr | Phe | Val | Leu | Ser | Ala | Asn | Leu | His | Gly | Gly |
|     |     |     | 180 |     |     |     |     | 185 |     |     |     |     | 190 |     |     |

| Ala | Leu | Val | Ala | Ser | Tyr | Pro | Phe | Asp | Asn | Gly | Val | Gln | Ala | Thr | Gly |
|     |     | 195 |     |     |     |     | 200 |     |     |     |     | 205 |     |     |     |

| Ala | Leu | Tyr | Ser | Arg | Ser | Leu | Thr | Pro | Asp | Asp | Val | Phe | Gln | Tyr |
|     | 210 |     |     |     |     | 215 |     |     |     |     | 220 |     |     |     |

| Leu | Ala | His | Thr | Tyr | Ala | Ser | Arg | Asn | Pro | Asn | Met | Lys | Lys | Gly | Asp |
| 225 |     |     |     |     | 230 |     |     |     |     | 235 |     |     |     |     | 240 |

| Glu | Cys | Lys | Asn | Lys | Met | Asn | Phe | Pro | Asn | Gly | Val | Thr | Asn | Gly | Tyr |
|     |     |     |     | 245 |     |     |     |     | 250 |     |     |     |     | 255 |     |

| Ser | Trp | Tyr | Pro | Leu | Gln | Gly | Gly | Met | Gln | Asp | Tyr | Asn | Tyr | Ile | Trp |
|     |     |     | 260 |     |     |     |     | 265 |     |     |     |     | 270 |     |     |

| Ala | Gln | Cys | Phe | Glu | Ile | Thr | Leu | Glu | Leu | Ser | Cys | Cys | Lys | Tyr | Pro |
|     |     | 275 |     |     |     |     | 280 |     |     |     |     | 285 |     |     |     |

| Arg | Glu | Glu | Lys | Leu | Pro | Ser | Phe | Trp | Asn | Asn | Asn | Lys | Ala | Ser | Leu |
|     | 290 |     |     |     |     | 295 |     |     |     |     | 300 |     |     |     |     |

| Ile | Glu | Tyr | Ile | Lys | Gln | Val | His | Leu | Gly | Val | Lys | Gly | Gln | Val | Phe |
| 305 |     |     |     |     | 310 |     |     |     |     | 315 |     |     |     |     | 320 |

| Asp | Gln | Asn | Gly | Asn | Pro | Leu | Pro | Asn | Val | Ile | Val | Glu | Val | Gln | Asp |
|     |     |     |     | 325 |     |     |     |     | 330 |     |     |     |     | 335 |     |

| Arg | Lys | His | Ile | Cys | Pro | Tyr | Arg | Thr | Asn | Lys | Tyr | Gly | Glu | Tyr | Tyr |
|     |     |     | 340 |     |     |     |     | 345 |     |     |     |     | 350 |     |     |

| Leu | Leu | Leu | Leu | Pro | Gly | Ser | Tyr | Ile | Ile | Asn | Val | Thr | Val | Pro | Gly |
|     |     |     | 355 |     |     |     |     | 360 |     |     |     |     | 365 |     |     |

His Asp Pro His Ile Thr Lys Val Ile Ile Pro Glu Lys Ser Gln Asn
370                 375                 380

Phe Ser Ala Leu Lys Lys Asp Ile Leu Leu Pro Phe Gln Gly Gln Leu
385                 390                 395                 400

Asp Ser Ile Pro Val Ser Asn Pro Ser Cys Pro Met Ile Pro Leu Tyr
            405                 410                 415

Arg Asn Leu Pro Asp His Ser Ala Ala Thr Lys Pro Ser Leu Phe Leu
            420                 425                 430

Phe Leu Val Ser Leu Leu His Ile Phe Phe Lys
            435                 440

<210> SEQ ID NO 2
<211> LENGTH: 491
<212> TYPE: PRT
<213> ORGANISM: Homo sapiens

<400> SEQUENCE: 2

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
                20                  25                  30

Leu Leu Leu Lys Leu Leu Lys Ser Val Gly Ala Gln Lys Asp Thr Tyr
            35                  40                  45

Thr Met Lys Glu Val Leu Phe Tyr Leu Gly Gln Tyr Ile Met Thr Lys
50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
            115                 120                 125

Leu Glu Gly Gly Ser Asp Gln Lys Asp Leu Val Gln Glu Leu Gln Glu
130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
195                 200                 205

Arg Ser Ser Ser Ser Glu Ser Thr Gly Thr Pro Ser Asn Pro Asp Leu
210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
            275                 280                 285

Asp Ser Phe Glu Glu Asp Pro Glu Ile Ser Leu Ala Asp Tyr Trp Lys
290                 295                 300

```
Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
            325                 330                 335

Asp Lys Gly Glu Ile Ser Glu Lys Ala Lys Leu Glu Asn Ser Thr Gln
        340                 345                 350

Ala Glu Glu Gly Phe Asp Val Pro Asp Cys Lys Lys Thr Ile Val Asn
    355                 360                 365

Asp Ser Arg Glu Ser Cys Val Glu Glu Asn Asp Asp Lys Ile Thr Gln
370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
            405                 410                 415

Glu Glu Thr Gln Asp Lys Glu Glu Ser Val Glu Ser Ser Leu Pro Leu
        420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
            485                 490

<210> SEQ ID NO 3
<211> LENGTH: 99680
<212> TYPE: DNA
<213> ORGANISM: Homo sapiens

<400> SEQUENCE: 3
taattacaac tttaaacacc aaaccacagt catgttggca ctcagaattt gaatccttat     60
ctactgggct ccagaatctg tacttttttaa tttatttact tatttctgag acagggtttt   120
gctccgttgc ttagactaaa gtgctgtggt acaatcacgg cttactgcag ccttgacctc    180
ccgggctcaa gcgatcctct tgcctcagcc ccctgagtag ctgggaccac aggtgtgtgc    240
caccatgccc aactaatttt tgtatttttt gtacagatga gctttcgcca tgttggctag    300
gctggtattg aacttctaga ctcaagtgat ccacccacct cagcctccca aagtgctagg    360
attacaggtg tgagcccaga atctgtactt ctaacaacaa aatagtttc taatacatac     420 aaaatacttg ataggcctga tggaggataa aggaattaat aaagtatatt ttgtgtcctc    480
cgggagctta ccatttagtg gaggaaatat gtattcccac aaataactgt ggggcaccaa    540
gttatgagta cttttacctc cactccaatc tgccactggc tactgagcaa tggtccaagg    600
ttagagcatc atatttagcc atagtataca ttggcatgct tactggggttg tgtggcagca    660 ataaatggca actgaaccaa agatgcagg agtctagcaa gacttttttac ttctggagca   720 atttcaggct tccaaatcct tactgaatta cccttaattg caatttctcg tattactgag    780
atgatgagag tctaatcatt gagactattt cctcctaact ttgttgctat atgcaggcaa    840
ccaagcttca ttctgactgg gggttacgct aacttggatt ttaaaaccca attctgcagt    900
tcaagagaga tgataaatgg agtagaggga cctcctccct accctccccc caaaccccc    960 aaagccttcc caactcccta tatactctaa aagacagaca ctagaaacta acaacacat   1020
```

```
aatctgatgg gctgatcaat aatgcattgg ttttattacc tgaatatttt ggggttactt      1080
tttcatgtca gtctctcatg tcaaaaattc tcatttccct aatgcctacc ccctcaggcc      1140
ctcatctctc ttccatcttc ctcacgaatg ataatttaag gtcataaaac agatagcttc      1200
acactttcaa tataaactcc aaaaaataaa ttgttagcgg tatttatctg accectatat      1260 tctagctatt atagtcagat aataaaatcc agggtgctcg agggaacaga tcaaggggac      1320
agttagaaaa cttaagcttc agtgtttctg ttgactctag aaaggcaaaa ctaaaataac      1380
tcatctgtag cctgaatatc attcccaata ggagttagat aaaagcctat cttggcaaag      1440
ctcaaagtcc ttaaagtttg ggtcttattt gtttgtttgt tagactatttt tggatcttga     1500 gagtttgctt tgggatgggg aacagctatt agagctgttt ggcgagtggg tatgctagaa      1560
atgggttgaa attatgacat tagtataaat ttttataaaa atctaatttc tagactgggc      1620
aacatagcaa gaccttgtct ctactaaaat aaaaaaaaat tttaaaaaag ctggccatgg      1680
tggcacacac ctgtagtccc agctacttcg ggggctgagg cagtaggagc ccttaagcct      1740
gggaagtcaa ggttgcagtc agccctgatt gtgcaactgc attccagcct gggcaacaga     1800
acaagaccct gtctcaaaaa aaataataat aaataaaatt agtcattata taaaaattct      1860
ttcttttctt ttttttttttt tgagacagag tcttactctg ttgcccaggc tggagtgcaa    1920
tggcgcgatc tcagctcact gcaagctccg cctcccaggt tcaagtgatt cttctgcctc     1980
agcctcctga gtagctggga ttacaggtgc atgccaccat gcctggctat ttttcatatt     2040
tttagtagag atatggtttt gccatgttgg ccaggctggt cttgaactcc tgatttcagg     2100
tgatctatgt gtcttggcct cccaaagtgc tgggattaca ggcatgagcc attgcacccg     2160
gcctcaaaat tatttctaat gtgtgcaaag atatctgata aaaactacat gactatgtaa     2220
aataaaacat actatttcct ctgcctggac tttctatttc ttcacccttc aagttacagc     2280
ttaaacagat ccatcttctg gaagcttttt tgaactccac ttaactccat ttcaactcaa     2340
tgagcacctt ctgtgctctt gaatgcaggt ttctgatgac tttggaggtt gtgccactgg    2400
aatagaggga aaaaacttct aggactttca tggagagctt atgtgttcat gaatattgag     2460
cagaacagga gttattgca tggactgagc aaacagaaga ccaaaataat cttttttatga     2520 tttttttgctt aaaacgttgc ttattctttg tgtttttcag agtcaagaaa acttttttat    2580
ttggagctat ttcagctttt taacaactga gtaaaataca ctccagtgag caaatttttgg   2640 agcgcatttc tttctctcta ccttatttct ctgtaatttg gaaactatgt ctacgtatac     2700
ttaatttatg gtagtatcgc tatttgcata agttcagtaa gcatctgttt tcttttgtaa     2760
caggacacta ttagagacac tagttatttt accaaggctt tgactggaat gacatgtttt    2820
cagacttttc agactgcttt gaggaattga ggttgagcta cagagctgat aaaaattcct    2880
tggaaaaact ggccaccttg ttttttacaag gttcccaacc tgtggtaagt aaaaatgtcc    2940
ctttctgata ggcctaggaa tcccaagtta tttttggtacc tctagaaatg aggaattcat    3000
tcaattcata caggtatctg caggcacaaa taaatctttg gctgggctca agatgctttt    3060
aaaaggtcta atctgagatt ccttattaaa aaaacatcca gcaaagccaa ttttttaaaa    3120
aggcctatat agcaaataat tattcatgtt atgttttcatg caaacaatta ggcctagtat    3180
aaataaaacc aaagcttatt ttgcaaataa attggtcctg ctatgatttg tctttggtaa    3240 aaatgggggga aaactggaga gggaaaaatt atgtttcaaa aaaaacctat agcatgcctg    3300
ttattagatt ctagccttgg ctgggcacag tggctcacac ctgtaatccc aacattttga    3360
gaggccgagg caggaggatg aatcacttga gcccagaagt tcgagaccag cctgggcaac    3420
```

```
ataggggagac cccatctcta caaaaaatta tttaaaaatt agctgggtgt ggtggtgcac   3480
acctgtagtc ccagctactt ggaaggctga gatggcagga tcactttagc cctagaggtc   3540
gaggcttcag tgagctctga tcatgccact gcactccagc ctgggcaaca gagtgagaca   3600
ctgtctcaaa aaaaaaaaa aaaaaaaaa agaaagaaag aaaagaaaag aaaaaaattc   3660
tagccttgtc cattgtttgt gagcctatac taatgactca catctgattg gttcttgggg   3720
atatttacct gaatccctca aggcttcaga tcagttctgc aaggactcct gaagctaaga   3780
ctttcacacc ttgcattagg tctcttgtag tttactgttc tcttaagtgc tatactaacg   3840
atgtggataa gaatactaac gttttgtta taccaacatt ggggacccaa caaggcacct   3900
gggaatacat acagacaact gcaaaatggt ttcactcctc ttaccttggg ggcaacccctt  3960 gccccaacta taccccctgt caacaggaag agcagttgtc agccttttcc catctcccca   4020
gctcacacct caggattgag gtgtgctgaa gcacaaggga gggaactgaa accacctttg   4080
caaagattat gacagcaaga aaagtctaac ttgactgact ccatcttgct tctagtctca   4140
caggctggct gtctttgcta attcctgggg gcacaaagag ctaaccatgg gagggattta   4200
gtttatagtt tcacttggaa gcaaggatga taacagtccc tccctaaaac taatctcctc   4260
cttgcttaga gagtgaaaac taatgaaagg ccacaagatt agggttattg gagggacctg   4320
aattctgcta aagtataggt atacttttat aatcccttac tgctcaggag tcatgtggcc   4380
agaggtcaca agatttgtga cttccccaat tgctcttata gataacatca ctactgtaga   4440
acttaagatt ggtctcttga gatgttttc agattttgt attctggcca tcaactgatc   4500
ctacctggac tcatgactca tgactcaact ggtcctgtgg cccccaccca gaggcagact   4560
cagctcactg ggacagtttt ccacacccct atgatttttt tcccaactaa tcagcagtac   4620
ccattaccta gtccccgccc accaaactat ctttaaaaat cctaacgtct gagttctcag   4680
aaagactgat ttgagtggta actccagtct ttctgctctg ctgccttgtc acttctttat   4740
tgtaatttaa aaaaaaaaaa caaaaacaa ggtgaaggag ccaggcatgg tgtctcatgc   4800
ctatcattcc tgtattttgg gaggctgagc tgggcggatg acttgaagcc aagagtttga   4860
gaccatcctg tgcaacgaag tgaggcccca tatctacaaa aataaaatta tctgggtgtt   4920
gtggcatgtg tctgtagtcc caactgctca gaaggctgag atgggaggat tgcttaagcc   4980
cagaagttca aggcttcagt gagctatgat tataccactg cactccagcc tgggcaacag   5040
agcaagaaac tgtctaaaaa gaaaaaagt aagtacgttc tgatagtatg tctcataata   5100
tcctgtaatt ttctttctgt aataggcatc aaaatggcaa ctgagtgact gcttatctct   5160
gtatcatctt tcccaataca atatgaactc tatcaaagtg aggactatgt ttctcttta   5220 caccatggta ttcatagtgc ttagcatatt attagatgtt cattaaataa ttatcaacag   5280
aaggaatgaa tgaaccaatt aatcatgagt catgaggaga caaaagaatt tgtttggcta   5340
ttgtctgagt atatttataa tttgactttc cagaggtcat tgttgaatag atatgatgta   5400
tgctgttttc aaaagggtca ttgaaaagta aatgattaga tgaacttaca aattattaac   5460
tatcttcaaa cagtctcttt gtcactctgc tatatataca tttttccctt cttcccacac   5520 tcccccctgcc tttctttctg ctacaggtac agggtattaa caaagatggc agattctttc   5580
tcaaatatac agttttaaa aaaaaaaaaa tccagaaatg gttttctcga catttgaaac   5640
aaagctagaa aagaaataaa tttcagtaag tatattgttt cctaagagac aagagtatga   5700
ctttcatctg ctgttatgtc agattgtttg atatcacaca atccagatta aatgcagcta   5760
```

```
aataggactg tctttgcttt ggaaatcggc cttattagag ccaagaagct ttcttgcaaa    5820
tctataatat aaacaaagta tagtaggaga agtaagcatt attttgcact caaagaccat    5880
gagtttaaga gaaaaagtca ctattgtaac aattgctttg taattgtaaa ttatcacaaa    5940
tttatggttg ataaaggtct attccactat tgcaaatatg ttggaaggag ctgggatgtg    6000
gaaataaata agataaatat aaacatatac tatctgttgt atcccttcct gtcttgttca    6060
tcttcactag atggtaataa taataaaaat gaattcagct tgggacttat aaagcattta    6120
taacaggcca gacactgttt gttctaaact ctttgtatat gttaactcat ttaatatatg    6180
caaccctgta aggtcactat aatcctctaa gatcaatacc atgagttagc ccagtttaca    6240
gaaaaggaca tgaatgcacc aagaggtgca gtgacttgct cagggcacac agtaagcgac    6300
agagctgggg tttaagctaa gatggtgtgg ttccacagac cttactttta ataatttact    6360
attttagtta ttacatataa tctcttgatg ctatattctt cctagaataa cacttataaa    6420
tcagcaagca tgcactgagc tctgacctag atgccatggg ggaaacaaaa aatgacacca    6480
tttgatgctt cactcactct atttggggtg tcttcctgaa ctgaaattaa tttcaaacgt    6540
ttagattttt cctgacattg tttctcagct gatgtgttag ggcatactgg agtgtcaaac    6600
tttgatctga ttacatttta attttgcttc accaacagta gatagaatgt gaagctaaga    6660
aggtcatgct gtgcagtaca gaatgtggta caaaccacta ggggataaga cacaagaagc    6720
agaaagtaat attatgccag ctcccccaaga aagatcacag gtttctttga acatgtgaaa    6780
ttctttagtg gagatttttg gctcttgtag aatgtaagct acctaagggc agagatttgt    6840
tctgtcttgt ttacagtcgt attccctagg agcaagtgca gtgcctgaca cagagtaaac    6900
aataaataat tgataaggaa atgaatgaat aattaaaaat cagagagtgg ggcaaagcag    6960
aaataggttt actctcacag tgacatagtg ccaacaaggg acaatagtgt gataacggtg    7020
catgatttta tagtcattgc tgtgtatttt tatattcttc ctatggtacg cttttgatt    7080 atgtagatag cattttttta gtccttttct ttctttgtgc catgaaaaat tctaggattc    7140
agaaatttat cacgaacaca aatgtgtata caaatccttt ctaaatctct caaaggaata    7200
ctaatgcatt tacagttgca catccaaaat aaaagaacta ctctgtttgg ttttgatag    7260 acaacttgca taacaaacag aaaacacagc cacaatttct agagaaatgc ttattaaaaa    7320
gacatacagt tctaaaaaac aaagtctact aataaaaaaa taaggaaca attttaaaa    7380 gatgcacagc caagactaca gagtccttgt tttaaacaga gaatgcttga gttgagacat    7440 attcttttcaa tctctgagtc ccactgttta gacatcaccc gtggtagttt agggaaagga    7500
tcatcttgga ccttaacaaa aaccatccag ctttttcacta acaattttct tatctctagc    7560
tataaatagc aatctttcct ttctgaagaa ttgcaaggtc actttccttt tttatcaaaa    7620
acaaacaaat ccggttttgc tggggggtact gatctgagtt gggggagcta ctttgaagga    7680
ggtaggttta gtactggggg aggtaccagg agatcccagc ttaagataaa tgcccaaact    7740
ccctcagata catgagaagc agcagacaat agaaagaatc attgagcagc attagtataa    7800
ggcattatat tctacttgtg aaatttcaag aaaatgtgtc tttaaggcct aggcaggcag    7860
atcacttgag gccagaagtt cgagaccagc ctgggcaaca tggtgagact ctgtatctac    7920
aaaaaataca caaaaaaata gccatgcgtg gtggtacaca cctgtagtcc cagctacccg    7980
ggaggctcag gtggggaggat tacttaagcc tgggaggtta aggctacagt gagctgtgat    8040
cacgtcactg cactccagcc tgggcaacag agccagaccc tgtctcaaaa acaaacaaac    8100
aaacaaaaaa caaataatg taaaataagt tttaccttat tgggcgagtt atttctgagc    8160
```

```
gaccatttga tgcttcactc acactatttg gggtgacttc ctgaactgaa attaatttca    8220
aatgtttaga ttttcctga cattgttct cagctgatgt gttagcttta tatacacaca     8280
cacacacaca cacacacaca cacacacgta ctcagcacat cttcaaatta cttctgtagc   8340
acaaaaacac acaaattgac caatggaaca gaaataagcc agtcacaaaa agacaaatat   8400
tgcatgattc cacttatatt aggaatctaa actagtcaga cttttagaaa gaatgttggt   8460
agccaggagc aggagagaga gagaaaaggt gggttgttgt tcagtgggta tagagtttca   8520
gttttgcaag gtttgaaaaa gttctagagc tctattgcac aacagtgtgc atagagttaa   8580
cacaactgca ctgtacactt agaaacagtt aagatggtaa ttttatatgt tttatagcac   8640
aataatttaa aaaatatagg aaggacatgg tctcagaata aagggccatc ttttatcata   8700
aagaaaaatt tgcaacccaa ttccaacatg ttaaggtgtt ctcttcttgt tgtttcattg   8760
agaactgcta aaagtctcag tgcccttctc atttggatgg tggtcctact caaacgtttg   8820
gagaccaaag ccccatttgg taataagaag gatgtgttgc ctggcctggt gctctgggca   8880
tatacacttc aggagaacct ttcgtaggta ggggttaagg attggaatct gtcctgacag   8940
aacaatgtct tcacacaatt aacacatagt tcacatacta gatgaaaaca aattccaagt   9000
ggactacaaa tataaatctg ggggagggag agagggatga ataggtggag cacaggggat   9060
cactagggcc atgaaattat tctgtatgat actgtaatgt tggatacatg ccattataca   9120
tttgtaaaaa ctcatagcat atgcaatata aactatagat ttagttaata ataatgtgtc   9180
aatattggct catcaatttt aacagatgtg acacgctaac gccaagatgt taataataag   9240
ggaaactgtg tatgtgggta gggcaggaaa agggtatatg ggaaccctat actttctgtt   9300 caattttct gcaaatctca aactgctcta aaaaaattaa ttttaaaaaa tgagatgaaa    9360
gaagaaaaat gaaaaaataa aaataccaaa gaaataaaaa tagaagaaaa tataaattaa   9420
tttataattt aagaataaac tttctaagaa tatatcaaaa aactatgaat ccagaaggaa   9480
aagactaata cacaaccaga aaaatgagca aaagctatta atagactatt ttttaaaaga   9540
agaacaataa atgttcaata agactatgag agaaatgttc agtcacatta atactaaaac   9600
ttaaaattat gagatttcat ttttatctat gaaattggca aacattttta aaagagataa   9660
tagtaatcat gaggagccaa acaggcattt tcacatatca ccagtgagga ctgtaaattg   9720
gaatgacctt tggtcagaaa aaatttttca aaacttggaa agcaaaatat gattgcataa   9780
tttgttttca tgttaggcat tgcctaacca gtccatctaa ggtgaattga atcctgactc   9840
gttattacag atttgcacat tttacaactg taaattcaaa tgttagtttg tagaaaattg   9900
gtgagatgct atatttttgt ccaatggaga tataatttct gtcctgcaca gatgaaaata   9960
attttgctct gtaaagatag caccaaacat tatggtttat caccctgtaa gacattaatc  10020
agatttatat ctaatttagc aataatgtag aatgatttta gtattctttt ttatatattt  10080
atgtatatat ataggatgta tatttacata tgtatattat atatagtatg tatatacata  10140
atataaatac aatatgtata taggtatgtg tacacataat acatatacta tatgtatata  10200
tgtacataat atacataagt atatacatca tatacatata tgatgtctat atgtatagac  10260
atcatataca ttatgggatg tacatacata tatacataac atatacatat attatgtata  10320
tattattata gatatatgta catatataca tacatatatg tatgtagtaa atgtatatat  10380
agatacatat gtgtatacat atatagatgt atgtacatat atctatgtat atacttatag  10440
atgtatgtac ataatatcta tatatatact tacagatata tttatataat atctatatac  10500
```

```
ttacatatat gtactatgta tatttagata tatacacata tttatacata tatgcatata    10560
cacatataca tatatatgta tgtacatata taaatagata tacataatat atgtatatac    10620
acatatagat atatatgtac acatatagat atacgtgtgt gtgtgtgtgt atacacacat    10680
attttctcat gtctttcttt gaactggctt tgttatcctg ctggtttcct cattaataag    10740
ttaaaattaa aacttgaact gtgcttactc tatatttgta tgagaatact ttttaacatt    10800
ttttaaatta tacatttgac attttatagg agtataactt ggccaaatat tttaagtctt    10860
aaaagtgtac atgcttttta acctagcaat tacatgtcta agaaatgatc ctaaggaggt    10920
aaggacatgc tcaaaggttt agctctgaga atgtttctag atgtgctgtg tataataaag    10980
aaataccaga aacaaatgtg ccacattagg gcgctggtta atacctaaat gtgtgtgtgt    11040
ttgtttgatt gttttggggt ttggggattt ttttttttta agacagagtc tcattctgtc    11100
acccagaatg gagtgccatg cgatcatggc tcactgcaac ctcaaacccc tggggtcaag    11160
caatcctcct gccccagcct cctcagtagc tgggactacc ttgccccatc cctaaatgtg    11220
ttttaagaat ggttgtttcc aggtaagtaa aatttgtaag tttaaatttt tcttttatc     11280 ttgttcagat tttcttgtga cactttcaaa gaaaaagtt tgaaagtcac aaagtctagt     11340
tatactgttc tcattcttgt tgacatctat tgaggtactt agccccgact atagttattc    11400
cctctgtccc aattcctgct actatcttag ggaaattcag agtccttaaa cagaaccaat    11460
ccaacactct ggctttttca ttccttaatt tcccatttcc agtgatcttt acctcctctt    11520
cacttttgta attcactcta agatattttg atcctgtttt cattcagaat tagtcattgg    11580
tcctctctaa cactttgtg cttttcctc tgctttgctt ttaaattaaa atgccttcat      11640
tgttttccca atttaaaaaa gcaatgcatg tttggtggaa aaacttttca gaaaatacag    11700
aaagatgtaa aaaagaaaat taaaacattg caactcgtgg atttgcactc agcatgttgg    11760
taaccttaga aacacattgc tgggaatagt ttttttttgt ttgctttatc taaatgagat    11820
cttactattt attttacttt tattatctgc ttccttgcctg aacaatttgt ctttccaagt   11880
gaataaatgc agatctacat tgacattatt atggctgaaa acaattaat tgtacagcta     11940 taatattctt taacccaggg tgtcttaact tcagcactat tgacattttg ggctgaataa    12000
ttctttgttg tgggaggctg tgttgtgcac tgaaggatat ttaatgcctc cctgccctct    12060
gtatcagcac tagatgccag tagctcccat ccctagttat gacaatcaaa aatgtctcaa    12120
gatattgcca aatgtctgct gtgggcacta ctgcctcaag ttgagaacca ctgatctaac    12180
caatctgctg ttgtttgaca tttaggtttt atctactttg tcacaattta aagcagcagc    12240
acttatgaag ctcctaacat atacaaactc aacacatctt caaattactt ctatagcata    12300
aatttctagc aaggaatggc acatacaaaa ttttgatgtc tattcccaga tttccctcca    12360
gaaagattgt attaatttag aacaccattg aaacagcata aatgtcattt cctgagatcc    12420
tgtctacttc caggtattgt caatcttttt aatcttgctt tgtgataagc aaaacaaagt    12480
attactttac ccttttaact tgtaattctt tgattgctta ccaggttggt aacctttact    12540
atatttatta gctatttgtg ttactgcttt tatgaactgc ttattcatct cctttgctca    12600
ttctttattt tgtaagagca ttaattcctt cttccagctt gtaattttc tcataacctg     12660 atttaaacct ttcttcttat aacctttata aggttttctg tacagaagtc atacatttgt    12720
atgttttcaa attattagcc ttttattat ggttttacct ttaatggtgc catacttaga     12780
aagatcacct ctaggtccag gcctggtggc tcacacctgt aatcccagca ctctgggagg    12840
ctgaggcagg cagataattt gaggccagga gttcgagacc atcctggcca acgtggtgaa    12900
```

```
acccegtctc tactaaaaat acaaaaatta gccaggcgtg gtggtgggca cctgtaatcc  12960
cagctactca ggaggctgag gaaggagaat tgcttgaacc cgggaggtgg aggttgcagt  13020
gagctaaaat tgtgccactg cactccagcc tgggcaacag agcaagactc tatctcaaaa  13080
aaaaagaaga aagaaagaag atcacctcta aatctctaa acttcagtat tttactctat   13140
taggctaacc ttttatttg ctgttatctt tcatactctt aacactaaat ttttttttct   13200
ctcttgacca gtgcaccta aacttgaatg tacatataca tcatctggaa atcttattaa   13260
aatgtgtgtt ctgattcagt aggtttggag tggagtgaca gattctacat ttccaacaag  13320
ctcccaggtg atgccagtgc tgtccctggc ctgcactctg agttactagc tcctaaacct  13380
tcagcactca gtcctctgta cccctacct ccattctctg actccttcct gaagttgcct   13440
cccttcctac ctagtgtgaa ccccaatggc agcaatttca actatagctc atctctgttt  13500
ttccagaaca acaatcctgg caatctccat tccagtattg atgaagccac catttcttcc  13560
agtctccagc cacagcaccc tgcaggaaat cagatagtgt ccacgtactt ctcttaaaaa  13620
gataggattt ctaaggtaca tcagcaagcc ttcacttgt tcccacccag ttcccttcc    13680
cattcctaga gtaactttgc ctaaatttaa tcttctcaag ctccagtccc cctcctcaga  13740
cctcttagtc aatgaacaac aatgaaaggg aaacgtcttc aacccttcca gtggaaataa  13800
catttagcat agtgactact gcacaattaa aaaaaaaaa acctactcaa agactctaca   13860
atgtcatact aagacttcca actcttaggc caggcaaggt ggctcactca tgtaatccca  13920
gcactttggg aggctgaggc agaaggatca cttgaggcca ggagttcaag actagcctgg  13980
ccaacatggt gaaacctggt ctctattaaa aatgcagaag ttaggcatgt gtggtgtaaa  14040
aatacaaaag ttacgtaggt gtggcgatgc gtgcctgtaa tcccaggtac gttagaggct  14100
gaaacacaag aatcgcttga acctggaagg cagaggctgc agtgagctga gattgcacca  14160
ctgcactcaa gcctgggcaa cagagtgaga ctgtatctca aaacaaacaa acaaacaaac  14220
aaacaaacaa acaataaaac aacttctctt taagaaaaaa aaaagatgg ccaggcacgg   14280
tggctcacgc ctgtaatccc agcgatctgg gaggccgagg caggcagatc gcccgaggtc  14340
gggagttcca gaccagcctg gccaacatgg tgaaaccccg tctctactaa aaatacaaaa  14400
attagccggg cctggtggca ggtgcctgta atccgagcta ctcggtaggc tgaggcagga  14460
gaattgcttg aacctgagag gaggttgcag tgagccgaga tcatgccatt gcactccaga  14520
ctgggcaaca gaattgagac tccatctcaa aaaataaaga aagaaataaa aaattaaaaa  14580
aaaaattcca actcttggaa aattcccttt aaagagttac gaattaagct ggtttattta  14640
tgtaataaac gcttcgcaca gttcttacaa tgtgcctgcc aaccttattt aggtaggtac  14700
aattaagact tccactttac acaccagaaa ataaggcaca gagtcgacac agccactgag  14760
tgtcagagca agaattggca ctcatcccgt gagcgcctca gttctttttt tttctttata  14820
tatactttaa gttctagggc acatgtgcac aactgtggca catatacacc acggaatact  14880
atgcagccat aaaaaaggat gagttcatgt cctttgtacg acatggatg aagctggaaa   14940
ccatcattct cagcaaacta tcgcaagggc agagcgcctc agttcttaaa ccactcttct  15000
atgctgcggc agaatcactg gaagtctcag ggagtcctga gtgcgcaatt ctaggaaaag  15060
tatctatatc tgtaagaaag aaggggcagg gaatctaacg gttctcagct cttgaaggca  15120
cattagattc attcaaggtc ctctctaaaa atacactttc ttgggcctcc acgagaaaaa  15180
ttctattcaa ttagtcgtgg gcttgcatcc gtatttttag tctgtaaaag tggaatgtta  15240
```

```
tctcaaatca gtggttttca aacttttat attctgcgga ccttgacacg ggcccccaat    15300
accctgacac ggttacttac aatccgggag agagtgggag aaaggggag agagggaagg    15360 ggagagggg aggggagaga gagagaatga atgagaatga atcttttaga gaggtagagg    15420
gggttggccc gtgccacaaa ccacctctca ggtttgagtg aagccttcgt tctctctcgt    15480
gcagagacca tgccatcctt ccagaaagga gcattttagg acgttttagg acgagagacc    15540
tgtaattggc ctaagactca ggtgcaggtg gaggaagcat cggatttaca acagtggtcc    15600
tgccttcttc gatgtgactt ccagttttaa attcaattct aatttacaca aatcccaccc    15660
actatgtaaa cttgttggaa aatgtcctgc actctgcact tcgtggcatt taaaacttcc    15720
acacacgcgc gcgttctttc tcgaagcccc gtgattgctt agcctcgctg ggcagcttgg    15780
cactgctggg agcttggctc gccctgccgg ggccgacgcc gcccgtcccg caggagcccg    15840 cgcgggctc agggcactca ggactccgca tgcgtcccgg ctccaggtgg gccccggcac    15900
cgccaaccgc aggaaacccg ccgagcccta aacgtctccc aagcggctgc agtctgcgac    15960
agagagtgtc cctcggtgga gcgccctgtg gctgcccagg ctacagccgt ggccgaggcg    16020
aggacacact tctgacctgg ggctccagca aagactgtcc gcgagcggcg actccatgcc    16080
cgcagccctc cgcccagctc agccgcccgg ccgcgggcac cagcagccgc gccacgaaag    16140
ggcgcaccgc gcgggcgccg tctctcctag gtgcgaaggc ggctgaggcc ccgcccggga    16200
ggcacccgcg cggctccgga gtgggccgga gggacgtccg ggggcgggc ccgggcgcgc    16260 ccgccctctg accgggctat aacacccggc cccgccgggc ggccgcgggt gggtagaggt    16320
gcgcgcctgg gacctggtga ggctgggggt gcgcggggcc gggcgcagct gtggcagctg    16380
ccggacggcg gaggcgccag gaggaggagg agagggagc gcgggcggct gggtcgaggg    16440
caccgaggct gcccgtgctc ccggtctctg gttgcacggc tcactcccga aggtgttgct    16500
tccagctttt gcctccttag gaggcaggga gcgtcagtgt cgggagaccc tgagaccgga    16560
gtaccgagac gtagctggtg atgccccgc ctgccctcat gtgttctcag gttcttctta    16620
tttttattca tctctagaac atggacttcc cgtgcctctg gctagggctg ttgctgcctt    16680
tggtagctgc gctggatttc aactaccacc gccaggaagg gatggaagcg ttttgaaga    16740 ctgttgccca aaactacagt tctgtcactc acttacacag tattgggaaa tctgtgaaag    16800
gtagggtccg tctcgtgaac actttgccaa accctcagtc ctccctttca gtattcatta    16860
aatatgcccc agcttcctgt ctgctcttcc acgcacctac tctgagtggc acagaacaag    16920
tcaaccggta ccgtgcgtgt tggttgtttt ctgcttttgt tgggaggaat agtaggaaga    16980
actgaatttt actggacttg tccattgtaa ttcagtgtca ctgagtcctt tccattattg    17040
gagttcttct gtcttttgg atcttgcaga cattggttat ttgggatgta tgttttagtt    17100 cctttcaag ataaactccc aagtaagtcc gtttatccgt ttcagttccc ctttgtgtgg    17160
gcttctttat atatgacttg gactgttaat gtcatttctt catgtctctt ttaaactgaa    17220
ataatgcagt tttgttggta agattctgt gtcatctgta gttagccttt tatttaaagt    17280
tatgcaaaac tatcatttct gcaagtttct tttaatctaa gtagtacagt tctgttggtt    17340
agatttgtgt cgtgtataat tagccctatg gcttaaagtt atgcaaaaaa gtggttctat    17400
gattaaaggc tgtttttaaa atgtatccat ttgaagaaga caatgctaga taatgaatat    17460
atattagtag tgattgaaac tcttcccagc attttcatat ttatcattaa taatttattg    17520
ttctaagtta gaaactacat aaagttattt tcatttttat agacagcaag tttgaatcag    17580
ataaattaaa taatttgttc aaggtctccc agatggtgaa ttttatagcc aggactggca    17640
```

```
cccatccggc caaggcaaat aatttgatca gatatcgtta tttcatcttt ctttctttct   17700
ttctttcttt ctttttttt ttttttttt tttggtcaga gtctcgctct gttgcccagg   17760
ctggagtgca gtggcgtgat ctcggctcac tgcaacctcc ggcttcctga gttcaagcaa   17820
ttctcctgcc tcagtctccc gagtagctgg gattacagga atgcgccacc acagctggct   17880
aatttttttg tattttagt agagatgggg tttcaccata ttggccaggc tggtctcaaa   17940
ctcctgacct tgtgatcctc ctgcttcggc ctcccaaagt gctaggatta caggtatgag   18000
ccaccgtgcc cggccgagat accattatta cttaatcatc ttttattatc ctgatgttcc   18060
caaagaggtt accagaaaac ttagtcctta aatcaaaagt ttcataaatt ttatgcaatt   18120
tggatctcaa cttttgtaa ggtgtgttca aactctacct tgattttagc tctgaacttt   18180
tgagtcaatt gagagtctca taattaccat attcttcatc attttcaaa aaaatcaagg   18240 ctatggcttc tatattaaag aaaaagtatt atataaatgt atttatgtgc aatgcgaagt   18300
caatatcctg ggctgtgtgt aatagtaact ttgttttaa acagcattgc caaagagatg   18360
gtgccagaat tactctatat tgctctataa tccaaaatta tagaggttgg gtgtgtgaga   18420
aatcatatct tgaatcagca tacgtattca gccttctgaa atcattttc cctagggcta   18480 gagtagagca atttaaaaag atctaggaat actaattata ttaattaaaa atatatagaa   18540
cacaactagc ttgagttatt gttcagtcat catttcaacc acaagatgat gaggatgttg   18600 ttaatttaa gtactaagtg atttggtaag gttttgtatt ttcaaacaca atgtgcttgt   18660
gacagttggg ggctctcttt cctaatatga atcagcagtt gtgatctatc ctgcatgata   18720
tcaaaccaca atcacagtga aagtcagcag gcttaattt gtttttaatt ttaccttgta   18780
tgcactcttg cggttaaagg cttgaggagt tatcatgtaa aaataaaatc tgacactagt   18840
ggttaaatat ttgtgttgaa tatgttgttc tgaataataa ctcggattaa gaaaaatccc   18900
aaatctgcca tttggctcca actggtagat gaaactgtat gccagtaact gggagtcagt   18960
tgccaaagtg tcactgcaca ttagtgtgac aattgagaga tggtgctcct ttgttggtgg   19020 tcttttcac tagatatttt ccctaaccat tctgccctct gatgtaagat aagtttgctt   19080
agaaaacaga atttatgacc aggcccagtg actcatgcct gtaatcccag caccttggga   19140
ggccgaggcg ggaggatcac ctgaggtcag gaatttgaga ccagcctggc caacatggtg   19200
aaacgttgtc tctactaaaa atacaaaaaa ttaaccagac atggtggtgt gcacctgtgg   19260
ttcccgctac tagagaggct gagaccggag aatagcgtga acccaggagg cagaggttgc   19320
agtgggccaa gatcatgcca ctgcactcca gcctgggtga caagagtgaa actctatctc   19380
aaaataaaag aaaataaaca gaatttatta tacacgtgtt atttatttat ttatttatat   19440
tacatgtatt aacgtgggca gtcttaccca gaagggaaag taatattcct aagtaactaa   19500
atacatgttt agttttgta aaaacttaaa tatatgtgct atgcctatgt aaatatatgc   19560
atatcacata ttttctttgt tgtaattgtg gattatattc tgcttgtttt ttcatttcat   19620
gttatttcct tagatatttc catgaattga caaagtcggt agatgtgaat tcgttgctgt   19680
ttagtattct atcctcttga ttatgtgaat tttcttagtc attcacctct ttgagcatct   19740
gtatagtttt tggttaactc tgttataaac agggatacta taaaaccatt gatacatgtc   19800
atgataatta ccttctatta ttattggtga ttttaaaaa cgttttatt ttgaaacttt   19860 taaaatccac acaaaagtta aacacatcta tacccagctt cagccatagt agaccatatt   19920
tcagttgagc cttttgaagg aaatcccact gcctagtgac atagtaaaga aaatcttagg   19980
```

```
tgaaacaaga gaagcaaaaa agtactgatg acttagttca gaaaaatcag aaaaggtaca   20040
gtgttcatca gttcgttcgt tcaatcctcc gttcaattaa ggaagcacct cccatttttt   20100
gccccaaccc ctttgtctag aaggatgcct ggcacataat caataatcta tatctattta   20160
tttaatggat caaatatttg ctgagcaaaa ggcatgggaa gcaaacaaac gtgtgtgtca   20220
ttcattccct gccattaggt agctcatttt caaatacaaa tgtatttact gtgaatttct   20280
cagggtagtc tctccacaca cacccaaaa ttagtttagg aacattttat tattttttta   20340
aaaaatgaac ccttgtgttg agggttgact atcaatagat agcaatgaaa gaactgctct   20400
gctacataca aaaccccaaa gggccatttt aaatgagatt tcctaccatc tatttaaga   20460
atcttgcatt gactgggtgt ggtggctcac gtctataatc ccagcacttc aggagaccag   20520
cctaggcaac atgggagact ccatttctta aaaaaaaaaa aaaaaattta attaaccagg   20580
cataatggtg catgcctgtg gtcccagcta cttgggaaac tgaggcagga gaatcacttg   20640
agcctgggag ttcaaggctg cagtgggcca tgatcgtgcc accgtactcc agcctggcct   20700
acagagcaag accctgtctc aaaaaaaaaa aaaagtatc ttgtcttgcc tcctgctaag   20760
tctgatcatc attgtatctg aatacagtag gcgggataat aacaccttcc ttactagtga   20820
taatactatt agagattttt taaagccagc caaatttagt agtctctgtt atcaagtact   20880
ttccatgtag taaatagttt aagacattat ttcgatctca gcaactcaaa gtaggcctta   20940
tcctcattta caaacaggt aaaatgaggc acagagaggt taattaactt gctgaagata   21000
acatagctaa gtattagaag attcaaactc agatctgcct atttcccaag cacctctcta   21060
ttctctttta aaaagcagct tgacatttaa gtctttaatc catcttgaat taattttgt   21120
ataaggtgta aggaagggat ccagtttcag cttctacat atggctagcc agttttccca   21180
gcaccattta ttgaataggg aatcctttcc ccattgcttg ttttctcag gtttgtcaaa   21240
gatcagatag ttgtagatat gcggcgttat ttctgaggtc tctgttctgt tccattgatt   21300
tatatctctg ctttggtacc agtaccatgc tgttttggtt actgtagcct cgtagtatag   21360
tttgaagtca ggtagcatga tgcctccagc tttgctcttt tggcttagga ctgacttggc   21420
aatgcgggct cttttttggt tccatatgaa ctttaaagta gtttttttcca attctgtgaa   21480
gaaagtcatt ggtggcttga tggggatggc attgaatcta taaattacct tgggcagtat   21540
ggccattttc acgatattga ttcttcctac ccatgagcat ggaattgttc ttccatttgt   21600
ttgtatcctc ttttatttca ttgagcagtg gtttgtagtt ctccttgaag aggcccttca   21660
tgtcccttgt aagttggatt cctaggtatt ttattctctt tgaagcaatt gtgaatggga   21720
gttcactcat gatttggctc tctgtttgtc tgttactggt gtaagactta aacgttagac   21780
ctaaaaccat aaaaacccta gaagaaaacc taggcattac cattcaggac ataggcacgg   21840
gcaaggactt catgtctaaa acaccaaaag caatggcaac aaaagccaaa attgacaaat   21900
gggatctaat taaactaaag agcttctgca cagcaaaaga aactaccatc agagtgaaca   21960
ggcaacctcc aaaatgggag aaaattttcg caacctactc atctgacaaa gggctaatat   22020
ccagaatcta caatgaactc aaacaaattt acaagaaaaa aacagacaac cccatcgaga   22080
agtgggtgaa ggacatgaac agacacttct caaaagaaga catttatgca gccaaaaaac   22140
acatgaaaaa atgctcacca tcactggcca tcagagaaat gcaaatcaaa accacaatga   22200
gataccatct cacaccagtt agaatggcga tcattaaaaa gtcaggaaac aacaggtgct   22260
ggagaggatg tggagaaata ggaacacttt tacactgttg gtgggactgt aaactagttc   22320
aaccattgtg gaagtcagtg tggcgattcc tcagggatct agaactagaa ataccatttg   22380
```

```
acccagccat cccattactg ggtatatacc caaaggacta taaatcatgc tggtataaag    22440
acacatgcac atgtatgttt attgcggcac tattcacaat agcaaatact tggaaccaac    22500
ccaaatgtcc aacaacgata gactggatta agaaaatgtg gcacatatac accatagaat    22560
actatgcagc cacaaagaat gatgagttca tgtcctttgt agggacatgg atgaaattgg    22620
aaatcatcat tctcagtaaa ctatcgcaag aacaaaaaac caaacaccac atattctcac    22680
tcataggtgg gaattgaaca atgagaacac attggacaca ggaagggaa catcacactc     22740 tggggactgt tgtggggttg gggagcggg gagggatagc attaggagat atacctaatg     22800
ctaaatgacg agttaatggg tgcagcacac cagcatggca catgtataca tatgtaacta    22860
acctgcacat tgtgcacatg taccctaaaa cttaaagtat aataataata aaataaaata    22920
aataaataaa aataaaaagc agcttgacac agatgggat gattccatgg aagttgaggt      22980
cattagtaga gggttttagg accatggttt gggcacattt gacctgaagg tatagctcta    23040
ccaaggatct agagctgttc aattcagtag ccattagcca ctaagcaatt gaggagttga    23100
aatatgacta gaccaaactg aggtgtgcta gaaagtgact ttgaagactt aatacaaaaa    23160
aggaaaatat ttcactaata atgttttata ttgattacat gttgaaatga taatattta     23220 gatatgttaa ataagaaata ttttttaaa ttaatttcaa ggccaaaagc agtggctcac      23280
acctgtaatc ccagcacttt gggaggctga ggcaggtgga tcgcccgagc tcaggagttt    23340
gagacccgct ggggcaacat ggcaaaaccc catctctacc aaaaatacaa aaaattagct    23400
gcgcatggtg gcatatgcct gtcatcccag ctacttggga ggctgaggtg ggaggattgc    23460
ttgagcttgg gaggtggagg ttgcagtgaa ccaagattgt aattgtgcca ctgcactcta    23520
acctgggtga tagggtgaga cccccatctc aaaaataaat aaatatataa ataaaaatta    23580
atttcacctg tttcttttta cattattgta actagcagaa gattaaaatt atatatatga    23640
cttgcattat attttgatcg gactgtgctg ctatagagtg caatttgtta ttattaattt    23700
tttcctgcgt acaaaaggaa ttctagttca tttagaaaat ttggatcata caacaaagca    23760
ccaaaaagaa aattaaaatc tcaccatcca aaggaaacat ttagtagact gcaatcatac    23820
tacacagttt tgagcctttt tacccccctg agtcaaatat cttatttgt ttgtccatgc      23880 aaacatgtta tctctaaaac ttgatttta atttctgttt tgtgtcctgt caatagatat     23940
tttattgttt aacttatgcc ccactggtga atatttagtt tgtttctaaa ctttcgctgt    24000
tatgatcaat gctgtagtga acatccttgt agctaagaca gcaaaaatct gagcacaggc    24060
tttggaatca cctgcccaag ttcaaattcc ggattctcag tttgtagct acgtgaccat      24120 gggtctttag aataattcct ggcacatagt aagtgctatg taaaagctgc tattattatt    24180
attattaata catacccaaa aaggaaatta ctaagtctaa agctgtttta agtatttgat    24240
atatatacca aattgccttc caaaaagatt gtgttgattt ataattcttt gggaaatgca    24300
tattaagaaa aataaaacaa ctcttctaaa acttacacta gtcataaatc aatactgtca    24360
ttagtgcttt gaaagatgat tgtagtatgt atttctcatt gttatgttgt aagtatgagg    24420
gagaatttat ttctcttgcc cctttcccta agaactctca ccttcccatc attaacagac    24480
attcactgaa ttcctctact aggagtccta taccatttca gatgttcaga atctcccta     24540 acattggtta agattcttgc tcctaagagg aaagtactat gttcacatac acagatctct    24600
catgatcact tgccctcaac tggatagatt ttagccggtg atttaccctc agaaaacagc    24660
attgtatata aaattttggc acaacacttg gtcatccgtc acactctgct catttcccaa    24720
```

```
atatgctcgt aaaaccagtt tgcttgagat cctgtataaa atgcctattg tgatgcaaat  24780
actgacatat tgaggatgaa tatgaagaaa accactaaaa tctaggaaat tcagctataa  24840
tatacatgtt tgtgatttaa agttatatgg gtttagtaag cctttcccct ttaacataat  24900
acgcagagta cctttctgag acatttatca gctatcagcc ttattcttat tcttgaaaca  24960
ttcagggttt cttaaagaca ttgcctttt tttttttcta tatggagtct cgctctgtcg  25020
cccatgctgg agtgcagtgt cacaatgtcg gctcactccg cctcctgggt tcaagcaatg  25080
ctcctgcctc aacctcctga gtagctaggg ttacaggcac ccaccattgc gcctggctaa  25140
ttttggtag agacagggtt ttaccatgtt ggccaggctg gtctcgaact cctgacctca  25200
taatctgccc atctcagcct cccaaagtgc tgggattaca ggcgtgagcc actgcgccct  25260
tcctatcact tatcttgtca tgcttacatt attccccaca atttaggtt ttttttttt  25320
tttttttaa gtagagacag gtgtctcact atgtagccca ggctggtctc gaactcctga  25380
gctcaagtga tcctcctgcc tcagcctccc gtagctctag gattaaagga atgagccact  25440
gtcccctccg cccacaattt tctaatgtcc tccatagggt aagatgagct acaattatc  25500
tgagcctaaa accaaaatct tttttgtata caaatacaaa atattcccc ccaacagttt  25560
taatatatac tgaactttt agggatgcca ctatatgtaa attgagggga aattatattt  25620
tgttttgctc ttaacgtgac tgagagatat ttcatattca gagaatcctg acaacagtga  25680
acaaagagcc aaaccaatct gcatttgtaa tctatatgtt cacggtgact ctcaagtata  25740
gatacaagca tgtgatttct ttgtcttcta gtggagtacc caagttattg catatggata  25800
ccatatctta tgtaaattgc attcttttt tatttctgct ttatatagtt tgaacactat  25860
attgatcttt tgaaattatg tatgtaaatg tgttagaatt gtatgccagc atgataaaat  25920
agaagttgca aaatattgga tatgaaagca agaggcatca tctgatagag ttaagaacta  25980
ttggtgtaaa agcacaaaga gagctgttaa ggacccactt gaagctcatg tggccagcat  26040
ccaaaaggtg cttagtttct gttcttaatc cctgaacgtg tgtatctgac ggtaacactg  26100
tggttacagc agtatctaca tttgagatgt gataactgcc attagtcctg attcctcctt  26160
tcagtttgtg tgtttagaac accccttct ctaagaatgc aaagtaagaa agtaagatgt  26220
aaaaaaaaaa acaaagaaa acctaaagt gaaattactc aaaacacaca cacacacaca  26280
cacacacaca cacacacaca cacacacaca cacacactct atatcaaata ccaacatgca  26340
tttgggttaa gggaaggaga ctaagtcaaa tttagtcaaa tcttcctgtt tggagctagg  26400
cttggtcctg tagtcccagc tacttgggag gtttacacag gagaatcact tgaacccagg  26460
agtttgaggc tgtactgcac tatgatcgca cctgtgaaca gccactgcac tccagcctgg  26520
gcaacacagc aagagtctgt ctcttaaaa caaacaaaca acaaacaaaa aacacttctg  26580
tctagtgatt taaacaatt gacattcttc ctagcaatta aatgtaatac tgtatagtag  26640
tttgtgaaga ggttagtaag tcctaatttg aatttgtgtt aaaataaaag acacaaaatg  26700
cacattaaaa atgtttctca tctctgtttt ctgaggactg ctgcatgtca caggttttaa  26760
aaatacacat tttctatctg tgaccttca catacatacc tttgtcaagc tcaactggag  26820
ggcttaatct ccactgcatc aaaaaaaaaa aaaaaaaat gctgccaact tcaaacaaat  26880
tgccttggag ctggcttcac agagttatca cgcacttacc cggagttgaa gataactacc  26940
ttgacagtgg ggatacaaag gcagtaatga tagtgcctac taccccagtc tttagtctat  27000
cacagaattc aggagaagcc aattaagtaa tccttctgtt tgtttaaaga actttcaatt  27060
agttgcttat ccagttttta aattattctg atgcaaatcc gtgaaaacta gaaccacact  27120
```

```
taaaaatcac aactaaagta tcatgaattg acagttattc aaacacataa ctaagcctcc    27180
tttcccacat aatacacacg cacatataca aatacaggca ggtgaaattt agcataacat    27240
catgttttta gagcacgaat aaatgttaga gaccatttga tcattcatta cgttaattga    27300
aacttagttc aaaatgttgc ttcctccagg aagccttttt ctattccctg ggcagagtca    27360
gaatctcctt ccacacctct tctcctcttg agcatcttcc agtaactcta tgttcacata    27420
gaggccaagg accaggcttt gttcagcttt gtatcctagg cactaagatg tgcttattac    27480
atgtaacaga tactctcaag gacaaagatt aagagttatt atgtgcttat taaatgaaac    27540
atatgaatgc aaatatattg tatgtagtat attaaataat acataagtat ataggatgta    27600 cattttaaa tatacttta tattgttaca tatattatat gtaactttat acacttttat    27660
atagttacct atattgtatg taagttcttc agtccctcaa gaaaatgaca ttgttttctt    27720
atgaactttt tgttaaaatt agttttatat tagtagtaaa taatatgata acttagagag    27780
gtagaattgg gggaccacaa ttatgcccca gttcaagata agtcactggc atgtaggaga    27840
aggcctcaga gaagttacgg actttcaggc agtaaaggac acagttgaat tattcactgg    27900
ctagcctaaa atgggtctac ccccacccct tgccttcagc cccctaaaac actgaccaaa    27960
catgtaataa gaaaagagta attataggag gttcaccacc atcacactca cccctgcctt    28020
cattaagaag tgtttaggct ggttgcggtg gttcacacct gtaactccag cactttggga    28080
ggctgaggcg ggtggatcac ttgaggccag gagtgcaaga ccagcctggc caacatggtg    28140 aaacccatc tctactaaaa ttacaaaaat tagccgggca tggtggcagg tgcctgtaat    28200
tccagctacc tgggaggctg aggcaggaga atcgcttgaa cccgggaggt ggaggttgca    28260
gtgagctgag agccgagatc acaccactgc actacagcct gggtgacaga gcaagactct    28320
gtctcaaaaa aaaaaaaaaa gtgtttaaat aaatgcctct ggctttatt gaacagtcca    28380 ggaataattc aagggtctgt cacagaattt tgacaaagaa aaaggtggg agggatcatg    28440 tgaagaaggc cttttttccc ccaagagtta agcaggggcc aggcacagtg gctcaggcct    28500
gtaatcccag cactttggaa ggccaaggca ggccgattgc ttaaggccag gagtttgaga    28560
acagcctggc caacgtggca aaaccccgtg tgtactaaaa aaatgcaaaa aaaaaaaaa    28620 ttagccaggc atggtggtgc acacctgtaa tcccagctac tctggagtct gaggcgggag    28680
aatcacttga acccaggagg tggaggttac agtgagccga gactgtgcca ctgtactcca    28740
gcctggccca cagtgagtct ctgtctaaaa aaaaaaaga aaaagaaaaa gaaaagaaa    28800 aaaaagctt aagcagagat atgaaaccct tccatttaa gtgtctttc ccccctctat    28860 actcagaaat gttgtactta ttttaggtga aggcagatga tatgtctaac tattcttgct    28920
gtgagtggtc cagaagggca cagttttgga aatacacaga tgaactgttg aaggtagttt    28980
caccttaatt tttagtcctt gttaaatatt tattcccttg tccattgttg gtgactcagt    29040
tgagcccact cgttaaaatc cttttcacgg ggatagtcac tcttatgaaa acatagacac    29100
ctagagacat gtgggaagcg tagggtcatt taacatgtgg cgattctaca gcagttttcc    29160
cattgtttaa ctggagagat ttatttacag cttgtgttag gctgttcttg ggttgctaga    29220
aagaaatact gggtaattta taaagaaaag aggtttaatt ggctaagcgt tctgcaggct    29280
gcacaagcgt ggccccagca tctgctcagt ttctagggag gcatcaggag gcttttactc    29340
atggcagaag gtgaagcagg accaggcacg tcacatggtg aaagcagaaa caagagaaag    29400 aggggtggg aggtgccaca cgcttttaaa caaccagatc tcgtgagaac tcactcatta    29460
```

-continued

```
ttgtgaggac aacaccaagc catgagagat ccactcccat gacccaaacg tctcccacca   29520
ggctccacct ctaacatggg ggatgacatt tcagcatgaa atttggggga acaaatatct   29580
aaactattca caccttacta ataatactaa atgtgcacag ttaaatttca gataaagatt   29640
gttcaattgg ggcagacacg taattttttc cattgctctt tgggactcag atgaataatc   29700
ttagtgtggt agagataagc ctagctggtt tgtcatgtgt tactgtcagt tcctttcaat   29760
ttatgaagaa acagaaagat aaattgggaa atgtcacatt ctagccttga cgaactttt    29820
agttggactt ggccatcttt cgagttgtaa gaacatgtac ttctaagggt acaaaatgtg   29880
tttccaaact ctatggcata cagttctagc ataacaccat gtcagtcaat tgcagaaact   29940
tccaaacatt ttttacactg agagctcttt ggtcaaataa ttcttgcttg gaagtaaatc   30000
ccagtctgtg tgtgccaggc actgtgttag gctagagaca gagtcatgag caaatagcat   30060
ctctgctctg atgtttctta catgtgctag tgagggaggc aaacaaaaaa caaggcgagt   30120
tcagattttg atcattgcta tgaagcaaat acatagttta gtataatgga gagtgacagt   30180
tactgtggaa cataggttcc atgaaagcat ggagcctatc ctacttgtca ctgtattttc   30240
agtgcctaaa acatagcagt tactgtttga gagaatgttg tatggaaaga atgacaggag   30300
gcctgcctga aaagatggta ggttaaagtg agatctgaa aggtgacagt cagctagatc    30360
ttatagcctg attacaaagt gcacaaagtg caagtgatgt gcaaaggcct cgaggtggaa   30420
agagtagaac agaagtgaga ccagggtggc tggagcccag tgagcaaggg gaaagtggtc   30480
tttgagcaag ttggaaggta cacaggggac agagcataga gtgccttcta agccaattct   30540
aaagtggaga gtttgaattc tgttctgaga ataatgggaa accattgaag ggttttaaga   30600
agagagtgat gcaatctgat gtgggtttta gaaagataac tttagctgct gaatacagaa   30660
aatggccaga atagaagcag ggagactaat ccagttacag tagtcctggc aaatgttgat   30720
gatggtgatt tggattaaga tgctctgtta ggaatggagg caagtgaaag gattggaaat   30780
ctgtttttgga aataaaaacca agagtacttg ctaatgggtt gggttgggtt gggttggatt  30840
ggattggatt ggattggatt ggattagatt ggattggatt ggaggaggaa ggcgtgtgag   30900
cagaagagga aaatcaagga tgatgcttag gttttgtgct cgactgagtg tatgaagtgt   30960
tcttatgtta gatggacaaa actggaagag gacagatttg ggatgaaatc aagggctctg   31020
attcagacat tttcttaga aattgtgaac tcctcaggag gtatccagtg gagacggttg    31080
ggtatataag tggagctcaa gagagaagtt tggctgcaga aagaaagttg ggagtcatca   31140
acatagaaat ggtattgaaa cctgcaggac taataaaata atctagcaag agagtagaga   31200
taaagaaaag aaggccagaa tcgagctata gcaccgtcac acagttagtc tgatagagta   31260
gaggagccaa gaatggagat gggaaaagat cagtaatgag gtagaaggaa aattaagagt   31320
gatgtcacag atgtcaaaaa ggggagtggc tcaagaaggc agttgttttg gggagtacca   31380
tgaccaccta ctagtgattt gctgaaagga ctcactcacg actcaatata gaatcatatt   31440
caaggctaag atttattaca gcaaagggta tggtgcagga acagcaggat acagatatat   31500
ggtggcaaaa ctagagaagt cgtagtaggc tttcttgtcc tctctctgta gggattccac   31560
atgtttctca ggaatgcatg tttctctcca gctgtaaact gcagagacat atgcaaaacg   31620
cctccacccca ggaaagccca ctcaagtctt aggggttcag agctggtcaa gggagctggt  31680
cgtgtagcta tgtaaccagc caggatgcag accccaaact aggtactagg atgcatcagg   31740
aatcttcatg tcaactttaa acaatgatac tgtcttgata tattttgacc actgccttga   31800
gggcacaaaa ataacataac taattagtaa gcatttcagg gagtttagtg ctcaggattt   31860
```

```
gggtcagggt cattgctgtg actgcaggtg ttcccaaaga caagcaagaa ctgagtaaaa    31920
catactggct atgttaactc tttcctctag aggtcatggt taatgttgaa tgcaggtgaa    31980
agtcaaaact gagagccata aagttaattt ctatatccca aagtatagtt agtgaaatta    32040
tatttctctc cagatagatt cattccactt atttagtaaa catttattga atgcctaata    32100
tagttcatgg catgtgctag catgagacta taggggtaaa taagttagac atggcacctg    32160
ccctgaagga gttgacaaac caataaacgc agatgtcatt agctgtgtgc gagaatatga    32220
cagaggtctc acggctgaga cctgaaggat aagagatcag ccaggtgaaa agggaaaggc    32280
gaggcaataa atagcacgtt caaaggcctg gaggtgaagg agcatattga ctttgaggag    32340
caaaagaagt tcagtgtggc tggaggggag aaaggagaag gtgagtgtgg ggtagattat    32400
ggaggacctt atacaggctg ttaaacacgt tttgcttcat ccacggggag atataatcct    32460
aagggttttt gcttgatagg aaaatgacag atttgttttc ttgattgaaa aatttctgat    32520
aattttacag ttagttttgc attgcaacag agattctctc tctctctctc ttttttttt     32580
ttttttttg  agacaagagt ctcgctctgt cacccaggct ggagtgcaat ggtgcgatcc    32640
cagctcactg caacctccgc ttcctgagtt caagcgattc tcctgcctca gcccccgagt    32700
agctgggatt acagggtgt  gccaccatgc ccagctaatt tttgtattta tagtagagat    32760
ggggtttcac catgttgtcc aggttggtct cgaactcctg accttgtgat ctgcctgcct    32820
cagcctccca aagtgctggg attacaggca tgcaccaccg tgcccagccc agagattctc    32880
tttaagaaat ttggtgcaac agtcatttct gggacaaaaa gtagtgagaa aatacaaaca    32940
caccagggta aataaaccag agcgccacaa aatgtaatat taagtgtgta aaaataataa    33000
tccctgagag ctatcagtgt gaaaagtttt tatttgaatg ccgtaattga atggaattgt    33060
tcatttaaac cttcaagtga atttatttt  atgtctaaaa cttattagaa atgtttcaat    33120
ggtgattata tgtagtttct ttttgcctt  caacagagca cagatcacac agaaaggaat    33180
gattttttt  ttaatcagca attttggaga caaattctat gaatgccaac ctatacagaa    33240
actgacaagc attaattatt cagaatgtaa agagaaatgc cagagtatta aggaacagat    33300
acctagattt aaacataatt ttggaatatt ataattatta tgaattacaa ccacttatat    33360
ttgaggcagt atgtaacagc tgtgtgcgtg agcaggaaca tgagagggaa cgtaacctgg    33420
tctcattttc tagacaagcc attcaagagg agcaaagaga gtgggaaaat gaaagcaatg    33480
ccactactga ttattgaaca tctttatctg ccatgcactg tgctaggccc tttacacatt    33540
ttccttcttt aagctattta aaaactgcga taagttcctt acattcccat tttataggca    33600
agagcaaata gattttacag atgaagaaat tgatgtccca aaatgatatc ttggtaggtg    33660
atagattcgg ttcggtaacc caaatgtgtc ttttagcgat ttatgtattc attcaacaaa    33720
tattcattga gttcctactg tctaccagaa cttttgtaag gggatgcaaa gaagaacaga    33780
cccaggtctt tccctttatg aactagggca gtgggcctta cacccaactg ccgtaatggg    33840
aaaagcattg taatggggct tgttcgtta  cagtcaacag tgcagtgtag ggatgctttg    33900
taagctggcc tacagggtga ttggtaaagt tgagaaaggc ttatcaggga ggctgacatt    33960
tgaacaaagg tttggatatt accaggcaga gagatggagg tggtaggaat tccaggtaaa    34020
gcgactggga aaacacatgc tgtgcttggg tggcaggagc agtccaggga ggacatggtg    34080
ggactgtgct gcaagaagcc ttgtatgcca aggagatgag acttcccttg tacatacagc    34140
caaggataag aatttgatga cgatttctaa tgtatccttag catctaagtt cccttaattt    34200
```

```
gtgctcactg gaaaccacag agtttagaa ggcttttgtc attgtggttt aaaagaaaaa    34260
aatagattgt tcaaagaaca gtgatacata gggaaaatat tttgactcag gaacgtaatt    34320
tctcactaaa attggcaata tttgtagccc catgggaact atgtttccat aggacattct    34380
gttcgctgtc cttgggaagc tatctaaaaa aagaagaaaa aaacacaata aaaagaggta    34440
tttggggatc agtaataaaa gttgtatact ttattgaatg tgttactgtg tactagctac    34500
ttatccatat tattttaaat cctgacacct attaaataat aggtagtatt atccctgttt    34560
tacagatagg aaactgaggc tcagaaaaaa gtgacttgcc tgagactact tagctagtaa    34620
ggagcagagc tgggaattca aacccaggtc tgtcaggatt caaaaccccca gttcttccag    34680
tctctagagc ctggtctcta gagcctggag acttctgtgg aggtgaccta ggccacttca    34740
ataggtgagg agacagagga ccgcttgggg atgcattcct taaatcagag cagctgattc    34800
tatgaatgcc aacctaatac agaaactgac aaacattaat tgttcagaat gtaaagaaaa    34860
ctgccagagt atgaaggaac agacatctag atttaaacat aattttggaa tattgtaatt    34920
attattaatt acaaccactt acatttgagg tagtgtgtaa cagctgtgtg catgagcagg    34980
aacttgagag ggaacgtatc ctggtctcat tttctaggca agccattcaa gagcagcaaa    35040
gagaatggga aaatgaaagc aatgccactg ccgattattg aacacctta tgtgccatgc    35100
actgtgctag gctctttaca cattttcctc ttttaaatta tataaaaact ctgtgataag    35160
ttttttaag tatacagact tttgtgctaa attggaaaac ccgtactgga acctgggggt    35220
gggggcgggg cagaggtctt ctaatgactg gccttgtgct ctttaagctg cactagctat    35280
cccactttga aaagaatgtg tgaaacagag ttgcagtcat gcatactcca tctccaaaga    35340
atggattcat tcttcaggcc atagtatact gactataatt ttctgtttgt aattacccag    35400
attccaagcc tgtttatagc atttatacct gaggaatgga atagtgagga tttgaagagg    35460
ccgcagtcct tgaggttttc tttgataata atatctgtgt agctgcatca aacacaaatt    35520
tgatattctg tgtatctgta gcacaggtca tgtgactgta aattcttttg atatcttgtt    35580
gcatactgag gtcaaggaac tggctcttga tgtaattccc cgcatcctca tgggagttgt    35640
taccatcata ctctggaaaa caaatgctga gatggattaa cttttacac tgggtttccg    35700
catgggattt tataggaata aaggttccac taccagcagt gagtagcctg aagtctgcca    35760
cattgaccag gaacctttgc aagaataaac cgaggatgtg ccctctgcag gtgaatgtgc    35820
taggctctct ggggttgcca aggagtttga gtccccatcc ttgagtcccc atcaactaca    35880
tctagttgat gtacacgtga tcctttgcaa aggttctgag ccctctaaaa ctgatcaaaa    35940
ttgcatctgt tagaaaatat taaatatatt ctatatatca agccaaatac taggagcttg    36000
tgtaagcaac agagtatctt ggtggatcac gtgggtgttg ggttaggcaa aagatcccac    36060
tgttggccct ccccacaccc acatccttac tatgctctgg gcagacagag ttactccaac    36120
tatctcaaaa tgcccagaaa cccttaacca cctctactga tttgcctgta ttcaggagcc    36180
tccttcttca cagctgagat tcagacttca ttgagggaca aggtgaatga gagggtaggg    36240
gacagtaggg ggcagaatct ggtcatcagg aactttggac tttccagtga gcacagactg    36300
agatacctca ggtgctaaga ctgcagcacc cctggaggaa gactgtacac tagacaacaa    36360
caaggctggt tggcaggaca gcatctaccc agcatcctta acatccggga ggagatgatg    36420
gtgccgtgta gggacacttg accctgccca tagcagcctc agccctgtg catcctggga    36480
gtgaagtgat caggtcatgc aagtaactac atcagtcctc accactggga tcattgctac    36540
agagggaag gcttttccct gtgtgttgga gatggagata gaagtgtatt aatggaggaa    36600
```

```
aacaaaataa gcttttacat ctgctaaatt aacagaatcc caggctgcca aaaccctgag  36660
gcttgctcaa tcagcagtcc aaactgtatt tcctctaagg gacaaattat gagctgctgt  36720
aaaggtacac acagtctagt gagaaaccat tcaattttga gggggaaact ctagggaaat  36780
agagtaagtt aaaggagtag agtgtgccag tatgagaagg caactctcct ggagtttgag  36840
ttccaaaact cagtgggctc ataggtcatg gtgtgatctt agaagtcata agtgaccaac  36900
aaggagttta ataacgcctt ttcttatact ccctcttttt acatagcctt tataccaagt  36960
tatcatctgg cagtcatttt agatataggt ttctaagtta gacggtaggg tccaaatgaa  37020
gtgtttggca aagtcatctt aattttttaa aacttgatat gaaaaagatg gtggtatcag  37080
gtattgaaat tgaggagcta tcagaatagg gaaaaattcc ccatttatgc ccatactcac  37140
aaatacacaa atatttataa acaataatga tacaggcagg catggtggct cacacctgta  37200
atcccaccac tttgggaggc caaggcaggc agatcacctg aggtcaggag ttcgaccagc  37260
ctggccaaaa tggtgaagcc ccgtctctac taaaaataca aaattagccg agtgtgttgg  37320
cgcatgcctg taatcccagc tacttgggag gctgaggcag gagaattgct tgaacccagg  37380
aggtagaggt tgcagtgagc tgagatcgtg gtattgcact ccagcctagg caacaagcgc  37440
gaaactctgt ctcaaaataa taataataat aatacaactt atttttttcc ctttgggggg  37500
ctttccagca aaaaccagaa agcctattag acaaatttta aaagagctgt aacactataa  37560
taagactgtt taataatggt tgagaacaca gagcccgaag aacacagatt gcctgggttc  37620
aaatcctggt tctgctgttc agtggctgtg atcttgaact actgtcttac cctatctgtg  37680
cctagttcct attttgtaaa atagaaataa tagttctacc tcgtaggttg tcgagagggc  37740
taaataagtt aataaacata aagtgctcag aatatgattg gcacataagt gctatggaaa  37800
tatatgctac tcttactgca gttacataaa ttgtgatatt tggcagcctt gaagcgtggc  37860
cctgccatat gctttgtgtt taaaaccctc aaactactgt ttattgaggg catctttgat  37920
gtcaggcaca gggctaggca atgttcctgc tgtatctcaa tgaatctaca caacacccta  37980
tgaggtaaat accaatttac agctttagat actgacttgc cagtggttaa gtaacttgcc  38040
caaggccaca aagcaagtac ctggtagatt caggactgaa gcttcaagtc tagagagctt  38100
ggctccagcc gcagctgcag tttgggctga ccttgttcct gccagcacac tttgggacct  38160
gggccataca agttatagca tcctggacag accctctatt ttatagaaaa ggaacctgag  38220
gccctaggat taaatgaatt gccagaggtc actctccaaa gagactctga ggtccagatt  38280
aggaaacctg aactaacatt gaagccgtgt ctttctgtat aagatccaac tgcttgtggt  38340
atgtttggcc aaaaagactc aggttaaagt cagataccaa ataatatatt gacatctagc  38400
atatttatgc ccagatgccg tatagcaaat catccttcac tttaattagc ttatagttat  38460
atactcgaca atgtgaatga acagagaaaa acaaggtatt ttttttttcat cttctaaatt  38520 tgcttgggaa attcctccgt gtcttttaca ggtttaaaaa tcatgtttaa cgataatgta  38580
gttatcttag gaaaaagacc aacccatttt tatcactctt tatcattggg ccatcacaga  38640
tgagagcttt ctatcttata gaatcatttg cacaaagtat atatgaggat atacagcatt  38700
gtatttgtag catttcttat aatagtaaaa aaatgaaatg atacagtcat ctagttaatg  38760
ccactgagtt gtacacttag aatggttaaa taacaaattt tgttatatgt gttttgccat  38820
attttaaaaa aataatagtt taagaaacta gtgacttgta tacttaaact gagtggattg  38880
tatagtatgc aaattatgtc tcaataaaga tattttttaa aacccataca tttatccata  38940
```

```
gagaattggt cagattatgc caaacccagt caatggagta ttttacaacc tttattaaag    39000
aattaggtag atttatatgt tttgacatgg gaggatgtcc agaatatatt gtgaagtaaa    39060
aaaaaagttg atgtgcattt ccatatgctg tatacacacg tctacagttt tgtcttatga    39120
gtaacactct tgtaaatgtc attatgcaac ttggcttttt cacttatgtg tgttatgtta    39180
gaggttagta catatagaga tacctcattt ttttaactgt ttcaaactat tctgtggtat    39240
aatcttatct tagtttattt agtcatttcc atattgatga gtctttaggt catttataac    39300
ttttagatat ttcgaagaat gctgcaataa atactgttaa acaagcacat tagctccata    39360
atttcccaag ataggcacta ctaaatcaaa aagtacatgc attttttttcc tcaagtttct    39420 ttctttcatt gatgatgctc ttcttcctcc tcttcttcct cttcttcttc ttcttcatta    39480
ttattattat tattatactt ttaagttctg ggttacatgt gcagaatgtg caggtttgtt    39540
acataggtat acatgtgcca tggtggtttg ctgcacccat caacccgtca cctacattag    39600
gtatttctcc taatgttatc cctcccgtag ccccccacc ccccaacagg ccccagtgtg    39660
tgatgtttcc ctccctgtgt ccatgtgttc tcgttgttca actcctactt atgagtgaga    39720
acatgcagtg tttgattttc tgatattctg atagtttgct gagaatgatg gtttccagct    39780
tcatccatgt ccctgcaaag gacatgaact catcctttttt atggctgaat agtattccat    39840
ggtgtatatg tgccacattt tcttaatcca gtctatcatt gatggacatt tgggttggtt    39900
ccaagtcttt gctattgtga atagtgctgc aataaacata tgtgtgcata aaaggtatat    39960 gcattttttgt gcttgatgga tactgacaga ttaacctaca agaggatgta ttatttacac    40020
tcccagcccc acgtgagtat gtgtatttcc ccacatccta accaacacta atttttttcc    40080
attctaatgg gtgaaaaaaa aaatctccat tttaagttgc attttcactg agcatggtgg    40140
tacacaccta cagttccaga gacttaggag gtcaagatgg gaggattgtt tgaggccagg    40200
gccaggagtt caagactagc ctgggcaaca tagcaagatc ccatctctaa cgaaaatttt    40260
tttaaaaact agccaggcat gatggtgcat tcctgtcatt ccagctaccc aggacaccga    40320
ggctggatga ttgcttgaac ccagggccat ggtcccacca ctgaactata gcctgggtga    40380
cagagcgaga acctatctct acttaataat tagtagcatt tacatgattg aaaatcagaa    40440
tgaacatgtt ttcacattaa ttcaacatta gataaacatt gaggtactgc cccagatgaa    40500
caaacacaaa cccctgcccc tgtggaactt ctgttaaact ctattggtca tttctatttc    40560
ctcatgccat ttgcctgttt ttctatttat tcatgctttg ttatgtgtgt ggcaaatatt    40620
ttcacctctt ctgtggcttg tcttttgagc tccattttca gtatcttttgg ccttacagaa    40680 gttttaatt tttatgagat cgtattcgtc agtccttttc tttatgcttt tatgttccat    40740
gcctcactta aaaaggccct cttttcccca aggtcataaa tatattctat acccttttca    40800 atattttat ggttttagtt tttatgtttta gcacctaact ccatctggaa tctatttttg    40860
ggaatcgagt ggtatgtaga tagatttcat gtctgacaat atatatttt gagcactcaa    40920 atttttaaaa agtatgtatg actttggtaa gcagaaagag ccaagaggag tttgaagaga    40980
cactcagaaa gtggatgtcc attctgggtg ggcccaggag tttgcaatttt tagcagatac    41040 ctccagagaa aagagaaagt gatgagaaaa aaaaaaaaaa agctgtgtcc tgtggagtag    41100
attcaggtca taatggctgt aggtagagac acagcagaaa gagtagcccc gggttggcct    41160
tgtatcctgg tacctacagc accttaggaa atacataaaa tacatgaaat gtcacagctt    41220
tgcaagaact agaagaccag ccagaatgaa tcagagaagg gattcttcag tgtttctact    41280
tgtaatggaa tttttaatcc ctcatctggt acaaaaatga gtttgagata atagtccatt    41340
```

```
taaaaataac ccaagccggt gtggtggctt acgcctgtat tcccagtact ttgggaggcc    41400
gaggcagggg aatcacctgt caggagttca tgaccagcct ggccaacatg gtgaaacctc    41460
gtctctacta aaatacaaa aattagtcag gtgtggtggc gggagcctgt aatcccagct    41520
acttgggaag ctgaagcagg agaatcactt aaatccggga ggcggagatt gcaatgagcc    41580
cagatcgtac cactgcactc cagcttgggc aacagagtga gactccatct caaaaataaa    41640
taaataaata aataaataac caacccagcc ctggattaat gatgaatttt cattctggct    41700
agcaaaggtt agcaaaagtg gatgactaca tgtaggcatg ttaattaaca cttttagat    41760 tctgaaaaa gaatgttgtg tggcagaaat atgggtacaa atgtgcaagc cttctgtaga    41820
tgattcttta aaggcaggtg gagtgggagc cgctgggcta acctaccca aatcactgca    41880 cttccttct tcccttgtca ttaaaaccat atgaccccctt tagtgtctgt gttgcactca    41940
tgagttcaga agttccaatg catctatcaa acacatgtgt ttgcctactg tgcatgttgt    42000
tctaagtgct ccttcactgc ttctgacaac cctatgaggt actattataa gcctcctttt    42060
acacatgagg aaactgaggc tccagagagt taaataagtt gcccatagtc ccacaggcag    42120
tggtggcatt gggatttgga ctcaagttgt ctagctccag gttcgcagaa tcaccctaat    42180
aatgtgccct ccaaattggc tatttcagca actgcagtgt tcaggaaaga attatactct    42240
gatgagcctt catgaggcag ggttgaaaaa cctgtgtcag gaaagatat gacaccttac    42300 tggttatcag accatgctag aaggagcctc tttaaaatcg aacaacagag ccactgctct    42360
ggtgcaagca gcactctcac ccagccctct gacctcagtc acagtgtgag ctctatagtt    42420
cctggcaaac tttagccatg gggtcaaaaa tggagaagcg tgccttcagg tataagatgt    42480
gatgtgttca tgcagggatt agctctgttt aggcttaatt ctggaagcca gggttcttaa    42540
tttggttccc attccctgac ggaatactat gcagtcctga taatgaatga tttacattta    42600
tacaacagta tgcatggatg caccacaggg gacagtgcct ggaaataggc acaagggtgc    42660
tttgaggctg ctgtctacac aaatgtgtgt ttagtttatg aaaatccaca gtggcgcctg    42720
taatcccagc actttgggag gctgaggcgg gcggatcatt tgaagtcagg agttcaagac    42780
cagcttggtg aaaacccgtc tctactaaaa atacaaaaca attagccagg tgtgatggcg    42840
gatacctgta atcccaggta ctcgggaggc tgaggcatga gaatcacttg aacccaggag    42900
gcagaggctg cggtgaacca agatcgtgcc actacactcc agcctgggtg acagagtgag    42960
actttgtctc tcaaaaaaaa aacaaaatct acagtgagct cttcagcata tagctttctc    43020
tgcatattgt attccatgta ttcattgtac tggattcaat gtacagtatt ctatgtatat    43080
tgttatttca ctgaagagtt ttttcttaat ggcgtgaatt agagtcagct gaggtatttg    43140
tgaaaaatgc agactcctga actcacgcct caagattcct gttctggatg gggcccagga    43200
gtttgcagtt ttttacaaat acctcaggta attctgctgc aggtcatctg aagatatacc    43260
tgtaagaaca tagcaaagct gcagacctgg tctgctgttg atgtgcttaa tactgggcat    43320
caataggact ctataagtag agcaaaagaa tgacttgaga atgactaggc tcacacattg    43380
ggatggtagg aaaacagcct ggtgcactgc aagggtaaca ccatcttgaa gcgaaaccac    43440
cacgatgacc gatgcttgag tcctgcatgc caaggtgttc ttgcagcaag gccaagaaac    43500
aatgcctgta gcacagataa cccctcataa acatgcttat ctgacttccc cagtggtcac    43560
cagtgttccc caggaggatc tgagacatga ccagctgtct ttactctaaa cacttgctat    43620 ataaggatc atttctggtg ggtggacaca gggactcact ttctggagca gcccaagaca    43680
```

```
tcgcttctat ttgtaagtcc ctattaaata ttttttctga agaactggat ttatcagcct    43740
ctttcttaag cctcttagtt ccctctgcct ttgtgggtag gtttgcgtag acctactcac    43800
caagaaacaa ggctatatct tacatgtatc catgattttt tttaatgcac aaaaatgtaa    43860
aaagactata taaatacct acaacaagat ttctgttggc caggtacagt ggctcatgct    43920
tggaatccta gcattttggg agggtgaggc gagtggatca cttgagccca ggagttcaag    43980
accagcctgg gcaacatagc aagaccctgt ctttacaaaa agtacaaaaa ttagctgggt    44040
atggtggtat gtgcctgcag tcccagctac tcaggaggct gatgtgggag gattctttga    44100
gcccaggagg tggaggcagt ggtgagctga gatcacacca ctgcactata gtctgggtga    44160
cagagtgaga ccctgtttaa aaaagagag agagagagaa aaaaaagat ttctctgaat    44220 ccttctcatg cgtatcatga gagatgtttt aaaatgtttc tatattttgg ccgggtatgg    44280
tagttcacgc ctgtaatcct agcaccttgg gaggctgagg cgggtggatc acctgaggtc    44340
aggagttcaa gaccagcctg gccaacatgg tgaaaccccc atctctacta aaaatgcaaa    44400
cattagccag gcgtggtggt gcatgcatgt aattccagct actcgggagg ctgaggcagg    44460
agaattgctt gaatccggga ggtggaggtt gcagtgagcc gagatcacac cattgcactc    44520
cagcgtgagc gacaagaatg aaactccatc cccccaaaaa aaccactttt ctgtatttta    44580
atgcacagtt taaaaatgcc agacctggct ctattctact taggtttctg ttcattagat    44640
aggagtcatt catgtatgac tgaatcacta tgaggatcct cctctctctc ttcttcccct    44700
tccacccaca tgccaggctg tggttcagac tgccttctgc tttctcacgg gtctctgttg    44760
tgtgatcttg tgcccacctc tctgtgtgtt aaatggagag agtggcttga acagtaccct    44820
catggttggt cttcaagagc tcatctaatt ctgaatggta gttgggcatg tctgaaggta    44880
ttagcaattc tgttgctcag cattgctgat gtattgagca atgtgaaaac cttggcgaat    44940
cttgttgcca tcttccccta agaatctgcc tcatcctgaa gcccaaccat ttgactctgt    45000
ggtaaaatga agtaacttca gtaaggtcca tgtctaccaa tttcttaatc tcatttgagg    45060
taaatagatg cacattatca gaaaggactg gccactatgt actgcaaatg atgggcacag    45120
agttgtgatt gtcccagcag acttgagatg agctagggat acatcagtcc attatgagac    45180
ggtatctgtt atagtcaaga gtgtctctgg aatggcttct tgtaattatt tggactttct    45240
accaaggttt ctgtgccata gcctatggaa aagtagattc cttcaagag acctgacttg    45300 ccaagcatgg tggttcacac ctgtaatccc agtgctttca ggggccaagg cggtgggatc    45360
acttgaaacc aggagtttag gaccagcctg gcaacaaag tgagacccc atctctacaa    45420 aacattagcc aggtatagtg gcgcatgcct gtggtcccag ctacatggga gggcaaggcg    45480
ggaggatcac ctgagcccag gagttccagg ctgcagtgag ccacgttcac accactgcat    45540
tccagcctgg gcaacagagc aagacccagt caaaagaaag aaagaaagaa agaaagaatg    45600
agagaaaggg agggagggaa gaagggaggg agggacggag ggacggacgg cgggacggac    45660
agagggaagg agagacagag ggaggaggc ctgacttgta tatttatgtg cacgaaatcc    45720
gttctaggcc tctgaatatg gcacctggcc cactctttct tgagaacagt ttgccagtga    45780
gcaatgtgcc tcatgtcctt tgtgaaactg gcagagcata aattattaat ttaaaataca    45840
caaactaaga tcaagataag atgtgcttta atgaacgggt aaactcaaat ggcttattaa    45900
caccttcatt tcctcatgct gcttctgaaa tgggcatttc tcaacttaca ttttaaggta    45960
ggagctgatc tgagatgcaa gttaattata cagtttgtcg aagccaaaga gttgggtttg    46020
ggagattttc tgacctgaaa atgttcagtg gcggtgccca tgtaatcttg ggcctactct    46080
```

```
gacagacagt tcagagcctt aacattcagt gttggtcctt tggatatatt gaacataagc    46140
tacagtttac gggtatgaga ggacattatt gactgagact tcaatagttc caaggggga     46200 aaaaaagaga aagatggctt ttttaaagct actgtcttca gctcaggaaa aacatgtga     46260 tcagccgact gtaaatgcac agcttgagaa atttagcaat tcccaaaata ggttcaagtt    46320
tctttgtgag catgtaggcc tacttgcagg taacattgac tttgttaaca acgtttgtta    46380
acaataacat tgtaggcagt taatgtctca gagctcttat agatacaaaa gaaataaac     46440 ttacaacttc cagaaagcat cttctcattg atgagtctaa ataatgctca tctattggag    46500
aagcaacttg ttaatagtga cttttttgtca cttttgtaga gtggggagag ggacatggga   46560
gatgaagctc ttactttatt tgggaagtga gatgtctcaa gttctttatt ctaaaaaagg   46620
taaacatcag ttgcctctga ggtagtaata aagaaggtc tgtttttactt tggaggaaca    46680 ttaaccttag agtaaaacaa acgaaaacac agttcaaagc ccaggctgtc tgagcccatc    46740
tcgtcatttg taaaatgagg ataataatac ctgccttact tatctcatgg tgtttctgtt    46800
gaggattaaa tgataaagca ctttggaaat tatgtaaaat atctgtatt taagcaggta     46860 tgatttcccg aaatccttga gttttttcctc tgattccatg attatgacat cacttaaata   46920
tgccacccct ctgctatcct aatacccca atctcagtga aacactggaa aagtccgaaa     46980
ccaatagaga tttctaaagc agatcccctt attatgcccc tcaattagtg atcattgtta    47040
gtgggtctgc tcagagcatc attgccaagt gctttgataa gctgaagaaa tctgttgata    47100
atttcttgag gcatggtatt tcagtgtgtg gaatacttgg gtactagttc ttgggagttt    47160
tttaaagtaa aatacttata tttgtgttga ctttgcaaca gcaggtacag caaatttcac    47220
atggtacctt gctacagaaa ttaattagta ccactcatgg tttaaattat gtagaatgat    47280
agtatgctca tattcttctt ggctgtctta aaaatgaata gaaacaaaaa ggtaaacaaa    47340
gctcatattt acctctcctt ggaaagaggt tgagtgattg tcatgtagct tctcatttat    47400
caagtatgtg ttatgattc gttaaaggat aaattgaaag gattcttaaa gcaacaaagg     47460
tttggtcctg cattgatgca tattaagtaa agtagagctc ctcagttggc attcccaggc    47520
tgggtgacac agaggtgcct ctttctgata ctctccttcc cagctcctgt gccatcccct    47580
cccctctccc cttctctctc ctctctcccc ttcttctcct gtaatacttc tgctacttgc    47640
tctgttctac ccagagactg aaggaagtga gtggtgatct aattgagact gaataagtcc    47700
gaacatttat tttccttccc cttcactcca tccaaagtcc aatcctgagg aagacatgga    47760
ggttatgatt aaacttgccc aacactcaaa ctttactgac tgcttattct tatgttaatc    47820
acttggcctt tgctagatta atgactgagt gaccagaagt ctcaatgatc ccataaatcg    47880
tatgatttta aactatttgt gtagcttttg ctagttgtaa taaaaatttt cacatgattt    47940
tttttccaaa tagagaggtt taataaagct aatgtgcttg accaggtttt ggagagttta    48000
catactaatt tcttaacccc tttctaatat ggttagtata gctctgtgtt ttcatcagag    48060
agaagcagac tgtgaattcc tcaccttggg gcttccattc tccctccagg tggcctcacc    48120
tttcaggtga acaacctgac ctctctggct cctaaatccc accctaacaa gccgcaggag    48180
ccggtgcatg ggggcatagt ttcttacctt tacctttttc aaacctttcc ctcctcacca    48240 gcttttttttt aagactttat tttcttagag cagtttttaga gcaaatttgc tgtacctact   48300
gtggcaaagt caatacaaat ataaatattt acttaaaacc caagaaccag tacccaaaag    48360
caaaattatc taaagcaaaa ttgagaggaa ggtacagaga tttcccacat accccttgtc    48420
```

```
cctatcccca cacgcgcata gcctctccca tgatcaatat cccccaccag agtggtacat  48480
ttgttacaac taataaacct acactgaagt aggggtttgg acaaatgtat aatgacattg  48540
tagtatcata cagaggagtt tcactgccct aaatacccta tgtgccatct tttcatcctt  48600
ccctcctcac tagcctttgg caaccactga tcttttatt gtctccataa tttcgcctgt  48660
ttcaaaatgt catatgcttg gactcatata gtatagcctt ttcagattgg cttcttttac  48720
ttagtaatat gcatttaagt ttcctccatg tatcttcatg gcttgataga tcatttcttt  48780
tcaacactga ctcgtattcc attgtctgag tgtaccacag gttatttatc ccctcaccta  48840
ctgaaggacc tcttggttcc tttcaagttt tggcaatgat aaataaaaat gtaaatagct  48900
gtataatttt tatatggacg taagttttca gtttattttg ttaaataaca aggagcttgt  48960
ttgctggatc atatggcaag agtaggttta gttttgtaag acacttgcaa actgctttcc  49020
aaattggcca ttttgcattc ccaccagcaa tgaatgagag ttcctgttgc tccacatcct  49080
cgccagtatt tggtgttgtc agtgttctga attttgcca ttctaatagg aatgcattga  49140
tatctcattg ttgttttaat ttgcctttcc ctgatgacat atgatgtgac atatgatgac  49200
atcttttcat atgcttattt gccctctgtt tatcttcttt ggtgaaatgc ctgctgtttc  49260
catcttttgt ccattttta attgagttgt ttattttctt attgttgggt tttcagaatt  49320 cttttctgtat tttggataac tctttcatca gacatgtctt ttgcaaacat tttctccaag  49380
tctgtggctt acctttcat tctccttgatc cctccagctt tttatttaga aaattttcag  49440
tcctatagaa aaaatacaa aaatagtaaa ataagcactc acacattatt catatacatc  49500
caccagttgt taatatttg ccacatttgc tttatctctc tcatgagctc catctgttga  49560
ttttactgaa ccattagaag tgataaatgg catgtcacat catcccaaaa aacaccaata  49620
tgcatctcct aagcatgact tcttactgcc taatcatgac acatcattat taaactaaaa  49680
ataataactc agtaatatcc aacaacatac tgcatttta aagttctcca gtagttccca  49740
gaatcaaatc aagcaaggct cacccatcgt ctacagtctc acaatctagg acagttcccc  49800
tgcctttttt tggcattgac cgattcatat tgaaccaatt ttatgtcatt ggttgattcc  49860
taatgaacca tttccttgtc tacaagctct tggcttgccc tcttacagtg atgagttgga  49920
gtctctccat gacagcacca gactggaaat tcttaacatg ctttccaggc tcattaacat  49980
tgagatagtc aaaatctaca cgatgtcctc aataattttg agaacaggcc atgaaagaaa  50040
atgttgtgaa aaatgtgttt atggttaatg attcaacaca gttaacagag gtgacttggc  50100
tttctgccct gccctcatgg caacatgcgg cttcccagtt cagcactgtc ctctgctgtt  50160
agggcctggg aattctgaat gagattcagt ccttggagtt gaaaaagtaa tttacctgat  50220
gcttggtggt gtgaatgttt gtgacagttt ttgtgctaat acattttgaa ggacatgttc  50280
tctcaaaata gccccttcca ctttctgaat ccacactcca gttttctttt aacttcagt  50340 gagtggtagt ctatttgacc tgatgtgcag atcttctggc atacatttt ctgctgtctc  50400 ttggcataac aaattggcag tctatcccta tgttatgtac actgtttata ttgaaaattt  50460
gtctttaatt ggtctgatac tacatcatct gctagggcca gtagtttgtc atcagccaat  50520
ttgtacacct gaggccctca acaaacacg tgcttacaat gtttctggca ctatttttaa  50580
agcttgtaag aattaaatga gatagcacaa caaccccatg agggtaagta ccgttaatcc  50640
cataatatgg atgaggaaac tgattcattt agagggatta agcaatttgc ccaataccac  50700
atggctagta agtgacagag ctgggtttta gctctgacac tttgattctg gaacctgcac  50760
atttcatcat tatgtcagat gccctgaaga ggatactgta tatcatctca tctcacatgc  50820
```

```
tgtgttcagg caggtgacgt gctgctcaat gctggttttg atgtctttac taaactactg   50880 atctatttt  gagatttaaa tctcaaaaca gtgatactag tgagaagtag tccacctttg   50940
ttaatccacc aaatgttccg gttagggaac ctaattttgg taacttcaag gcctctcctg   51000
ctattgggag ctaagcatcc ttcactctgg actctcactt gcttcacttt agaatgagag   51060
cttttagggg taaaactcag gaagtaggat gactgaaaga aaagcctttc ttctccacag   51120
tagcttatgg ggaaactagt aaattaattg ccattattcc ttgccactaa aggatgagtt   51180
cttatggtag caataaatag acaatagggc tgtgcagacc tccaacaaac tgtcttttct   51240
ggggtcaaaa ggggtctgaa ttaacctctt cttaaattac agctctgtga cacctgcagg   51300
cactcataac aaataagaac accaggccag gcacagtggc tcatgcccgt aatcctaaca   51360
tcttgggagg ctgaggtggg tggattgctt gagctcagga tttcaagacc agcctagaca   51420
gcatggcaaa accccatctc tacaaaaaaa aaaaaaaaat acacaaatta gccaggcgta   51480
gtggtccatg cttgtagtcc cagatactca ggaggctgag gtggctgact tgagccctgg   51540
gaggtcaagg ctatagtgag ccatgattgc accactgcat tcctgcctgg ctgacggagt   51600
gagaccaata gggcagcaag aaacaaaacc tcaacactga accggaatgt ccatgacata   51660
ctgtaaaaaa agaaacctca aatggacaat aactgtatag tgctagttgt aatgattgtg   51720
cctttttttt tttttttttt tgaaacggag tctcgctctg tcacccagac tggagtgcaa   51780
tggcacgatc tccactcact gcaacctctg cttcccgggt tcaagcgatt ctcctgccca   51840
agcctcctga gtagctggga ttacaggcac acaccaccac gcccggctaa ttttttgtaa   51900
ctttagtaga gacgaggttt ccccatattg gccaggctgc tctggaactc ctgaccttgt   51960
gatctgccca ccttggccaa gaatctctt  taagtattca tttgtacttt aaggtaatgc   52020
tcgatctcgc tcttagtaca gctgaattgt ccttcaaaaa gatgatctgg ttatgtttga   52080
cctcttcctc aagggaccaa aaagggaagt tctcagcttt ttatagtatg aggtccctag   52140
aggttttcac tttgggggatt taaaaacaag tttcctgtag ctatatggag gaaaaaaaaa   52200
aaaaaaccta aagggaaaca tggaagaatt ataatgattg gggcatgata attatgtcca   52260 gttttttaaaa ctccattctt aaaaatgtct tataatttat aggttaaaaa tttaaatgtt   52320
tagaggaagc aggacaggtt tatgagtctc tgacctggga atggagtggg aggaatagag   52380
aaggtggggt tgcaagagga gaaaggcaga ggaatttcct accgtcttcc tgttttttgt   52440
tgatggttag tgattaatga gacaagctgt tctgtttctc tgggagtctt gactgtcttg   52500
aagaaaaaaa agaaaattta ttgcaaccca atgcagcttc agattttttcc tctatttttt   52560 ttttttcaatt aaaaacgtaa ctgtccctaa tttaggaact gaaattccca aacctcccca   52620
ttcacctatt caggaagaaa tgaaatggaa cctaacatct acatttcttg ggtataatat   52680 caaaactta  atactatggg gatgaacatg taagcaaatg caactctatc tccccataat   52740
gttggaagaa tctaacttga aaccagacat tggtttgga tcttggcact ttcttgcatg    52800
gaaatattcc aagaaggtgc attgactctt gatttgatct agaaaactgg gttctttcca   52860
gagcccaccc aggatggcac ctcatagact aactatggac ttttccatca atactggaaa   52920
acagtttcat ctaatccccg gaccaaaggt gactcggact ccaagtgagc ttcctcaggt   52980
ttgtttgtta atttatccaa tcatccattc actcagcaaa catttatcaa tcatttgcta   53040
tgtatatgcc agacactaca ccagattttg caagcacaga gatacaaaat cccttgcttg   53100
caggaaaacc tttggtttca ataaatgata ggagaggggt tgcagggta  ctatctatga   53160
```

```
aagttcaaag gaagcatcta acttagggtg gtagggatg  gggctgagca aaggatcag   53220 gaaggtgttg gatggcagga ggcttttagc tgagccttga aaaggcaagg ggaggttggc   53280
cgctttgatg gggtgggcta aggactatcc atgcagaaga aagagcaggt attaaaggtg   53340
tcaaggcagg gagttacctc ctttgggaac tacacataaa gaagaatggc tagggcctgg   53400
tgtatgggat tggggtggga aacccaaggc aggaagaaga cagatcccaa gaggtctggt   53460
gtgcatgctg agggatcag gtgccatctc aatgccatgg ggagtcattg aaggaaaagc   53520
agttagagcc atgggatcca gttcacatat gatcaatcac ccaaacaaag gaaagtttac   53580
tcaacaacat gttttcattt ggacttcatt ttgtcaaagc atgaaagtga tgtcagaaat   53640
agaaatgagt gtattcatgg cacaccacca cacccagcta atttttgtac tttttgcaga   53700
gaactcctga cctcaaatga tccacctgcc tcggcctccc aaagtgctgg gattacaggc   53760
gtgagccact gtgtctggcc taaaacacat tttctaagat ttctttactt ctgggccacc   53820
tccacaaaat tttatggttc tgggaacccc tatctgaaaa agcacaggta tcagcaataa   53880
gtataatgaa cactcactag agggaaagtc attttggttt gggttggtta tggaagcagt   53940
gtcatatgaa aagggctgga ctgtactgca gaaatagaag acccacaaat tgctatggct   54000
tataacagaa aaataaagat ttagatgtca ctcatatgtc cattattgaa cagttgtgac   54060
tctgctccct gtcaccttcc ctccaggacc gaagctgaca gagcaccctc tatccaatca   54120
ttgcctgtct tatgtcagag ggaaaggaga tggcaaatca tgcatcagcc cttaaagctc   54180
tgcccagaag tggtacatta ccatttctgc ccacatttca ctggccagag caggtcacat   54240
gatatgcctg agttcattag ggcaccagat gttgggcaac caataataca acccaccact   54300
gaggtcttta ctaagaagat gacctgggcc ttagggaatg gccatgattt acctggtaga   54360
cacagcaggg gagcaaaagg aaaatatgac aatatttta tgaaatcaag acttggccac   54420
atgaaacttt tttttttttt ttttttttg agactgagtc tcgctctgtc acccaggctg   54480
gagtgcagcg gtgcgatctc ggcttactgc aacctccact tcccaggttc aagtgattct   54540
catgcctcag cctcccaagt agctgggatt acacgcacca ccatgcccag ctaatttttg   54600 tattttagt ggtgacagtt tcactgtgtt agccaggctg gtctcaaact cctgaccaca   54660
agtgatctgc cctcctcagt cttccaaagt gctgggatta caggcatgag ccaccacacc   54720
tggccgtgac acccttagaa aactaacttc aaggcagaat gcttcacagt gacaaatctt   54780
aggatgccac tttatagaaa tattctgaag agagaaaaac ccaggtgagt cagagcagcc   54840
tgggaaaact tcttagaacc aggattttgt ggaattcaga ggattttaaa aggcagaaaa   54900
tccaatgaag ccatttaag ctaaaacaat gtaaataagg tggggctgtg cctagggtac   54960
tagggtgcag aaaggaacct gcctcctgtg ggcgcatttg tgttagcagg tagtgggaaa   55020
ttcgggtgga gggcaggtga tggaggaccc tgaacaccga gggaagactc tggatgttat   55080
gtgccaatat ttatcaagaa aacgcagtcc tggagataca ccaataattt ttgaaatgtt   55140
acagtagata ctaattgaaa cctacagtgc gccaggcacc gttaggttag cagtgaacaa   55200
aaccagcaac ctaaacaaaa tggtgaacac accaggcagt gcccttgtgg gttacatttt   55260
ggtgagacag atagtatata gataaacaaa tatacaatct caaagagtga aaagttgtg   55320 aagaaagatg acacaggatt agagagtgac tagggtgtat atggtggcag tggtggtggt   55380
ggtgcagcca aggggtgggg tggaggacaa gacagctgtg aagactggtg agcatgaggt   55440
agtccctggt aacaaccagc gctccacacc ctaccctcag agtgccattg cagggttagc   55500
atactccact gagtaaagct tccttgtcca ggcaatcagt tagaagagcc aggaatgctg   55560
```

```
ggcccaaaga ggttggccag agagaaaagt gcagggaca tggttcccag atccacgcag   55620
aaccccgggg gaccactgag ttccacaacc tcaacaaggc ccagggttat actaacacag   55680
caggtggcct cattttagac cccacaccag aatctgtgca acgggaaatt ccagtgcagc   55740
agaagttgga gtcaaatgcc tgcctatttc tcattccatt tgggaagcc taaacaggga   55800 agccttctgt gttcctctca ttcccatatt aaactgaact gcaaaactca tggctctaag   55860
tagactttag aattgaccta ggcagaagaa atagcccagc cccttcatta cttcagagca   55920
gaatagagca cttactctta tcacagcagc acaagacccc tgggacacct gactccctga   55980
gacccttcct tgacaggttc ccctgtccat aaacaaagtc aggaattccc agcccactac   56040
acagaatatg acagttaagc ttcattggga tcctgtggct gacctggggc aggctagagg   56100
gcatcacatc tgtacaggct ctcagctttg cgagttcaga aacagactgg gtgttcatgt   56160
ggactggccc aaacctgaaa ctctacagaa atcgcagtgc atgccaggtg gtttgccatg   56220
aaaaaaggtg tgtgtcccag agacagggtg tgtatggtac aaatggattt tgtccacgtc   56280
tttccttccc ttgccagtcc agccacccta ctgtcttttt ttttttttgt cagtttttgt   56340 tttttttaa tttaagttct gggatacgtg tgcagagcat gcaggttcgt tacataggta   56400
tacatgtgcc atggtggttt gctgcacctt atcaacctgt catctaggtt ttaagccctg   56460
catgcattag gtatttgtcc taatgctctc cctccccttg cccccaaccc tccaacaggc   56520
ccaggtgtgt gatgttcccc tccctgtgtc catgtgttct cattgttgaa ctcccactta   56580
tgagtgagaa cgtgcttacc ctactttctt ttcggtttgt tttttgttt gttttgagac   56640 gagttttgct tttgttgccc aggctgaagt gcaatggtgc aacctccgcc tcctgggttc   56700
aagggattct tcagcctcag cctcccgaat agctgggatt acaggcatgt accaccacgc   56760
ccagctaatt ttgtattttt agtagagaca gggtttcgcg atgttaggca ggctggtctc   56820
aaactcccaa cctcaggtga tccgcctgcc ttggcctccc aaagtgctgg gattacaggt   56880
gtgagccacc acgcccggcc tacctaccct actttcttag cctatttgct gactagcatt   56940
caaactgagt gcagggagaa cacctagcag cctgatccca gaagtgcagc tactccacat   57000
tccacagctc tggggcagag tgactaaggc tcacctgtag tccttaaatg gagagcaatt   57060
tgggatgtac cagctaatca aataaaacca aggcagcaaa caatagccat cacttctcaa   57120
accatcctca ttgtgcccct cgactccctc cttccatttc cagttctccc cagaggggag   57180
acagacaata acctcaacaa cagaagccag tacacagcaa gcttgcttca cacgttcacg   57240
tttcttttgt ttttctttga tgttttttct ttgatgtttt ccatttcca tctctgaggt   57300 gattagcagt acagcatagt ggttaagaac agagcaggga ctccacggat agactaccca   57360
gtcttgtcct ttgttacagt ggttcttaag ctttcaggtg actgggaatc acctggagag   57420
cttattaaaa cgtagatttc cagccgcgtg aagtggctca cgcctgtaat cccagcactt   57480
tgggaggcca aggtgggcag atcacttgag gtcaggagtt cgagaccagc ctggccaaca   57540
tggctaaacc ccatctctac taaaaataca aacatgagtt ggccgtggtg gcacacatct   57600
gtagtcccag ctactctgga gactgagaca tgagagtcgt ttgaaccag gaagtggagg   57660 ctgcagtgag ccgcgattac tctaatgcac tccagcctgg gggacaaaac aacaaagcga   57720
gactctgcct caaaaaaaaa cccaaaaaaa caaaacaaca cagattactg ctccccaacc   57780
ccagagtttc tcattcagca catccaggat ggaaacaaag gatgtgcagt tctaactagt   57840
tcccaggtga tactgatact cttggtacca tgaccacact ttgagaacct ctgccttatg   57900
```

```
aagtttccaa agactgttga cttgtgtgtg aaaggataac cctataccta ccacttgtgg    57960
ctattagggt taaatgagtg aatatacgta aaatgctttg agctgtgaat aataaaatgc    58020
aagcatagct agtctggaaa cttcgcccat gccttttgtc tctgttttgt ttgttaacct    58080
ccatttgttt tgtttgtaat aaaccactta gccaggtacc tcttcctctc cttcaaatac    58140
agagggcgtg tgaactttgg agaatgagtg tttaaactga cctaaataat atgtgatttt    58200
caactcttct gtggattcac tcattattca atgtgggctt tgcgtgccat atgtgataaa    58260
cttcttgtgt gtggggtata gtgggaatgt gcatacgtga aattgatgtc agatctttgg    58320
atcgttgtta gggaagataa aaggaactca cactacagtg cagccttgcc agtagggctg    58380
ttattcccac ttacgtggaa gaaactgaaa ctcagttcat tgaggaaact ctctcaagct    58440
tggacttagg tcagaggtga cttgtaagga tacacacaga gaaacatcca agcctgggaa    58500
accagctgat ctattactct gtgtaccaga actttatgta tcagaccaaa cacacaacaa    58560
gcctcacgaa aaactggaat gtgcttcaca tcactgcagc tttgtcccaa tgactgggcc    58620
acccaaggtc tctgcttctc cctaggcatg tcccattgag actctccaca tagagatagt    58680
ctgatggagt tgtgacatta acacccaatg tggaatgtcc cggtggggtg gcctcggatt    58740
cagttgtctt gttctgtaat cagtcatagc caggaagaaa gcccagtctt gctccaggag    58800
caaaccgtag cagcatgctg ctgaaagaac tgcctgggga cttttttcccc agagtggggt    58860 tggctttggc ctgtctagta cttttcaggga cattgaggca gccttagatc ctcagaagag    58920
cacagatctt tggaatcaga cagacttgga tttgaaccct gtttctgcca cttaagtttc    58980
ctcaactatg cattgtggct atcacacacc tcacaggtgt gaagatcaaa taacataaag    59040
tgcttagcag agtgcctggc acatagtatc tgcacttaat gaatgatagg gtttggtttt    59100
ttttttttta aattaaaaaa actggaaaga tggaaaggtg aaaataatta ctcagcttta    59160
tcatcctatc atttagcctc ttatccctga cagtgtgcca ttttcaatcc tgtagggatg    59220
cattcattat tattaatttt ttaagagaca ggtcttgctg tgtcccaggc tggagtgcag    59280
tggcacaatc ataattcact gtaacctcaa actcctggga tcaagggatc cttgcacctc    59340
agtctcctga gtgtaaggtt cttgtattgg ttggaaccct gagagcgcgc aacagaaaa    59400 cacgaggcgg tgtgaagcaa catgctgttt taatgagcac ctgggtacag gcaggctgaa    59460
gcctaaaatg gcatcagccc caagtgagga cagggcagag gttttatagt ctcttgtaaa    59520
caggaagtgt cctagtctga cgtaactgct atgttgtacc caggtggcct gtttctcgat    59580 cagggtaca tgtcttcgtc cagggtaggt gtcttcctgc cggctctctt cctgcttctg    59640
ctatcttgct gacacacgct gctgacacaa gtggacttgc gccttgggac tgggcctgag    59700
aagggaggag ttattcatct ccttaagctt tcaggccccg gggagaatct tataccgcgt    59760
agctaggatt acagacacat gccaccacac ccagctaatt tttaaagttt ttgtagagat    59820
ggcatcacac tgtgttgccc aagctggtct caaactcctg gcctcaagta atcctcccac    59880
ctcagcctcc caaagtgctg ggattacagg catgagccac cacacctggc ctcatccatt    59940
atttaattta aggctttata tgctacgaag ctataggttt taatagaaa gtctgtttta    60000 catggttgta attatataat tttgcattct ttttccatac tataaaatat tttaatgtta    60060
taaattctgt acgtaatttt agtgaacatg ctataattta cataaaattc cttatcattg    60120
gacacctaac aatagagaat tgattgaata aatggtagtg cattcatata ataaaatatt    60180
aatcagccat ttaaaaggt ggattagaag tatacttctt aacatataaa catgttcacg    60240
attatgtata aaatgaaatg agtgtaccta aatatcaact acctctcaag tctgtctgga    60300
```

```
cattttccta cctcagtctc agcaactttc aaactttaat gagcctccca atcaccaaag    60360
gaacttgtta aatgccagtt tcacgcttta ccccaagagt ttgactgaga ctggggctca    60420
ggaattggca cttttacaag gatcccaggt gcctctgatg tgggaaagac acctcaccta    60480
tttctgcctg ttgaagctat acttaatttt ccaagcttct ccttcttctt tctcctgaag    60540
tcctgtagta ttttgtagca cttgtctgct ttcttgtctt agagatctta gcaaatgctt    60600
ctaaattgta aaacttttcc tgatcctcca accaaaccta gttatgcacc catgtcacag    60660
ccccagaatt tgtgttaaac cctgtgtgag ttgctgaata taaatactga aatctctgga    60720
atccaaactt catttacttt gtggtggaga gagagtggct gagtacttca gaactctttt    60780
gaacacctgt tatagcagga acttttggga ataaaggtgg tctttctaac cttgatttaa    60840
aacaaaaaca aaaacaaaac cttgtttaga ttacttttac ttacctgaca gtcaggttgt    60900
gaaaagtaaa tagtttgtcc tttgtgcatt tgctctggtc taggccagag atagccagta    60960
agctggagag ggcagttaaa acccttcaag aggcctgtca ttccaaagaa tagttttctt    61020
caggtctgtt ggttggtttt cattctcaga ctgtgtcact gaggttgttc aaggtaagat    61080
tcttatcttg cagttcactt agggaccact tatgctaaaa ttgagactga gttactcatc    61140
aaagtacttc ttcacttaga ttttatcag tgtgatttcc ctccttcttt aaataatatt    61200
ggatatccat atcaagtcag gtttatgtca tcttacatta tctttatgt aataggccag    61260 cttgcagatg catagttata aataactatt gataaatatt atattgagat gacactgaaa    61320
ttttgtcctt gcttgtaaga gaactagatc atattctgta taattagtta acacaaaaga    61380
attcctcaga aacaaacttt aaaagccagg tataacagct cactcatgaa aagttccttg    61440
tttcatatga aaatggtaac tttgtagaag taaagctcca gacaacaaag aattgacagg    61500
gttggggaat ggaaggttaa tgaaattggt taatcaaatg cttctgatgg ggaatcacca    61560
catgtagtgt acttgtccac atggcaaact cggaatcact cttcagaacc ttgtgtagag    61620
gcatcatcta taaaccctg catctgtaag gctttttcat cagccccctc cttggaaaaa    61680
atttcttttt ttattctatg cccacaacag tacactacac acacatctat catatgtcac    61740
actctagtat atgcttgtgt gttactatta tccaatagat cagaaaattca ttgggcatag    61800 agcatgtggc ttatttgtgc aatctgaccc aggttcagtg cctggatata gtagtattca    61860
ttaaatagat gtatgaataa gaattctgca ctgaacaggg tacataaatc atataaactg    61920
cattttgtgg gtgttttctg agaactcctg cagttaaatt taaagcatca ccttatgaca    61980
aatttccata aaatattgtt ataataaatt atgaataaat gttgaaaata acaagcccag    62040
tatctgctgt tccctgagtc cctgatggca actgcatgct ccccagtctg tgggactcct    62100
gatttaaaga gctagatctg aacttctgca gaaacctgct caacatttgc ccattggttg    62160
ctgtgaaatt cctctcctgg gctcttaaat tccacagagg cttaattatt acagatattt    62220
aaactttgta catacatgac ggatatcaaa catacccaca tctctaaggt aaactgtatt    62280
aaaagtgcca gacaattta aaattgaaag ggacttcgtc atttttactg gttaggaaac    62340
caagcctctt aagagacaag cagttttttgt tagtgggagg agcactagaa ttgaagtcaa    62400
atagaccaga gttcagttct tggctcaggg gctcaaatca cagcctctga tcggcagtgt    62460
gatcataagc ccttcactta atatttttga agatcagttt tttcatttgt aaagtttggt    62520
taataatccg tctcagtggg tcacaacaag ggattacttg agattacctg agccagagca    62580
gcacacataa tatctgcaca aagcaaatcc tcagtgagct tttgtctctg ccctttcttg    62640
```

```
cccagatcac acagagctaa gacttagacg cttctttggt gttgtggttc ccagttcacc    62700
tgacaggact cacacatatc aaggatgctc ccaaggggct gtgtcacatc agcatttaaa    62760
tacagaattc aggatctcct gctttaaaaa caatctccct tctgagttac tctttttaaa    62820
ttttatttat ttatttattt attttgaga cggagtctcg ctctgtcgcc agggctggaa     62880
tgcagtggcg cgatcttggc tcactgcaag ctccgcctcc ggggttcaca ccattctcct    62940
gcctcagcct cccgagtagc tgggactaca ggcgcccgcc accacgcccg gctaatttt    63000 tgtatattta gtagagacgg gatttcactg tgttagccag gatggtctcg atctcctgac    63060
ctcgtgatct gcccgcctcg gcctcctaga gtgctgggat tacaggcgtg agccaccgtg    63120
cctggccctg agttactttt attgctgttg tttttttttc ttttccttgta ctgcgagtta    63180 tgacaccctc ccagtcaacc atcaactata atttaacttt atataattgt gtgaattagc    63240
aagatcctag gaggctccag gatctcaaag gctccaggat ctcagggtaa tgtatataca    63300
cattttagaa gagtaagatc tacatcgcct aataagtctt cagcttttaa aaatcacatt    63360
ctaaaataat aagtgaaata tttgtgctga attgaaaggg tttccataaa ttctgacggt    63420
aaacgatgag tgttttaagc atggagatgt tagtcataca aacttaagtc accatgaaac    63480
aggcgatcaa gtgggggaag cagcatcctg tttcctagtc ttaccagagt tcatttgtca    63540
ttttaagaga caacttactt ttccatcttt tcttcttttc ctgtaaaggt agaaacctgt    63600
gggttcttgt tgtggggcgg tttccaaagg aacacagaat tgggattcca gagttcaaat    63660
acgtggcaaa tatgcatgga gatgaggtac gtatgtggct tgaatttctg aaatgtcacc    63720
agagaagctt cccctagggt ctcttgagct ctgtataaat gctaccgagg aagcctggag    63780
aagtctccag catgcattgt acaaagaagc aaggcccaga gaggtcttcc tgtgaggcct    63840
gtgggaggtt aaggaatcag ggtccaacaa ccaccacagc tgtatggttg tgtacccagc    63900
accctgtcag agtagctgga gcttgttttg tgtttgggc cggaagaaca acagttcccc    63960
agccctgaac ttctgccagc caatccctgc atctcctttc tgggttaagt ttccccacct    64020
cctggtcagc atgaaggtga cccagcaaag gagctgtatt gtatccgaac ccacaaccat    64080
cagaaactcc caaatagcta cccaaattcc tgagatctgg cttttcaaat gcttttgtta    64140
ctctctctta aatctaacac tcattgtctt cagtgctcca gtttagacaa tcacacttat    64200
gattctctcc tactcaccat tcaacaaaca cttggctggg tgcagtggct cacacctata    64260
atcccagcaa tttgggaggc caaggcaggt agatcacttg aggtcagtag ttcaagacca    64320
gcctggccaa catggtgaaa ccttgtctct actaaaaatg caaaaaatta gccaggtgtg    64380
gtggcgcata cctgtaatct cagctagtcg ggaggctgag gcaggagaat tgcttgaacc    64440
caggaggtgg aggctgcagt gagccaagat cgtgccactg ctctccagcc taggcgacac    64500
agtgagactc catctaaaaa aacaaaacaa aacacaattt taaattcctt aataatatct    64560
tgcctctttt ccaacttagc agggataaac tctcctttta tttttaggtt ctacaaaata    64620
ccatttacca ctgttaccta cccagccatt cttgccaggc agttgaagat gttcacctct    64680
gtttctcacc ttgcttcctc agaatatttt gagaccatga caactgaaat attttctgtt    64740
taccaggact ctataaaact gagcgatcaa agagtcccca gccatcccag taaggaaact    64800
ttgcacagga atgtgggtat taccctgtaa aacacaactt ataactttag ggactttctc    64860
atttacatac atattccaat aagtactacc tgctgacttg ttaaaacact tctggatttg    64920
caatagtatg ggtggcatgc tctaatcagt gctgagcttc ctgttctggc ttaagccctc    64980
cccaaactct ataggaactg gatctaccct tcatggtaca ctccgcctgc ccttgccagg    65040
```

| | | | | | |
|---|---|---|---|---|---|
| catgctgccc | aacctgtcct | gctgagagag | gatacttctt | gcagctgcag | ctaagatgca | 65100 |
| agcacctgcc | cctagcaaag | gaataagttt | ttgaacccga | ttttggggtg | ggtgcaagtt | 65160 |
| tagcccatct | gtgactttt | gagcatcacg | ggcggcttct | ttaaaaaaga | ctacgttgca | 65220 |
| aggagtctga | ccaaagttag | ttttaataaa | acaactgttc | gttatagaca | gcagctcaga | 65280 |
| ctgcgtttcc | cttttgctat | cttgtctatt | gatcgaggtc | ccttgatcaa | ggtccctcag | 65340 |
| aatgctttt | ttttttttt | ttttttccg | atggaatttc | gctcttgtct | cccaggctgg | 65400 |
| agtgcaatgg | catgatctcg | gctcactgca | acctccgcct | acaaggttca | agcaattctc | 65460 |
| ctgcctccgc | ctcctgagta | gttgggacta | caggcatgca | ccactatgcc | cagctaattt | 65520 |
| tttttgtat | tttttttt | tttagtaga | gatggggtt | tcaccattt | ggccaagctg | 65580 |
| gtctcgaacc | cctgacctca | ggtgatccgc | ccgcctcagc | ctcccaaagt | gctgggatta | 65640 |
| caggtgtgag | ccaccgcgcc | tgactcagaa | tgcatttgta | acaagagaca | tatggcattc | 65700 |
| attgtcttta | gtagttttt | tattgctggc | atttcagagg | ttccagctat | ctactcagaa | 65760 |
| attagtcctc | agaactgaaa | ctcccaaaga | taagcaagag | tcctttccgt | cccctacccc | 65820 |
| cgaatttgtt | tattctttcc | atgcactttc | ctaaatttct | ggcatcttgt | tgtctggtgt | 65880 |
| atcgttcaaa | tcagggctcg | ctagtgcgct | ctgattcttt | gagaaatgct | gagggctgag | 65940 |
| actaggcagc | ggggaaaagt | cccagtgtat | tttggggtgg | gaatctgaag | cacttttacc | 66000 |
| cccttatgtg | acccagctcg | tggcaatgtc | tgggggctct | atgggctag | taagaaattt | 66060 |
| attattctga | atttgagacc | ttatctattc | tgtcctcccc | atgccgctag | gagctgaaga | 66120 |
| aagtgatggc | ttaacattgg | agcagagaag | tccttctgaa | tacaggatat | aacaaccccc | 66180 |
| tttttcctcc | catagatctt | ttgaaattga | aagcattttt | aagaagcaac | agagctaaca | 66240 |
| ttttagggca | gtgattctta | accttttttg | gtgtattcct | tgctattctg | ttataaattt | 66300 |
| gacctgactt | cagggtctgt | ggattaccta | ggagtttatg | gaccttaggt | ggagaatccc | 66360 |
| agcagggaac | acatacacac | tgagtggcag | ggtggacaga | attggccaca | ctatttttaa | 66420 |
| aatgggaccc | cacccccact | gtgcgtgtgt | gtgtgtttgt | gtgtgtgttt | ccacacttaa | 66480 |
| tactatggct | agatgacagg | aagcatcagc | tgcatcaggg | agactcagct | ctgctgatta | 66540 |
| cacctgccat | ttccccccat | gtatttttat | tttacttatt | tatgccttgt | tttagaattg | 66600 |
| ggtcttttt | taaattagaa | attgtctggt | ggccaaaaag | catatgaaaa | agtgtctaac | 66660 |
| aacactaatg | atcagagaaa | tgcaaatcaa | aaaccacaat | gagatatcat | ctcataccag | 66720 |
| tcagaatggc | tattaataaa | aagtcaaaaa | ataacagatg | ctgatgaggc | tgcagagaaa | 66780 |
| aaggatcact | tacacactgc | tggtgagaat | gtaaattagt | tcatccactg | tggaaagcag | 66840 |
| tgtggtgatt | tctcaaagaa | cttgaaacag | aactacgatt | caacccagca | atcccaatat | 66900 |
| atacccaaag | gaatataaat | tggtctgcca | taaagacaca | ttcacacgta | tgttcattgc | 66960 |
| agcgctattc | acaatagcaa | agacataggg | ttagtctaga | tgcccaccaa | tggtagactg | 67020 |
| ggtaaagaaa | acatggtaca | tatacatcgt | ggaatactat | gcagccatga | aaaagaaca | 67080 |
| agatcatgca | cttgcttata | gaacaagatc | tataagcaaa | ctaaacagaa | aatcaaaaac | 67140 |
| cacatgttct | cacttataag | tgggaactaa | acattggata | cacatgggca | caagaaggg | 67200 |
| aacaatagct | accagcatct | acttgaggat | ggagggtggg | aggatggtga | ggataaaaac | 67260 |
| ctacctgtta | gatactatgc | ttattaactg | ggtgatgaaa | taatccatac | accaaatccc | 67320 |
| cacaacacac | aatttaccta | tagaaccaat | ctgcacttgt | accctgcac | ttgtaacatt | 67380 |

```
tacctataga accaatctgc acttgtaaca tttattttta aaataaatgt taaaaaaaaa   67440
aaaaaaaaaa aaagcaggcc gggcgtggtg gctcacgcct gtaatcccag cattttggga   67500
ggctgaggtg ggtggatcac ctgagtttag gagttcaaga ccagcctggc caacatggtg   67560 aaacccatc tctactaaaa atacaaaaaa ttagctgggt gcagttgtgg gtgcctgtaa    67620
tcccagctac ttggtaggct aaggcaggag aatcacttga acccagaagg cagaggttgc   67680
agtgagccaa gatcatgcca ctgcactcca gcctgggcga cagagtgaga ctgtctcaaa   67740
aaaaaaaaaa gaaaaaaaaa ttattacaaa atcaacatat gttcatgtta gaaaaagtat   67800
aaacaaaaca ttatatactg accttcccaa aattagtgct cttaatttct tatttgtttt   67860
tccagatatt tgtgtgtgca tgtacttttac ccaaaagaga tatgctattt gcaacacttt   67920
taagtaaata ctagctacct ttttgtacca ataaatcttt atcctatctt tatcttatcc   67980
cccactttct agtttctcca attgtcctca aatgtctcta aaattaccca aatcaggatc   68040
cagtcctggc tcatgcatcg catttagtgg atatgttgga tctcttggat ctcatttaat   68100
ccagtatctt tttattatga tactaggctt gataaagagc ccaatcagtt gtctgccctg   68160
tagaatgcca catattctgg attttttggtt tgcttcttta tagtatcact gcagttgtac   68220
ctctagtccc tgactttact tcaaactgga aattaaatct aaaggtttgt tgaatttaat   68280
gtggctaata cacatcttag gagttgtgac gataggttca tttgattgat gctgagggtt   68340
caggctaatt caccctggcta cactcaggaa tgccaaaagc aaactccggg tagcaaaatc   68400
aacttaaaat ggcccatttt cagccaagta ttgttacaaa ataagtaaag ttaaactcac   68460
tcctcatttt gcatgaattt cacgtattct cttattcttg caaaggtcat tgttctacta   68520
ggatcatggc tcatactgta gatattttc ttgtcttcag tgaccttcca ttgtctcaca    68580
tgctttctat ggcacaggct cactatgcca cattaatcag gctggcaagt tgcctcctca   68640
aacagtgctt tacaagaaaa taataacaat agctaacatt tatggagcac agatgacaat   68700
aagtgcattt taggcctcgt ttcttttggat cacctctgca gaaggcatgt ttattagtcc   68760
catgtaccat gaagggggcc caggtttatg cttggtcacc agctgtggga acccggagcc   68820
tgaacaccaa gctttgccca gctgtggatc cactccttta ctctctcttc tctgttttta   68880
aaatgttctg ttttatggtt ttcattctta agtatagatc tatgatctat ctcaaattaa   68940
tttcactggg atggatacta agttgttgca gcaccatttg gtgagaggat ttgggcttgc   69000
tgttatgtaa aagagtaaca agctcttgga gggcaacact ggaataagta tcttccagtc   69060
acctacctgt ccctttcttt cccctactct tcacttctct ctccttgact gctgggggagc  69120 tgacagacat agcactcgtg gtgagccttt gtcaccgatg tttattcatt ttttggagca   69180
gcatgggaga acatttctg gggttctttc tcattttaat aagactagta ggtgttttc    69240 tggttcatcc aggcacacac attatttgca cacatattgg catgttggat tgaagcctca   69300
attctaggtt taatttacgc aagctcctaa ttggcatcac ttggcatacc tacagttgaa   69360 tcttttttt ttaattggaa gggttgatgc cagtgcaggc tgaatgggggt tctctgccat   69420 tcctgtatgc tacagatatt cagattgcct gggaacagga tccttgtccc ctcaccttcc   69480
cccatcacct cattctgctc ctggcttggt gtgtagtaaa ctataaccaa tactctaaaa   69540
tcagagctat actgaaaact gggaccatgc cctgaaacca ggagcatcta acatcctcag   69600
cctaaatgtg gatgcagaag agaagcctgg gaaaatcttc cccagccctc cctactcttt   69660
gttttgtgct tatcttctat cccatgtttt tcaaattttg cagaaaaat acttttcttg    69720 ggtaatctct aggttggtaa gacatcttta attcctgcct aatggaaata ttgaagcaag   69780
```

```
gcatgactgt gtgcttaaag aattgggtgc ccaggccagg catggtggct catacttata   69840
atcccatcac tttgggaggt caagctgggg agattgcttg aggccaggag ttcaagacta   69900
gcctgagaaa catagtaaga ccttgtctct aaaaaaaaat ttaaaaatta gctaggtggg   69960
gtggtgcata cctgtggtcc cagctactca ggaggctgag gtggaaggat tgcttgagcc   70020
tgggaggtcg aggctgcagt gagccatgat cacaccactg tacttcagcc tgggtgacaa   70080
agcaagaccc tgtcttaaaa aaagaattga atgcctagag ttttaagcca accctagtaa   70140
cattaagcaa agtatcatag gtcagagcct gggttcaaac ccaggtttcc ttgacctcag   70200
tgccaagggt cttaaatact gtactgtagg agtaactatt gaatatgctt gtaaaataat   70260
ttaactaaat tgcaattatt ttttatttta gagttgggat ctcgctctgt aacgcaggct   70320
agaatgcatt ggtgtgatca tggctcactg taacctcaaa cacctgggtc caagcaatcc   70380
tcctgcctca gcctcccaca tagctaggtc tagaggtgtg tgccaccaca ccaggctaag   70440
ttttttattt tttgtagaga tggggtccca cagtgttgct cagactgttc tcaaactcct   70500
ggcctcaagc gatcctctgg cttttggcctt ccaaagtgtt gggattacag gcttgagcca   70560
ttgcgcccag cctaaattgc aattctgctt ttttggggag atggggggta ggaattttt   70620 taagccttag tttcttaaag agcaatgaag tattttact aagatagact taatatgggc   70680
ttttgtaact gcccaacagg ttcattttgc ctgttgtcca gatagagcag atttatcaag   70740
acaggggaat tgcgatagag aaagagttta attcatgcaa agccaactaa acaggagacc   70800
ggagttttac tattactcaa gtcagtctcc ccaaaaattc agagactggg agttttaag   70860 gataatttg tgggttgggg gagagacagt ggggagtggt gattggtcag gtcggagacg   70920
aaatcatagg gtgtcaaagc tgtcctcttg tgctgagtca gttcctgggt gggggccaca   70980
agaccagatg agccagttta tcgatgtggg tggtgccagc agatccatcc agtgcagggt   71040
ctaaaaaata tcttaggttt tacaatagtg atattatccc tctgagcaat tggggaggct   71100
tggaatcttg tggcctctgg ctgcataact cctaagccat aatttctaat cttgtggcta   71160
atttgttagt cctacattca ggaaaaggct attatcatct ttgtttcaaa gttaaactat   71220
gaactatgtt agtttagcct atgcccagga atgaacaagg acagcttgaa ggttagacgc   71280
aagatggagt tggtttcatc agatctcttt cattgccata attttctcac tgttatgatt   71340
tttgcaaagg cagtttcact tttgaaaaat tcgcatcaca tttagaattt tatgattgtg   71400
gcattggttt atagtttatt gtattccaga aatataggtt gaaagagaa acattccct   71460 gggtaatagt ggccatattt gtcaacctga aaataaagag ataaaggata aatgactttc   71520
acacaccttc taagtataag agacagttga tgagatgtag tttgcatgtc taaatgtttt   71580 acttagggg tattttaatg gtttacgcag acagtgggac acaatatctg aaattatggc   71640
cgttctggaa aatctgggaa gtacagtcaa catgcagtag aggttcccaa cttatcatta   71700
aaccaaaaca caacattaaa gcttgtcttt ctaaatgccg ctgcccaagc tcctttcct   71760 accactatcc tcaggtgata gtaaaatgtc ctcagtaacg ctctgtggtt tgaataatta   71820
aattctttct ttttagattt aggcagagct cattgtttc caggtgaaat atctaattca   71880
ttttaagcat gttttaaatt aatgaactgt ttggtgacca gatatcccaa gtccctgtca   71940
tgagcgtaat tgttagcctg tgcctctata aaatgtgttc ggtatttaaa aatccttcag   72000
ataaaatagc ttgatcattt gtacatctcc ccttacaaag caccttaagt cctcatgtga   72060
atttcagaaa gttcttcctc aggatagtct tgatcttata atgaattttc aacagtagtt   72120
```

```
tattagcaat tatttattga atacatgata taccaggagc tggacaagct acaccaagaa    72180
cacagggata cagagaaaaa ccgtgaaggt ccctgacttc ggggcttcga tggtggagtt    72240
agagaaaggg aggtcagtca aggtcagcca agtgattgta acgtgtgtga cccgcattag    72300
ataacacagg tgtcatggtg aacccagact tgggaggtca agaaaagtat gctagataaa    72360
tgtcatgttt aggctgatat ttgaagaaga aggattagct aggcaggtca gacaaataac    72420
ttaaatctat aacacacaca ccactgtgga gccccacagc ccgatgactt tcccccagga    72480
agctgcatca cagggtagca tttcaaaaac agattccatt gttaggatag ctgaagattc    72540
tctctctctc tctctctcac acacacacac acacacacac acgcatgc gcgtgcacac    72600 acacacacac cacacaacac tgcctgggtt gtagattgtt ccttcaaaaa ttttttttctg    72660 ttttttttaa taaacattct gtgaagaacc agaacactca tttgtatctg tgtggcaaat    72720
tccaacttga ctgaattgaa ctgcagctga tagagaatgt attttctgct ttctgggtga    72780
ctgccatttt aaccaccgga tgaaggagat ggagtgagag tctccggagg ccggtgtgtc    72840
catcaggccc ccgtttcttc atgagggctt ctccctgaag tctgtgctct cacaggaagg    72900
aagccagcat gctgggtgaa aggctgcctg ggcaattgga gactcttttg accacattct    72960
tttttaaaat ttggactctc cagggtttcc tgtcaaagac ttaattttca atgaagggag    73020
gtttatacat aaaacatgaa tgagtgtttg aaacatttat attaaggttg ggaagaatta    73080
atttgaataa tatttggcat aaatctgctg ttacagaggc aggaaaagat ggcccaaaaa    73140
gaaaggagga ttttgtttaa ctgcctctga aatttcatct gtttatctca gcatttaaaa    73200
aattatctga tgcttagttg gttctttatc ttattttcaa gatttttatt tacccttgca    73260
attgagaact tgtgatttgt tgtggactat tgagacacac aaaaaatact ttggttacat    73320 acttgttttcc ctgaaagaat catgatttta ttattttttgt aaaaatgaca taggttttct    73380 ttaaaagaa taagaggaaa taaaaatcat tcagaatact gtacccagaa atagccatca    73440
ttaatatttg tcagacatca ttgtagacat ctatatattt ctgtagtaag agaatgagag    73500
gaattaaaag aatataaaat aaaatgtctc atatgttata ttgtatgaaa tttttatttta    73560 tttgaattaa cagaagaata aaactgaagt gaaactaaaa taactggtga aattgatgct    73620
ttctcaaaat aagaaattga ttatcacatt tgtctttctt tttttttttt ttttgagaca    73680
gagtctcgct gttgcccagg ctagagtgca gtggtataat ctcggctcac tgcaacctcc    73740
aactcccagg ttcaagcgat tctcctgcct cagcctcccg agtagctggg attacaggca    73800
cctgccacta cacctggcta atttttatgt ttttagtaga gacagggttt caccatgctg    73860
gccaggctcg tctcgaactc cctacctcag gcgatctgcc tgcctcagcc ttccaaagtg    73920 ctggattat aggaatgagc caccgcgccc agcttgatga tcagattttt ctaaagttaa    73980
gaaaaaagat tattaaaaac tttgaaattg tagtcatttt atgtgtatat attttaactt    74040
ttgatagtat tttatgtccc cttactatga aatgtgaagt aattaacact ttgaaaattt    74100
ctccctcaac ttcttttttt tttgaggtgg agtcctgctc tgttgcctag ctggatgga    74160 gtgcaatggc acaatctcgg ctcactgcaa cctctgcttc ccaggttcaa gcgattctcc    74220
tgcctcagcc tcccgagtag ctgggactac aggtgcccac caccatgccc ggctaatttt    74280 tgtatttttta gtagagacga ggttttacca tgttgcccag gctggtctcc aactcctgac    74340
ctcaggtgat ctgcccacct cagcctccca aagtgcttgg attacaggca tgagccaccg    74400
tgcccggcct caactttat attttgttct atacccatac taccaagact gcttaatcta    74460
attctgtatc taacagaata ccaactcaac ctagcctcct aatcatggtt tctttactct    74520
```

```
tccttttcac tttctttcgg ttgggtgaat ttcattgcca actcgtgtcg tgattgtttg   74580
catgctggag agtgtatgat tcagatagct aagagacaaa ttcacattta gagtcacatg   74640
gggattctga tatcacttcc tctctgttct tgacttggga ctcagatagg ccagggattt   74700
ttgccgattg aaccatacta tggcctctaa ccagcattta gacatttaag gaactatggg   74760
actcctggtc acttcctcct caccttcctg tacctattcc tccccaaacc cttctgagaa   74820
agcttcttaa accaacgatc tttttcacat tttttggtt tttttcgag atggtgtgtc   74880 tcactctgtc acccaagctg gtggcgcgat ctcggctcat tgcaacctcc gcctcctagg   74940
ttcaagcgat tcttgtgcct gagcctcctg agtagtgggg attacagtca cctgccacca   75000
tgcccagcta attttgtat ttttagtaga gatgggtttt caccatgttg gccaggctgg   75060
tctcaaactc ctgacttcgg gtgatccacc cacctcggcc tcccaaagtg ctgggattac   75120
aggcttaagc ctccacgccc agccccttt cacatttaaa gttactgtca cagttttatg   75180
ttaccagctc ctccccactg gctttagggg aggtcataag tagctcatca aggttacttc   75240
caaaggtgct ggaccttcaa aaacctatta tatcttaaaa ttggaaccca gtggggtgta   75300
caagtgactt ttttggttat tagcttgtaa ggacttttc cagtgacaat tttgactata   75360
aaaacaaaaa tctggccggg cgcggtggct cacacagtaa tcccggcact tgggaggct   75420 gaggcaggca gatcacctga ggtcaggagt tcgagaccag cctggccaac atggtgaaac   75480
cctgtctcta ctaaaaatat caaaattagc cagacatgct ggtgggcacc tgtaatctca   75540
gctacttggg agggtgaggc aggagaattg cttgaatcca ggagacggag gttgtagtga   75600
gccaacatgg tgccactgca ctctagccct gggtgacaga gtgagactct gtctcaaaaa   75660
aaaggtagtg gaagaggaag ataaaaaatg agtaggaaaa aaagttgaag tcaggattgg   75720
acataatctg actctaaatt ttatggttgc ctatgaatct ataattcata tatcccaaat   75780
tttctttctt tcttttttt tttttttttt gagacagggt ctcactctgt cacccatgct   75840
ggaatgcagt ggtgcgatct cttctcactg ctgcctcaac ctcctgggca gcacaagcga   75900
tcctcctacc tcagcctcct gagtagttgg ggccataggt ctgtgtcacc atgcctggct   75960
aatttcttat tttatgtagt gatgggatct cgctatattg cccaggctgg tctcaaactc   76020
ctgggctccg ccttagcctc ccaaagtgct gagattacag gcatgagcca ctgccaccag   76080
ccccaaattt tcttagtccc aatttcaatt attctgtgtt cattaggata acaaatgttt   76140
aaaatgtggt ctctttatgt gccagtgagg gaatcaagtg agaagtggtc atccaaggac   76200
cgcttatcct ttgtcacaat gttgaagtcc tacagtgaaa tcatgactgg aaattcttct   76260
gaggctccat gaaatctttt cttgcacagt gtctacatga atgtgcctgc agcactctcc   76320
tgattttctc acctgctgcc cctgagttct catttactaa ccctcaaca acatctgttc   76380 ttctgaagca gattccttga acctaaaatg atagggagaa tttgatgtag tctaagcaga   76440
tcttcctatg ataaggctga catttaaatt acttttttta aataagaaaa ataatgactc   76500
tctctcctgg ggagggatta taaagcaagt tctctcacag gccttcagtt tcccaagcct   76560
tattgatact gcaagctaat ttaggtggat atgacagctt ttaacatttt aatagtcatg   76620
cttttactta atatatatta gaaatatata tctagaaaag tgataatgat atgaagtttc   76680
tcaggagttg gaagccagcc ttagcaacat agcaagaccc tgtcttaaaa aaaaaaaaat   76740
ctacaatgtg atgattttaa gtctgttatc caccaataca tacatgataa gcttcatatg   76800
caccatgcat tctcatggaa atacgtgatt cctgtgcttc tctgtaactc aacctcttgc   76860
```

```
tctcccactc cagaagatac tttggaaggc aaccaaatga aaaatgttgt aagaatcatt    76920
attgcggccg ggcgcagtgt ctcatgcctg taatcccagc actttgggtg tctgaggcag    76980
gtggatcact tgaggttagg agttcaagac cagcctggcc aacatagtga aaccccatct    77040
ctactaaaaa tacaagaatt agctgggcgt ggtggcacac gcctgtaatc ccagctactc    77100
aggaagctga ggcaagagaa tcgcttgaac ccaggaggcg gaggttgcaa tgagccaaga    77160
tcgcgccaat gcactccagc ctgggtgacg gagttgagac tgtctcaaaa aaaaaaaaaa    77220 aaaaggaag cagcagcagc agcagcatta ttccactcta attcatttttt gcaatatgta    77280 aactatttac aaataggtac tttcactctt actagcattt ttcagcatac ctcaggactg    77340
atcgccacct gatggccact tggcagagca taagcatgct tgagaaagag tgatcttaca    77400
aactagtttg ggtctgagat atcatgtgta gagacccta ttggggaatt tgtaccgtag    77460
ggagtgcttt ccttattgcc tctgacctaa taatgtcctc ttttctcttt aacacatata    77520
gactgttggg cgggagctgc tgctccatct gattgactat ctcgtaacca gtgatggcaa    77580
agaccctgaa atcacaaatc tgatcaatag tacccggata cacatcatgc cttccatgaa    77640
cccagatgga tttgaagccg tcaaaaagcc tgactgttat tacagcatcg gaaggtaaag    77700
aggggctggt ctatctttac ttgaaaacaa cacaacacaa aggctcccga caggcacctg    77760
ttggccttgg caagaggaga tgtgtcatgg tgagagccct cagagccggt gtcatgtcgc    77820
tgatgtgcca aagctcaagg cacatcaggg ctgcctccgg cttgcaggaa gaaatgcaaa    77880
taaggctact ttgccccggt gcccacctag cctctccatc ttcatttgcc actccttctc    77940
tctcccctgc ctcctcccct ctaggcctcc ttcctggaag taccaggtgc tttcttacct    78000 cagcattta cacacaccgt ttccctgcct aaatagcatt tcctccaaga ctctttctct    78060
cgacctgtca tacactagat cccctgataa actctcacat cacctggcac tttactgtca    78120
gagcacaact tttaatatct aatttcttgc ttcatgtctc tccccccact acactgcaag    78180
ctacctgcag gcaggaatcc tgtccattgt gtttgtcgtt gttagatccg cagtgcctgg    78240
cagagcaccc aggcccttgg taatgaccgg ttgatttatt aggccagtag tccaagaact    78300
aaccataagc aagaacgggt cttgaaggag ctctgattta aacagtttat tttgtttcaa    78360
gctgccttgg gaggtttgga atttctcaga tgtctaatat acattcatat gtatgcaatt    78420
tacatatatg tgtttgcttt accaaagctg aacaaaatct caccacttga ttccctccaa    78480
ttttaagttt ttcaaatata tttaaacatg gctgttccac gtttcacaag tacttctgtg    78540
taatgtgttt agtgttgttt ctgttatcag ttgctactta acgaaccacc ccaaaattag    78600
cgacttaaag caacagcctt tttatttact gttgattcca taggtcagga atttgggcag    78660
ggcagagcag ggatggctac tgtccgtgcc acaggtctgg ggctcagctc tggtctttct    78720
gagacaattt acctggagcc atggactctc cgtggactct ccacgtggcg accattggga    78780
tctcaaggtc ccaaaaggga gcatctaaga gcagaagtcc caaatacaaa cacttatcaa    78840
acctctgcct gcatcacaat agctagtatc tcattggtga gagcagatca cgaggcaggg    78900
gatgccatgg gatgtaagtg ccaggtgtgg gtcatggcag gccacaaggg cagccatcca    78960
ccacacccat actcacgttt ggaaagacac ctggagccta aaccaaggg caagacactg    79020 taagaatcca ctccctcatg ccctatcaat aagccctaaa atattctttc ttttaagggg    79080
aaaattataa ccagtatgac ttgaatcgaa atttccccga tgcttttgaa tataataatg    79140
tctcaaggca gcctgaaact gtggcagtca tgaagtggct gaaaacagag acgtttgtcc    79200
tctctgcaaa cctccatggt ggtgccctcg tggccagtta cccatttgat aatggtgttc    79260
```

```
aaggtaagca ggtgcgggtc cagttctggc ttcttaagtc cagagtgggg ctgaaaactc    79320
tctgcctctg gatggggatc agctctccct tcccctctta acttctctgg cagggtgaaa    79380
agagcttcat gttcccaact ctagccatcc ttcctgtgat tcttcaacag cagatgggca    79440
gtgtggctga actgacaacc cacagctgga catgcatcag tgaattagtg aaatttagat    79500
tctagaaaat acaatctaaa tagtcagatt ttgattctct gacaagagac aacatggcta    79560
aaataacata aaactggaac aactcacttt ttttttttgct aatcatatat gaacaataat    79620
tgttgactct tcttaaaact ctgtgggatg aggacccaaa atattacagt agctttattc    79680
acccctataa tacctaaaga aattgtcctt acctccagaa attagcaaga gtgactgaga    79740
ggacacttaa ttttttaagct gatttaggag tttggatttg tatctgactt atttggggggc    79800 tatcaccttg catatgttta ttataaagta gaaagaagaa tagaggaggt ggatgaagga    79860
tttctctcta gggaaattag agcatgtgtg tgtgatgcga ttatgtcttt gctaatatgg    79920
tgtttgtgtt tcctcttact ctcaagtcag tttaaaggtc ttggttcatc ttttaaatgc    79980
agcaactggg gcattatact cccgaagctt aacgcctgat gatgatgttt ttcaatatct    80040
tgcatatacc tatgcttcaa gaaatcccaa catgaagaaa ggagacgagt gtaaaaacaa    80100
aatgaacttt cctaatggtg ttacaaatgg atactcttgg tatccactcc aaggtgagtt    80160
tctcttcatt tcttccattc tccttattgc cttcacccag aagtgccagc tggtttattt    80220
tgatccagca gttgttaaaa gaactttagg cacaataggc ccttcactct gtccttatca    80280
gctaatatca taagagcagt ggagatgact gattgtttga gagatgctca gacatgttcc    80340
tcattaccaa gggccttctt cattcattca ggtacttatt ctgtgtctgc ctactgtgag    80400
ccaggaactg aaagatgaac aagacacaca cctcaccctg gagttgaata ggggagacag    80460
acacgcagat aagtaattgt gatagcagtg caattagaat aaaaacagat ttagagaagg    80520
tgcagtgtac cccaagggtg cacagagcca aaatacaata gggagtagtg aagagcttgg    80580
agaaatgtga tgcttacatc ccatctaaca gggacagctg ctactagatc tagctaatta    80640
ttgtcatgca gccttgggga gccaatactg ccagatcttg cagtttgtaa agagaagctg    80700
aatttgtaca tgaagtatca tgattttaaa gccattttgc gggctcaaca aaagagctct    80760
tcagacagga tacagtggga ggagggcccc cagttctcca atcttggaat aagacagccg    80820
ggtaagggac aggatgagat tgtcatgtag gcaacatgga aggagagata ttcttattag    80880
agggaataat ataaacagaa acccggggta ggagggacct agggtggaag gacaggagga    80940
gagacggact ggaactggat ttccatgcct caggggaaaa cattccccttt tagactcgtt    81000 agcctgaccc caccaacagc aagttgcggc atgcatttct gcgtgcaggc cacttccaaa    81060
ggtgccttcc ctaattgtca ctttggatgc acaggctttc aggtaatctt tcacaagctg    81120
gtatttttat gcctgggtgg ctctctgtca gttttcctgg taatataaat aagcatagac    81180
cacaactgat aggcaacagg tccaggcagc attccaaacc tctctctggt gtccaagata    81240
cagccccctc tcctacctta gggcttctgc atcgtccctg ctctccacaa tttgtagcta    81300
agaaagggcc catcctgtcc agtggcagag ctgtccttca tgttcactgt ctaactttcg    81360
aaggcaaatc cagatgtgta ggaaattagc tagaaacggt tgctgctggg aattgttccc    81420
cagtgtgcct gtgtgtgagc tgtgtatcct tctcagacaa aaaacaggtg aagccagctg    81480
ccttgaggag cccagaagaa tgtgcctggc ctggcctgga tgttttgttg gccaggcctg    81540
acccgcctta tccagaactg ccccctccac gcttggcatt ctcagttctg gctatctgct    81600
```

```
agggatccat aatgcctgcc tgttttgcta tttaaaacaa acccttttgaa agtaagggac   81660 cagaggagag aactggaaag tcagcatgag cagtggcagc ctgggctcca caggggggccg   81720 ggccgttcac ctctgagagg cagtgcagca ctctttcttt gatccccagg agcactctgg   81780
catattgggg aagcccacag gtgctggcgg aaggtggcct gcactccagt gtctgtcatt   81840
tactggccaa aaccctgag cacttttctt taacatctgt gatcatgttt cctcatctgt   81900
aaagtagggg caattgctgt gaggattaaa tgagctgata caaagcactt catatggtac   81960
ctggcaatag tgaatgttgg cccatgattc ccccaaatta gcatgcttag ctttgcttag   82020
taagtgtatt tataaatgat ttgtagaaat attttaaagg aatcttattc tagcttatat   82080
ccatgtaaaa tgtaatttaa gaaagaaatg aaattcaaag aatcattttt gtaatgtagg   82140
atttcaaaaa ataaaaacaa aaaaggaccc ttccttcacc cgtcacttaa ttttgatgca   82200
cagttgaact tcagtcagct ctgatccagt tacccatatg ggaatattta ggattgtcta   82260
gtcacgcctg gtaatagaa tgtcaagccc tgattttaca agctaatatg tcaaattcat   82320
tttttcctgt ttacatgtag ctgtctgatt catttgtccc cgaggcacgt gatacttggc   82380
tccactccaa ttttagaccc taacaaaaat taaatatgct tgtgtttagg tggaatgcaa   82440
gattacaact acatctgggc ccagtgtttt gaaattacgt tggagctgtc atgctgtaaa   82500
tatcctcgtg aggagaagct tccatccttt tggaataata acaaagcctc attaattgaa   82560
tatataaagc aggtgcacct aggtttgtaa aattttctta ttaattccct attaatacaa   82620
aatagagcat ctggcaagac ctctgggttg actaaacgca agcctttatt tatgctttgt   82680
agttatagcc tcatttcagt gccagatctg atggttaaga attctctctg catgagtatc   82740
tgcagtgtgt gagaaatgca gtgcccactc attcatagaa aaggaagcat gatgcatgtt   82800
cctttaatat gagggtataa aaatccagag taccaggtgg tcgtggtggc tcatgcctgt   82860
aatcccagca ctttgggagg ccgaggcagg tgtatcacct gaggtcagga gttcgagacc   82920
agcctggcca acaaggcgaa acctcatctc tactgaaaat acaaaaatta gccaggcgtg   82980
gtggcacacg cctgtagtcc cagttacttg ggaggctgag gcaggagaat cacttgaacc   83040
cgggaggcag aagttgctcc ctccgccaag gagccaagat ggtgccaatg tactccagac   83100
tgggtgacag agtaagactc catctcaaaa acaaacaaac aaacaaacaa acatccagag   83160 tcccccctaat tttacatgtt gaatgatcta gaaatctggc aaaatatcag gaaaataggc   83220
tgctactctg ttacatcatc tcccatttag aaaaatacta tgtttgcttg tcactcacca   83280
cgcagtacca aggaccctga gaacactgga cataccactt tgcatttttt ccagaattgg   83340
ggtggtgagc tagcaccatt accttcaacc cctctcacct ccgaactctg ccagatgtcc   83400
tggtgctaga aatcttgcca gcctgtttgc tgaaggctgg ctgcccctta tcacagatag   83460
acagactaaa tgtggcagag agtgatagct ttcaaacgtg cagtggactc accgggagcg   83520
cttgctaaaa cagattgcca ggccccaacc cggagtttct gtttggacca ccttaccacg   83580
tgatgctgat gctgctggtc cagcggctat acttagaaag ccattgcact agagaaacac   83640
actgctagag atgatgatgg aatcttgtac agttcaagtt tattaaccag gtggtgtctc   83700
tttgggcaag gtgtggaagg ctcttctata tttacagagg tgaagttatc tttctccatt   83760
cagaatggct tggggagaga aacatatcag gaattggcat aatagctatg ataccacatg   83820
gagagagaga gagagagagt gtgagtgtgt gtgtgtgtgg gtgtgtgtgg gtgttgaaaa   83880
ggtttgctgc atgggcctac tgcataactg cataattccc ggaattttct gcatgattca   83940
cagcaaagct ttcctcctgc tacaaagaag atggagaagg atgagggaag gtagcacagg   84000
```

```
gccagagggc tgagtgcaag gatgattagg acccttcctc ggcacacatc cctaaaaggg   84060
atgcccctgc cctctttcat acctgtatcc ccagcctcca tgcccctgacc tgaagagaag   84120 tacacaaaga ttactggtaa actcacaggg ctatgtctaa ctggctgagt cgttcatgga   84180
ctaggttgac tccctgtgat aggggatgtt atgaaatatc gttctttctc accagcatct   84240
taataaagat tataaactta ttattgggac tttcaccttc ttcattatgt catcaaacgt   84300
tgtcttgggt tctctcttgc ttagtattct ggtaattctt tctccactag attttcctca   84360
tgaggcatgt catgtattag tctaacattt ctattatatt tctacctcta ttgatccttt   84420
agtttgttaa tctattacta ttattatcat tatcatcatt ttagagacag ggtctcactc   84480
tgtcacccag gctggagtac agtggcacag tcattgccca ctgtaccttg aactcctggg   84540
ctcaagtgat cctcttgcct cagtgtccca agtaagtagg actacaggtg cacagcacca   84600
catccagcta attttttaaa caattttata tagagacaga atcttgctat gttgtccagg   84660
tgagtcccaa actcctgggc tcaagcgatc cttctgcctc agcctcccaa agtgctggga   84720
tcccaggtgt gagccaccgt gactggctct gcctatcctt ttctgaaatt cattcttcac   84780
cagtatcaac atgggtatgg gcgtgcaagt gaacatcaaa tatgctctgt gtaactgcac   84840
tactattttc agaacctcaa tctagctgta aagattattt accaagcact gaattaaggt   84900
gggctttgaa gtatcatgtt gatgtaatat tgccagggaa agggcaatat aaattgcagt   84960
atacctatta ttatttttaa taatttggaa ggcttaccag tccatttgca ctaggttttg   85020 ttttttttgtt tttgagacgg agtctcgctc tgtcatctag gctggagtgc aatggtgtga   85080
tgatctcggc tcactgtaac ctccgcctcc caggttcatg tgattctccc actcagcctc   85140
ccaatttgct ggaattacag acacccacca tcatgcccgg ctaattttgt attttttgtag   85200 agacagggtt tcaccatatt gcccaggctg gtcttgaact cctgacctca ggtgatccgc   85260
cggcctcggc ctcccagagt gctgggatta caggcatgag ccaccatgcc cagcccattt   85320
gcattaggtt ttataaagaa tgtgtatctg cctgtctcta taatcagatg caaacaactc   85380
actcaaaaaa tacatatatt ggcacatcaa ccctgccccc ttgtggttta agacagatgc   85440
ataacatggt ttaataatga aaccatattt caaaatacca atacagtgtg gttattacta   85500
cttaatagaa aggttctctc cctactagtg cccaataaga aactaatgaa tattttgttt   85560
gtgaagaatg gcagcaaaca cccctttatt ggtattgctc tggtttaaag acattattga   85620
tattcgtcaa actgcattgc atttactggt tccattttac caattgctag gatgcttctg   85680
agtttctgag gttttgaccc atctggaagt ctctgagcca ccttgtctgg gaaggaaagg   85740
ccttctgctt tagtggaagg gccttgccaa gagggtagag gcttaggtag agcccaagct   85800
gttttgtcat ctggcgatgt ttgcaatctt gagcaagcac ttgtctgaat ctcagtgtag   85860
tcaacagaaa gttgagagta atagcatcag ccttgcctcc caccagcctg ttctaaggct   85920
tcagtggtgt tattccttca attagaactc actgcagacc tcaactgaaa ctcgggcccc   85980
ttggtgctgt gttgtcctgc ttagaggatg atttactagg ttcaagttga gatgagggtg   86040
tcggcagaca ttaaaaccaa agtagcaaag gagggcaagt ctgaattcta gaggcttaaa   86100
atgtcttgct tgtcccggtc tctgaggaga agcaaagatg agccagacac ggtgttacct   86160
gcctgctgcg gccctgtctt tcccctggac tcctcaaagc agatctgaac ctagagagca   86220
agggaatggc tcacagcatc cagaaaccta agcaacctgg gcataaaaga atctggtatg   86280
tgctgagttc cagaagcctg tgagccacag atgtggatct gttatcacat ccaaaatagg   86340
```

```
aggcaactgt gaccatgcgg tggggacatg ggcacaaaca agcagtctcc taagtactgt    86400
cccagctccg actctaaatt gtggccaaca gatgcagaat tctagtgctt gcccagccaa    86460
gacttttcat tcatgaagct ctaatccatt tccaagggaa aaagagcttt acatttctcc    86520
catgtatctc cccatctggc cacagaattt atatctcaga ttttatgtct tctcatttgt    86580
attgtatctg agcattttc aaattttcct ttttttttt ttaatatagt gttggctctc    86640
tctgcgtctc ttagggtcta ccagtctttt tttcaatgtt tcaacttcag catatagaaa    86700
taaatcacat tttctggtaa aacaattact tccctcttaa gtaaaggtt tggtggtatg    86760 tagacaaaat attgtaaaga catatacaag ctaaagcacg cttttatttg gctggtggga    86820
ggggttttcc tttgaatata aattccatac ataagcatgg tctgtgtttg cccagtaaca    86880
gtgatattcg catacccag gcttccatag ctggaagaac catctttagg tttaggtaag    86940
agtcatatga aagtgagtct ttgggcctgt aatcccagca ctttgggagg ccaaggtggg    87000
cggatcactt gagatcagga gttcgagacc agcctggcca acgtggtgaa acccatctct    87060
actaaaaata caaaaattag ccaggtgtgg tggtgggcac ctgtaatccc agctacttgg    87120
ggtgctgagg caggagaatc gcttgaaccc gggagatgaa agttgcagtg agccgaactg    87180
gtgccactgc actccagcct gggcaacaga gggagacttc aatttaaaaa aaagaaagt    87240 gaatctttgg gttattaggg gatgacgaat gagggtcaaa ctggaatatg aagattttca    87300
gacatttctt caaatgcaaa ttgttcttcc tttttctatc tttgagggta ggcagaccgc    87360
aggttgactg gagccttgat tcagctgcag cacacactga tacgtaggtg ttgttcaagt    87420
ccctgaggcc atccaaaatc actgtcatgt gactgtcaaa aaagtcaaat ctgttctatt    87480
aaagtgtaac tgcttctagc caagaagaaa tttgctgcct ttttttaaag ggtaccatga    87540
cttttttttt ttttttttt tttttttggt gtcttctgcc aactactcat tactagtacc    87600
ctgaattcta tttcatcatt atctccaatg ttaaagaatg gtgtaatgtt agccgggcgc    87660
gatggctcac gcctgtaatc ccagcacttt gggaggctga ggcgggcgga tcatttgagg    87720
tcaggagttc aagaccagcc tgaccaacat ggagaaaccc tgtctctact aaaaatacaa    87780
aataagatgg gcgtgatggt gcgtgcctgt aatcccagct acttaggagg ctgaggcagg    87840
agattgcttg aacccgggag gcagaggttg cagtgagctg agatcgcgcc attgcagcct    87900
gggcaacaac agcaaaattc catctcaaaa aaaaaaacaa aaaattgtgt aatgtcagtt    87960
tcaatgatag ctctgcttca ttttttatgc acttgatttt cttcgatttg gttggttttg    88020
gggaagtcaa caaaaaatac aaaagatgcc aacagacaca acaccatcca gcacaagtta    88080
ccttgctgaa acgcatggat tttctaagtg gcatgaagac tgtaaactag ctcagagccc    88140
tggaaaagga aataatatgc atagcttctt ccctcacata ttcctgcttt gtggaacaaa    88200
gttgaattaa gactccagaa attcatctaa tatattctcc ccccgccaca ccacatagtt    88260
tttcttaatc caaataagag gaaaggaaag aaagccaggc ctggtggctc acacctataa    88320
tccctgcact ccagcacttt gggaggccaa ggtagatcat gtgagctcag gagttcaaga    88380
ctagcctgtg caacatggcg aaaccccacc tctacaaaaa aatacaaaaa ttagccaggt    88440
gtggtggtgt gtgcctgtag tcccacctac ttgggaggct gaggtgggag gactgcttga    88500
gcatgggaag tcaaggctgc agtaagccct gatcacacca ctgcactcca gctgggtga    88560 cagagcaaga ccctgtctaa aaaaaaaaa agaagaagaa aggaaagcaa gaattaatgt    88620
ttgttgatcc tcctgttctg tgttacttac atttaatctt cacaaccatc ctgggtggtg    88680
gtatattatc cccatttcat aggtgataaa attgaggctt gggaatgttc agtgacttga    88740
```

```
gaactagaat tcaaatcaaa acctgactag gttctttctg tcacaccaag ctatgatgat    88800
gggtacacgc tatatttatc acatatcaaa ggacctccta aggggggcac agtgtaaata    88860
gctcttcaaa ataatgccat tgaagctgag tgtggtgcct cacacctgta atcccagcac    88920
tttgggaagc ttaggcaggt ggattgcttg agcccaggag ttcaagacaa gcctgggcaa    88980
catggtgaaa ccccatctct acaaaaagtt aattaattaa ttaaataaaa caaaataatg    89040
ccactgaaac ccaaggaata aatgcgtaat caggttacca aattattacc aatttatgat    89100
tgggtactac ctaaacatca aaaggatatg tatcaagcag taggaataaa tataaatgga    89160
actgtgttta aaaagagag ggcaaagagg aacacacgaa gtgaaaatag aagtttacac    89220
agttgtatag agaaagggag aaggaaatgt ggcattttcc tcctcaggag acaaaaaatg    89280
aagagtcagg aactaaatag gacagaaagt ataataaaag gcaacctagg tcagatagaa    89340
gtttgttgaa gttcaagata acattgtttt tgctaaatgc caaaattttt atttttcact    89400
ttaaccgttt ctgggggaaa ctgttacgtg tgcctcgtat ttttctgccc taataaataa    89460
ttattgagca taactgtttg gggagagttc aagatcatct tactattgta gctcttcatt    89520
ctcatttatg ttattgggga cttaggcagc ttcaccttaa ggtaatatga tttgacgctg    89580
gagtaaacaa actagatgtg acacgtagga tctaaaataa gaaaggtctt aaaatataaa    89640
tggctttta aaaattgtac tcctgaaatt ttgagagggg ctgtcgagac tatcatgggt    89700
tgacggctag gctgggccac ttcgttggct gtgtgagttt gaggaggtta ttttaataag    89760
ccagagcctt agttttttc atctgtaaaa tcatgataat aattgatgac acagagctga    89820
tatgagaatt taatgagaaa atgctcattt ggtagttagt acagagcctg gaatatacta    89880
agtgctcaat aaatattggc tgctgttact ggccaatcga ttccatgctt ccaagaagcc    89940
ttgtgattat aattttgctt cccatgtagt tgcactacaa gacaaaacta ttgagtccct    90000
cgcacacgta aatattttgt tgtaactaat acattgacac cgttttttatt taggatttta   90060
tggaatccac caatggttgt agtacagttt ggtgactgag taaataactt ggaagtgaca    90120
ggaatggatc ttaggttgtc atctgtgttc tctcactgtg ataatacgta ctaatataaa    90180
tgggctattc aacaacgaac aaatttaagc tataaatcag attagtaatt ttgactgtat    90240
tttaagttac atcaaaaata agttttttcc ctctctaaca cttaatatta actcacaaca    90300
ttgagttagc taataaatat tgcatatatt gttcttaaat atttataata attttatat    90360
gccataaaat atggtattaa tatttaattt tattttttgtc ttgcaggtgt aaagggtcaa   90420
gttttttgatc agaatggaaa tccattaccc aatgtaattg tggaagtcca agacagaaaa    90480
catatctgcc cctatagaac caacaaatat ggagagtatt atctccttct cttgcctggg    90540
tcttatataa taaatgtaag tatgcaatgc tagttattgt tattaaaata ttatagaact    90600
cataatactt attcacccag aaggaatcca aaataagtct aggaagttca aaagtagatc    90660
catcgagaca gaaagaaagg atagtgtcag acttgcaatt ggcaggaggt ggaagaggtg    90720
gaaattatat gaaaaaaaaa aaaccacaa aaattcatat tttttccctg atggcaattt     90780
ttaaaaaatg gaagccaaat cctatctctt gtgatatctt ttatgattaa aatgtaaccc    90840
gattaataat aaagaataag caatgtagca aaggtagttt atagtttccc aggatacgac    90900
acaacaccca ttccacggca tacactttct actataaaaa atgaattgga taaagttcct    90960
tagaattcat tttataagtg aaatctgatc cacaaatttt aacactatat tcagcaaatg    91020
ataaacatat tttgcagccc ttttttcatc gatgcaagta aaatttcagt ctttaattcc    91080
```

```
ataaaatata tatttctgag tcattttatc cgaagacagg aaggcatgga ctaatttgag   91140
cctgagtgga tttatgtgaa agaactaaat gaataagtat tgatatagtt ggccagattt   91200
tgcctctttc tctttgatgt gaatttctct gagaaattca ggattcttct attttgctta   91260
gtggggctta tgccaaccat agcagtcatt ctatatagag ctaatcctgg gagaaggtag   91320
tcatctcttc tgtagtgaaa actgagttgg tattttatta tttcatcttg aggacatcat   91380
ggaaaaaaca tggttttag tttataaaac tatagaattc agagcctcca tgctccatgg    91440
gttctcccca aggtgcctag atgtgaggct tatcaattgc taatccttt aggaatttct    91500 actcctgccg agaaaatgga tagagcttga aaaatctcaa ctcactgtga atctttgtct   91560
aaaaaggccc tttattttcc tcctatttac tgtgatattt ctattctatt taaaaatatg   91620
attttccctg tagtgaatct aaacttatat gcaacctcat aaataagcca cacctttaga   91680
ataaagttat gaattgttca tttcccatta gttagactaa cacagtacac attgaccta    91740 gatattagtt ctaggataat atttgaaggt aagactctgg acattgaaat gaatgtgtaa   91800
aatacatacc aatgagtggt tatgtaaatg tcattcccca ttttttccct tctccaccat   91860
atataataaa agcatttctc agtagacatt gcctgtagtt agtttagcat ttgtcttgtc   91920
ctgatcattt cctccactaa aaaaaaaag aaagcctaac caaagattca ggctgatatg    91980
aacaaaacca ggtaaaatca aagcttttaa aggagggtgg atgtggtggc tcatgactgt   92040
aatctcagca ctttgggagg ctgagaggca ggtggatcac ttgaggtcag gagttcaaga   92100
ccagcctggc caatgtggtg aaaccctgtc tctactaaaa atacaaaaaa ttacctgggc   92160
atggtggtat gcacctgtaa tcccagctac ttgggaggct gaggtaggag aatcgcttga   92220
acccgggagg cggaggttgc aatgagccaa gattgagcca ctgtactcca ggctgggtga   92280
cagagcaaga ctctatctca aaaaaaaaaa aagaaaaaag aaaagaaaga aagaaaagct   92340 tttaaagaa gcaataggct tgtaggtcag ctgaaaagaa attagtaagt tgagaaaata    92400
attctacttg aaaataatct tgatatccaa ggaggatgtt aaatacacac ttgggacaaa   92460
gggaaagagt tatctcttta cccttctgcc ccacgaaaag gatggtggca gaaacatctg   92520
ctgcttcctt ctcttgactt acattgccag atgaggtacc catctgtcct tatttcattt   92580
tgtaattctt ggcaacagca ttcacaacgc tggtctctgt caacaggcat tggataactc   92640
agcctgcagg accaaatctg ttgctggccc agaggtctgg tagattgtta catgcattgc   92700
acaaaggctg cattttagtg atggatatca gtgttttcag tgtgggcacc acgaaccatc   92760
ttaagtcact catataattg tctcttgttt cttctcaggt tacagtccct ggacatgatc   92820
cacacatcac aaaggtgatt attccggaga atcccagaa cttcagtgct cttaaaaagg    92880
atattctact tccattccaa gggcaattgg attctatccc agtatcaaat ccttcatgcc   92940
caatgattcc tctatacaga aatttgccag accactcagc tgcaacaaag cctagtttgt   93000
tcttattttt agtgagtctt ttgcacatat tcttcaaata aagtaaaatg tgaaactcaa   93060
cccacatcac cacctggaat cagggattgc tcactccagg ttactgcaac cctaactcac   93120
tctagtggga ccttgactgg agaaactcca cgatcttcct gaagaagaga aatggatgtt   93180
tccaaattcc acaataagca atatgtggtg ataatgaaaa gaatgattca gtcttgacgg   93240
tgaatggaag acacttacct aacaagtact gctcatttac actcaaatta atcttgaagt   93300
agtcttaaaa tgtgtaagaa gttaaaactt gagaagcaaa aaaatgcctg caaaagaaag   93360
atcattttgt atacagagaa ccggatgaat ataagcaatg aagatgaaca tttattgatc   93420
ttctacatac aagacttcac cataaggcca ggagcagtgg ctcacacctt gtaatcccag   93480
```

```
cactttggga ggccaaggtg ggcggatcac cctgaggtta ggagttcaaa accagcctga   93540
ccaacatggt gaaaccctgt ctctactaaa tattagcggg gtgtggtggc gggcacctgt   93600
aatcgcagcc tttcaggagg ctgagacagg agaatcgctt gaaccctaga ggcggagttt   93660
gcagtgagcc gagatagtgc cattgtactc cagcttgggc aacagagtaa gactctgtct   93720
caaaaaaaaa aaacaaaaa caaacaaaca aaaaaacac ctcaccatga gtgctacatg   93780
tgaatagata ttaagtgcca tatataatta gttctcagaa gaagggagaa atgatcatag   93840
gactgggaat tgttttgcaa acgttctagg agatgtgaga gaaatatgt aaccacatct   93900 tagtggccca agaaaataca ggcctgaagg gataagattg tgtctctata gagcttcaaa   93960
gcatacaggt caattaagaa agcccctctc tctccagagc cgtttcccta gcttttggca   94020
cctggatgcc acagtcctcc attaggctga tgactccaaa gatgtaactc tagcctcttg   94080
cctgagcttc agactcgcgt cccactgccc acaggacaca tccacctgga tgtgactcac   94140
aggtacctcc aacccatcat gtggagatac tcatcctgtt cccctagag ctgctcttcc   94200 tgctgcattc tctctctcaa ttactgggac caccaagcta ggaacctggg agtcatcctt   94260
gatactttct cttcctcctt aatcctgtgt attcagcaag taactaaagg ttggtgttgg   94320
ccaggcatgg tggctcatgc ctgtaatccc agcattttgg gaggccaagg cgggcggatc   94380
acttgaggtc aggagctcaa gaccagcctg gccaacatgg tgaaacccca tctctactaa   94440
aaaaaaaaaa aaaattagtc gggcgtggtg gtgcatgcct gtaatcccag ctactgggga   94500
ggctgaggca ggagaatcgc ttgaacctgg gaggcagagg ttgcagtgag ccgggattgc   94560
gccattgtac tccagcctgg gtgaagaagt gagactctgt cttaaaaaaa aaaattggtg   94620
ctgataaata ttgatgaatt ctgctctctg ctctctatgg ttgtcaacac tgcagagttg   94680
aggcctcata tctcacctgc actgctgcaa cagcttactg gtcccttgct cccagccttc   94740
tcctcttcag tccatcgtcc acacagcact ggggaagggg agccacttga acaaaagtc   94800 aacaactggt tgtagttcat aaacacagag ctgtttgtgt cccctgtatc tggaatgcca   94860
ttatgaccca ctacattttt tctttcctac ccctcttaaa actcagttca ggtagcagct   94920
ccactaggaa gccttggctg accataatcc cattcaattc catttcacct cttcgcaggc   94980
agtctggggt tagggaccct ttctctttgc tccccaaaat aaactggtta tctctactat   95040
tggatttaca acattgtatt ataatcttct ccatgtgtgc cttctctagt agaatgtgag   95100
ctctttgagg ccaaggtcta tttaatttgt ttgaaaaatt cattgttata tcctcaaagc   95160
ctagcacata gtaggtactg aatgaatgaa tgaacaaggg gtgccaggag actgctactc   95220
ccagtccttc ccagaaactg cctagggctt tgagtcattt tatgaagcta ggtcttaatg   95280
cgtaggcaac ctcccagctc actatgaacg ctgacagaag agtgttttca tgtctataat   95340
caagaattcc agatacattc cttttactga accttgaatt gatcctaaga ttggtagtaa   95400
aggtattatg ttacctccta acagcactac aaagtaccct tttttatcag aaaaaatttt   95460
taccattagg actcaatttg aagtactaat gcttctcaag ttctccacta tgagagttac   95520
cctgtattag accgttacct ataagaatta aggggtaaag cactaaacag aaaagaaaaa   95580
aaaaatagca actctggtga gcagatttct ttcctttctt ccttccttct cctcttccta   95640
ccttcctccc tcctttccct ctcctcccct tctctcccttt tccctcccct tcccttcctt   95700
ttcttctttc ctccgctccc ctccccttcc ctccccttcc catccttctt tctctttttt   95760
ttacttaatc cccagtgtga cagtaatata ggctgatttc tagaagtgtg gtgtattact   95820
```

```
catggaaagt gagttgcctt ggttattact ttcaattgaa agttctatgg gatctagaaa    95880
tgagacatac tggcatggag agtgagaacg acaaaggaat gaagagctac aggagcattt    95940
aggccatttc tatgccaagc ttattctaca tgcacaaaat catacatgtt aataaatata    96000
aacaaattgg aggcttattt aaaccaatta tgaaatctgg taatttgtgc agcagcaata    96060
gatgataacc aaaaaaaact cataataatc tgaatatctt gatcatttgt atttaaagaa    96120
gcagtaatta tatacttgaa agtacataat atagtattgc aaaaatgact ttggtatatt    96180
acaaattaaa agtatataag atgaaacttg atttgctatc aagccccaag caattttcca    96240
actgggcatt gaattctaac ttttctaaga tagcaatttt tgaagagaca cgaacaaaaa    96300
tctgaattag ttcatgagcc ttaatgtaaa tctcttgctg aaatagtttt taaaatcaga    96360
atttagttat ctatcagact caaaatcatt taaagactaa caaaacacaa tcatgatatt    96420
ctaactgtgg tcaaaccagg tacccaagcc acctccctgc ccaacgcctt tccggctttt    96480
cccctccctc ttgggctggt ggttatgctc ctccagctct agttcagcta taattccttt    96540
tatagagaaa ccaacctgat acacactttc atgatgggag aaaaatgtgg gagtgaaatg    96600
gtatttagaa agcagcagtc aggcacggtg gctcatgcct gtaatcccag cactttggga    96660
ggctgaggca ggcggatcac ttgaggtcag gagctcgaga ccagcctggc caacacggtg    96720
aaaccccatc tctactaaaa aaaaatacaa aaattagccg ggcgtggtgg caggcacctg    96780
taatcccagc tacttgggag gctgaggcag gagaaatcgc ctgaacccag aaggcagagg    96840
ttgcagtgag ccaagatcac atcactgcac tgcactccag ccggggtgac agagcgaacc    96900
tctgtctcaa aaaaaaaaa agaaaaaaga aagaagaaa aaaggcagaa gccctggatt    96960
caaatccgcc acacattcag tttctttatc tgtaaaatgg agaccacccc ccgccacgct    97020
gaacggtgat tctgtgactg gtaagagatg ctacattttt ggtgcttgtt caggtggagg    97080
aaagatgata gttaacactc aggtaataag tattttgaag gcagtataat ataccttctt    97140
aaagagtata cctactcaaa tgttggtaaa tgttgacatg attgaatcta aatggcaaag    97200
agtattttag aaaaacatta agtccctgca gataaatgac agtgttgatt tggatgctta    97260
attacattca gacatgaact gttggatgta tctgaaatgt taaaagcttt ttctcaacat    97320
ttccaaaagt ctttccaaga aatcaatgtt atgttttgtt ccagaagcaa atttgcattt    97380
gtgatctgtt tctaaaaatg gtacaagtta gctctgttta gaaagtaaaa atatctgatg    97440
ttagattgga agtatctctt cctggggaat ccagaaagat aagcatagca tattgtctta    97500
ctgcaataga taagttgctt attgagaagt ctggttgtta ttctatatgg taacaataca    97560
gttgatgtat attttatgat agatcctttta tattttcctc atgactttag aaggggggaag    97620
ggggagaaaa ttatgatgac cagactagtt aaagagcatt gaaagtccac agtactgtag    97680
ctaaagtaga agtttgggtt tgttatagac tttacattat atcaactaat aagcagatac    97740
tgtacagtat tgctcaccat tttatctac ttttgcatat gaactactcc attgcctttt    97800
atagatgttt tatagctgat cttaccagtt ttcctggtaa cttttttat ttctttttt    97860
tttttttgag acggagtctc gccctaacac ccaggttgga gtgcagtgcc gtgatctcgg    97920
ctcactgcaa cctctgcctc ccgggttcaa gcaattctcc tgtctcagcc tcccgagtac    97980
ctgggactac cggtgcctgt ctccacgccc ggctaatttt ttgtatttgt agtagagacg    98040
gggtttcacc gtgttagcca ggatggtctc gatctcctga cctcatgatc tgcctgcctc    98100
tgcctggacc tcccaaagtg ctgggattac aggcgtgagc cccgcgcccc agccactttc    98160
tttaatacta taactaagaa tttattaaaa tgcacaaatt gtctaagact gtaaagttta    98220
```

```
ttggggagag gccatgacta cctctgaatt tagtaaattt aaaatatttc tgattctcaa    98280
taaagaacta atatccatat aaataatgct tttttcccat tatgttacct gaaaataagt    98340
acttatgcaa gtataacaaa gtccactaaa aataactgat taccaccaaa taaagcttgg    98400
gaaagaccaa acttaatgac cttttatgag gcaataacat tgcaacaact cttcaaagtc    98460
cagatagttc ttccagaaca agttacatat gctatatgtt atatatatta tatataatac    98520
attccaaatt aatttgtgtt gtggggcagt gtgttccatg gacaagatga tggatggaaa    98580
gtatgccttc tggtcagaaa aaatatttga aaattcacaa tttatattaa tgtaataaag    98640
aatctgagaa atgcagaaaa gaaatggatt tcccaaacat gctaagctat gggaccattt    98700
ccttaaataa tacagcctcg taccatccct ttggattaac atacctatat ttccaaacac    98760
attttgggaa atactgatat atagagaagg cttttgttct gaataacaaa ttttattgat    98820
ttccaggtgc ttttgaaata cagagaacag tggtaaacaa agaatttgcc tccagtagga    98880
actggaaaac taacagtcct aaccctgct aatatcgact tagtcatagg acagaggatg    98940
ggctcaagct tacatctgct cttttgaaaca cgctaaacaa ataatagttt aaatgagaca    99000
ttgctgagta ggaaatggct aaattacagg taccattttt taaaaagtga cgtctcaatt    99060
tagaaaataa acaggaaata gtttctctgt tttcaagaga atttcattac atagaagcct    99120
cttaagcaga agttccctgg tatatttacc tagacttcaa cgtttaaatt tgcagctttt    99180
tttttttttt ttgggacgaa gtctcgctct gtcacccagg ctggagtgca gtggtgggat    99240
ctcggctcac tgcaacctcc acctcccagg ttcaagtaat tctcatgcct cagcctctcg    99300
agcagctgga attaacaggc acatgccatg acgcctggct aattttttgta tttttagtta    99360 agacagggtt gcaccatgtt gcccaggttg gtcttgaatt cctggcctca agtgatccac    99420
ccacctcagc ctcccaaagt gctgggatta caggggtgag ccatcacccc ccagccaagg    99480
gttttttgtt tgctgtttga caactgagaa tagaactatt attttctctgc tctcttggag    99540 tggtctctca gcgctgttaa gagtctacca agcgtagtga ctcacatctg taatcccagc    99600
actttgggag gccgaggcga ctggatcacc tgaggtcagg agttcgagac tagcctggct    99660
aacatagcaa aaccccatct                                                 99680

<210> SEQ ID NO 4
<211> LENGTH: 51039
<212> TYPE: DNA
<213> ORGANISM: Homo sapiens

<400> SEQUENCE: 4
tggtctctca gcgctgttaa gagtctacca agcgtagtga ctcacatctg taatcccagc      60
actttgggag gccgaggcga ctggatcacc tgaggtcagg agttcgagac tagcctggct     120
aacatagcaa aaccccatct ctactgaaaa tacaaaaatt tgccaggcat ggtggctcat     180
gtctgtaatc ccagcacttt gggaggccga ggcaggcaga tcacgaggtc aggagttcaa     240
ggctagcatg gtggctcatg tctgtaatcc cagcactttg ggaggccgag gcaggcagat     300
cacaaggtca ggagttcaag gctagcatgg tgaaacccg tctctactaa aaatacaaaa     360
aattagccat gcatggtggc atgcgcctgt aattccaact actgggaggc tgaggcagga     420
gaatcatttg accttgggag gcagagtttg cagtgagctg atatagtgcc actgcactcc     480
aacctggagt gagagactgt ctcaaaacaa acaaacgaac aaacaacaac aacaacaaaa     540
aaaaaaacgg ccaggcgcag tggctcacac ctgtaatccc agcactttgg gaggccaaag     600
```

```
caggtgggtc acctgaggtc aggagttcga gaccagcctg gccaacatgg tgaaacccccg    660
tctctactga aaatacaaaa actagccagg tgtggtggtg dacccctgta atcctagcta    720
ctctagaggc tgaggcagga gaatcacttg aacctggggg gcagaggttg cagtgagccg    780
agatcgcgcc acttcagtct agtctgggcg acagtgaaac tccatctcaa aaaaaaaaa    840
aaagggtct accgttagtg dacacctttta gtcttccaac gagatacttc cacctcccac    900
cttgtggtta aaaaatgctt aactttgggc tgggtgcggt ggctcatgcc tgtaatccca    960
acactttggg aggcagaggc aggcggatca tgaggtcagg agttcgagac cagcctggcc   1020
aatatagtga aaccctgcct ctattaaaaa tacaaaaatt agctgggcat ggtggcaggc   1080
gcctgaattt ccagctactc gggaggctga ggcaggagaa ttgcttgaac ccaggaggca   1140
gaggttgcag tgagccgaga tcatgccact acactccagc ctgggtgaca gaacgagact   1200
tcgtccccccc caaaaaaaca aaaagcttaa ctttgaagag atttggtctt ctcagatgcc   1260
tcctataaaa agaaacaaat gtgagaaaag gtagaaaagg cctttttttgt agggagcaat   1320
ttttttctaaa aaggcttttc agccaagacc ctctctctta caattctgac accatatcaa   1380
cttttaagac tacttttttc ttagaatgct tctttttttgc catttattgc acaaacaata   1440
atttgggggg ggactttaaa aaatcataat caggccaggc acagtggctc aatgcctgta   1500
atcccagcac tttgggaggc cgaggcaggt ggaccacatg aggtcaggaa ttcgagacca   1560
gcctggccaa catggcaaaa ccccatctcc actaaaaatg aaaaaattag ctgaaataac   1620
acagctactt gggaggctaa agcaggagaa tcacttgaac ccaggaggtg gaggctgcag   1680
tgagccaaga tcacgccatt gcactccacc ctgggcaaca gagcaagacg ccatctcaaa   1740
aaacaaaca aaaatcaca atcagtgaga ttaatgttta atgaacatac tgttatttttt   1800
tatttttta agagacaagt ctccatctgt ctcctaagca gagtgtagtg gcgcaatcat   1860
agctcattgt aacattggac tcctgggctc aagtgatcct cccacctcag tctcccatgc   1920
atgccaccac aatttttttgg atacagggtg tcattatgtt gcccaggctg atctcaaact   1980
cctggcctca agtgatcctc cttccttggc ctcccaaagt gttgagatta caggcgtgag   2040
tcacagagcc tggcccagga tgttatttta aaattgtctt tttgtcttct aaatcaacaa   2100
gaacttgata gttgctttca atgccaatca acatccttta ctactgtata cacaatgtat   2160
ttatttgaca tttgaaagga gatacggctg ggcgcggtgg ctcacgcctg taatcccagc   2220
actttgggag gccgaggcgg gcggatcaca aggtcaggag atcgagacca tcttggctaa   2280
cacggtgaaa ccccgtctct actaaaaata caaaaaatta gccaggcgcg gtggcgggcg   2340
cctgtagtcc cagctactcg ggaggctgag gcaggagaat ggcgtgaacc tgggaggcgg   2400
agcttgcagt gagccgagat tgcgccactg caatccggcc tgggctaaac agcgggactc   2460
cgtctcaaaa aaaaaaaaa aaaagaaag gagatacaaa aggatgttac aacctgctat   2520
ggcaagaaga tacaaggaa catattggta tgaacagaat acctcagagt tgagtgtata   2580
aaaaaggctt aattcaccag atgcagtggc tcgcacctgt aatcccagca ttttgagagg   2640
tcaaggtcaa gacacgagga ttgcttgagc ccaggagttc aaggccagcc tgggcaacat   2700
agcaggactc tgcctctaaa aaagtatat atatatatat aatgtacaca cacatacata   2760
cataaacaca tatgtattat atatatatat gtaatatatg tatattatat ataatatata   2820
tattagccag gcatggtggc aacaggcctg tgttcccagc tactcaggag ctgcagtga   2880
gtcatgtttg cgccactata ctccagcctg ggtgacagaa tgagccctg tctcagcaaa   2940
aaacaaataa aaaacttcaa ggtggagtag gggttaattc aaggctacct aagctggatt   3000
```

```
tggggtgatt atggtcgagt ggatgcaaac agaatattaa acttccattc attaaaagtg   3060
cttactacct gccagacccc atactaggct ctatagattt attgtctcta aggtcactag   3120
gcgagtaagt accagatctg tgactttgaa cttcccacta caataagctt atgaactttg   3180
tttaagcaaa aaaggtttga aaagtgaaaa gcaagcaccc atttcatagt gttctaaaag   3240
tctaaaataa tccagtagaa catcagagat aaaatccaaa aagcaagttt tcccccaat    3300 atttaaatca gggaagcaac atgatggtat ctgtaaacta taactgaacc aaaaatagga   3360
ccaaacgtag tgaaatccat ttagggagat attactgtga tcttgaagga aggcctactt   3420
aatacaggac agtgggctgg ggaggtgtga accaaaaata gacacaggca aaagcgctaa   3480
aatttaaccc tgagaaataa atgaaattca cctacaaaat aaatggaata aatttaaaag   3540
gtgaaatttt gggcttggcg tggtggctta cacctgtaat ctcagcactt tgggaagcca   3600
agacgggcag atcacttgac cccaggagtt tgagaccagc ctgggcaaca tggtgaaact   3660
gtctctacaa aaatacaaa  aattaggccg ggcacggtgg ctcacgcctg taatcccagt   3720
actttgggag gccgaggtgg gcggatcatg aggtcaggag ttcgagacca gcctggacaa   3780
catgctgaaa ccccatctct actaaaaata caaaaaaat  tagccaggtg tggttggcga   3840
gcacctataa ttccagctac tcaggaggct gaggcagaat tgcttgaacc tgggaggtgg   3900
aggttgcaat gagccgagat tgcaccactg cactccagtc tgggtgaaag agcaagactc   3960
tgtctcaggg cgggtggcag cggggtcggg ggaggtgggg ggaaggttag ctggacctgg   4020
tggcttgcac ctgtggtccc cagctacttg ggaggctgag gtgggaggat tgcttgagcc   4080
caggaggttg aggctgtagt gagtcatgtt tgcagcactg cattccagcc tgggcgacag   4140
agcaagaccg catctcaaaa caaaacaaac aaaaggtgaa attttggaat taggaaagat   4200 gctatttta  taaattggct ttaagctgtt ggctggacat ctaagttgta gcattctgaa   4260
ggcagcagag atgtgggatt gtaggactga aacatgaaaa tgcctatcga attttttta   4320 aagtctttaa aggagagctt taaggaaag  caatacgaat tcaagtatgt ttcagtacca   4380
ctcctctctc taaagacaat caactatggt tttcattcaa aatactatta ctctaacgtt   4440
aaatatttga gtacagcaat catttcagat gcattatgaa taagttactg aacacgcctc   4500
ccatctgctt gctttacggt tttatttgc ctttcgtttg ttagctcatt ttataatttg   4560
ttacttctga acaccttcca agtgctggtg ctttcagata tctacctcaa agtattattt   4620
gtaaatgtca aaagtccct  cttacatata attgaaagct ggctacatgg tagacaatat   4680
gatcacaaac ttttaaacaa ttttttaagc tgaagaaata cttttctttt ttataagtat   4740
caaatcaaaa tgtaattcag catccaccca taaagcgcaa ctaaaaactt tcacaatgc    4800 cattaacaac ttgtggttac catcataagc ctacagacct acacactaat tatctttaaa   4860
acccttatta ggctgggcgt ggcggctcac gcctgtaatc acagcacttt gggggccaa    4920 ggcgggcaga tcacttgagg tcaggagttt gagcccagcc tggccaacat agtgaaactt   4980
catctctgct agaaatacaa aaattagcgg ggcgtggtga cagggtgctc taaccccagc   5040
tacttgggag gctgaagcag aaccacttga acacagccag gaggcagagg ttgcagtgag   5100
ccaagattgc accactgtac tccagcctga gccacagagc aagactccgt ctcaaaaaat   5160
aaataaaaat aaaataaaac ccttattaag gatttaaaaa atcttaatta tataatgcca   5220
aaagctagtc cccgtctggc ttaggggccc acaagctcct gctttaaagc cagttttttt   5280 gttttttttct gatgtactta catttgtgcc tcacaatcaa gaggttccca gcttggtgga   5340
```

```
actttcaaag atgaggcaga aaactaaaca ggcaattaca atcttacttt tcacgctgac    5400
aagtggtacg gtggctagcc caaactcccc tccctgtccc agctacctcc cttatagacc    5460
attcacgatc acttaggcca ggctgccatg tgacctaaga gaagacaggg agaacacagc    5520
atttcttact cctactaact tgcaacatca ttctctcaag ttgctctcat tggaggctcc    5580
caactgcttc aagctgccca gtgatatttg tatttctaaa gtgggcaggc atggccattc    5640
cagaaaaaga aacacattca gacttgtgcc ttttgttacc caaatatatg atattcaaat    5700
aatttctatt ttaacaactc ataaaaattt aagatcaaat aattgcattc ttgaaacaat    5760
tcttaatcat ttatttttcaa cacgtgtact ataaagaacc taagaaatca gacaatttta    5820 ataaccata aacatgttga atccatttgc agatttaaat tttgtaaaaa tagctgtcac     5880
tgcctccata tatcaagtgt actatgttta taatcacatt tatgctaccg atactcctca    5940 gaaaaaaca gattctgctt ggttctagct tcagtattat gaactccaat aatgctttga     6000
ggacctccaa aggaaaaaaa cagattctac taggttctag ctgaaatatt atcaactcca    6060
aattgaagct gaagtattat caactccaaa taatgcttcg aggacctcca aaaaaagag     6120 attctgcttg gttgtagctg aagtattatc aactccaaat aatgcttgga ggacctccac    6180 aggtaaaacta ctaatcccctt tggccattta ttgagacaga cagagagaga gagagagagt 6240
tttgaagcaa caatgtacca ttagtaaagt tgctgtgcag aattacctca gtcctattct    6300
aagcttacag ttcagttgat tttattgtct tcacctaagt atatacaatt cacatatggg    6360
agaaaaacac taaatcaaga tggttatttt cactgttttg cttaagattc atatttaaat    6420
ataaatcaag aagttaatcc acagtttgag agatacttat attagaaatt ttaaatgtta    6480
aatacataat tgtaaatatg gtgtatgtac tgtttcacat acaatgggta ttgatcaaat    6540
cagtgtaatt agcacaccca tcagctcaaa tatcatttat ttgtagcaag aacattcaat    6600
acattaacta tagtcacccct actctctctc tctctctctc tcaataaatg gccaaaggga    6660
ttagtacttt tacctttgga ggtcctcaaa gcattatttg gagttcataa tacttcagct    6720
agaacttatt ccttcaaatt taactctgta cccattaaaa gtggttttgt gtgcaattaa    6780
cagacacatg ttctacccat acattgtttt ccaaaattat tgtgtggctt taaaaaaaaa    6840
aaaacccaca caacaaattg caaaaggcac tgagataaca tctgcttcta gatcattgct    6900
aggctcgaaa aataaagctt gttctaccag gaatgacaag ttagaactta gtatttgcca    6960
aagcagaaat tatatagtgt cagttatttc aggcaaacct tattcggctc tcatccccaa    7020
ctatctgtca gaacaattaa aagagatcaa aacagtccag cataactagg cttcattata    7080
taaggccatt ttgttctaag acactaataa accaaaataa gaaatattaa aatcaaaata    7140
aaagatatta tttgagctat tttcatacaa actgttggtt ccttatatcc tcccttctat    7200
aataaagggc atatttact gcaaagaaaa ttttactttta tatatcac tagccataaa      7260 tttttgaatg tcattaatta catgttgtct agtaccatta accaaatagc gtaactattt    7320
tatgtccaca tttcacttct gtatttacaa acatatcagt aaagagttaa caatgagatg    7380
cgatcaaaca tccatattat ctgttttgta gacagcaatg tagatgattt tgtaatcacc    7440
tttcatcgga gtgaccttat ataaaaaata agtcaataat ttagaggttc taagtctcca    7500
aaggagattt tcaaatgtaa atatagaaat ggttatagat aatgagattt ttaggaaacc    7560
tctgccatgt ctgcatcctg ttaactgtta tatcatcttt tcttccagct gcgttccttt    7620
gcctgcaaca ggggtcaaga tgagttttgc ctgacttctt tgatgtcctg aactttccgt    7680 agtcctttttt cttgaatttg ttcattataa atatagcttg gcatttgttt gatctttca    7740
```

```
actgtcttca ctgcatcagt agttttattc catagttctt gcagatattt gacaggcttg   7800
ttactatatt tttcaaattc aaatccactg taagctcatt attagcagtt gctttacaga   7860
atgctttagt ccacctaacc ttttgagaat tgcacttctt ttaaagttttt tgtgacattt   7920 atgtttatac aatctgaaca ccttgcaaca gctgcagatg aacatcatga tgtggtcagg   7980
gtagatgggt cccaaagaaa ctaacacttc tcagtgctga gctcggatgg gcctccactg   8040
accaaacacg gagcttgaga ggaagtcaag aggtatcttg gaattccaca tgctgaccct   8100
gtcattcttg aaggaaaatg atgcataatt tctgaataat tcagaaagaa cttaacaatc   8160
tttccagtta gtttttaaat aacaattctg tttatcaaat ttctgaatta acttttctga   8220
attcacgggt ttctaaaact ggccttaagc aaaagtctga aacctaggct gggaaccatg   8280
taacccaggc caagaaggta ctttaaagtg tcttagagtt gttttttcaac ttaggggaa   8340 acaacagatt ccattaaatc ccataaagga ttttttttgtg tgtgaaaaag ggcctgatgt   8400
aatctaggtt agactcagga ggctttaaca agttttgtct tacgggtaaa tggtggctat   8460
tttcacagat aacatcatta ctcccatccc ttactatggt ttatacaaaa gaggctggag   8520
aataagtaca ttttttacagc cgggtgtggt ggctaacgcc tgtaatccta cttagcactt   8580
tgcgaggcca agacaggagg atctcttgag cccaggagtt cgagaccagc ctgggcaaca   8640
cagggagacc ctgtctctat tgttaaatca agaaaaccta aaaaacattt tcatttacat   8700
agcaccaaat ataagagcct tttttttttt aacctagaaa gagtattttg gagagagaaa   8760
ctaaggatca gaaggtttaa gagtatcaaa aatctgaggc caggtgcctc acatctgtaa   8820
tcccagcatt ttgggaggct gaggtgagta gatcacttga gtttaggagt tcaagatcag   8880
cctggctaac atggtgaaac cctgtcttta ctaaaaatac aaaaaaatca gctggtatgg   8940
tggtacatgc ctgtaatccc agttacttgg aaggctgagg caggagaata gcttgaaccc   9000
agaaggcgga agttgcagtg agccgagatc actccactgc actctagcat gggtgatgga   9060
gcaagactct gtctcaaaaa aaaaaaaaaa aaaaaaaaa aagagtatct aaaatttaaa   9120
tactaattct tggctggaca tggtggctca catctgcaat cccagcactt cgggaggccg   9180
aggcgggtga cctcacttga ggtcaggagt tcgtgaccag cctggccaac atggtgaaac   9240
cctatctcta ctaaaaatac aaaaattagc tgggcatggt ggtgcatgcc tgtaatccca   9300
gctgctccag aggctgagcc aggagaatgg cttgaacccg ggaagcggag actgctagat   9360
catgacactg cactccagcc tgggcgacag agagactcat ctcaaaacaa acaaacaaac   9420
aaacaaacaa aaaaacaaaa aactaaatct ttcacacatt ttctctttat atcaaaggta   9480
ctaagtgaca tttaggccgg acgcggtggc tcatgcctgt aatcccagca ctttgggagg   9540
ccgaggtggg cggatcacga ggtcaggaga tcgagaccat cctggctaac acggtgaaac   9600
cctgtctcta ctaaaagtac aaaaaattag ccaggtgtgg tggcagatga ctgtaggcca   9660
agctaattgg gaggctgagg caggagaatg gtgcgaaccc gggaggcaga gcttgcagtg   9720
agccaagatc acgccactgc actccagcct gggtaacaga gcaagactcg gtctcaaaaa   9780
aaataataag ttacatttaa atgtcatata catatttaag aaaaaaaaa accaagtact   9840 tctcatttaa gacagagtag aaattattta aaattaggag ttggtgtaaa ggatgagcta   9900
catattcaag tcaaattata gtaagtattc actattccac taccaaagta ggtcaattat   9960
actaaagaga agaaatctat gtgaattgag gcattttctc actttgatat atgtgaataa   10020
atttcaggtt gtctaaattc ctagggttat atagttagaa atatataatt ctcttataga   10080
```

```
caggtcaact aggggaaata agttagcaca atcatttgaa ttggttgtct acatactggg    10140
cagggcttat tccttttctt tagcttcttt gcacatgtaa agcaggccat aagatgtcct    10200
gttttgccat ggacaatgca accattttta ggtcgacctt gacaaatcac acaaggttca    10260
atggcattaa ggggcaaact agattccaca ctctcttctt tgtcttgggt ttcttccctt    10320
tcaaactctt tcacatcttc ttggctgcta taaataatgc tactagaagt tgatggctga    10380
gaatagtctt cactttcttg tgattgtgaa gcttgtgtaa ttttatcatc attttcctca    10440
acacatgact ctctggaatc attcactata gttttttac aatcaggaac atcaaagccc     10500
tcttcagctt gtgttgagtt ttccagtttg gctttctcag agatttcccc tttatctttc    10560
cctttatctt caggaagcca attctcacga agggcccaac atctgttgca atgtgatgga    10620
agggggggat tcatttcatt gcatgaagtg catttccaat agtccttcaa tgaaataaga    10680
cacacagtca gtttctgtaa cccttaact gctcagtcac aggaatgcta gcaactttgc     10740
tatgtctaag gtaaagtata tcataggct caatattcag tgtttcatgt tttatataaa     10800
atagtcactg taaacagcat gaggactata gttagttata tattggtata ctggaaattt    10860
actaaaagaa tagattttag gtattttaac catacacaca agaaaggtta actattcaag    10920
ataatggatt acattaattt gcttgactgt agtgatcatt tcactattta catgtgtgtc    10980
aaaacatcac gttatatgtc tcaattatac acaaaacaga ttttaaagg tcaatatgta     11040
acagtctctc ctaaagtaga gtaagtacac ccatttttt cacccttacc atcctgaaaa     11100
attctaaact aaaaatatat taactgtgat gtgatattaa tcatgtacct ataaagttat    11160
ctgtttcagg atacaaatgc agttgcttcc tttagttgaa gcaagtctat gggatctttt    11220
actctgtcat gcagcctata tccactccct taaaggctca accctaggcg ctattccaag    11280
agtccatccc atcaatctag atgaaacctg cctcctcgag aaagacttcc taatccacca    11340
gtgactagaa ctaccttaga agtactctaa aaccatggct taactgagta ttccctaact    11400
ccatccacaa gagaaatgct aaaacatttt tcacagcaag tattgctgct aaaacctatc    11460
atccttggtc actaaccgta atatcctttc ctttacctgt ctatcctttc ctgtgttctc    11520
atctttgtaa ctgctcaatg cttcttcctt ttcccaacgt tttatcccac aaaccttcc     11580
accatgcaat ttggataaca aactctccca catccccagc ctttttacat aacctatctt    11640
cttgccttag ctgaagcatg gttccttgcct gaggacattt aacaagtgaa aactcttaag    11700
taagaggtat ttccgtaacc attttgagat tgcctcacaa atgatgttaa gacaggagca    11760
ataaagatag actattcatt cttctttttt caagttatag aagggggttt ttcacagctc    11820
ataaaaccaa agaaaaggt cttgcaatat gggagtaaaa gtgcatcaaa aagtccaata     11880
aattccaaga tgaatatcta aaataatttg agtcttaaaa tagatttaaa aaattaaaag    11940
tatctaaaat atttactca acttgacatc aaatgattca attagttatt tatttctaa     12000
tacagtaaaa attttggaaa ctcttgaatt ttcatccttt tttgcacttg ataaattagt    12060
aactgtctat aactcagaaa aaatggaatt tatttcctat tcaaatataa taaaggcaat    12120
attaagaaca aaaactaaag cacaatagtt ttaaaaaac ctataatacc tcaggaactc     12180
agtgaagtat gcatgagatg taaacattta agtgttaatt tctttaatgg caaatcctac    12240
cacattctat aatacaaatc agtaataaaa atgtttacat ttggctgggt gtgatggctc    12300
acacctgtaa tccttgcact ttgggagact gaggcaggtg gatcacttga gcccaggagt    12360
tcaagaccat cctgggcaac atggtgacat ttctacaaaa aatacaaaaa ttagctgggg    12420
tgtgatggca tgcacctgtt attccagcta ctcaggaggc tgaggtggga ggatcacttg    12480
```

```
agcctgggag gtgggggctg cagtgagcca tgatcacatc actgcactcc agcctggaag   12540
acagggcagg accctatctc aattgaaaaa aaaaaaagtt tacgtttgac aaggttggca   12600
aaatgttggt aatagttaaa gctgggtgat gagtatactg gagatacact gaaattttcc   12660
aaaataacat caaaatgtac aaattcagct gggcagtgac tcatgcttgt aatcccagca   12720
ctttgagaga ccaaggtggg cagatcactt gaggtcagga gttcatgacc agcctggcca   12780
acatggtgaa accccatctc tactaaaaat aaaaaaatta gtggggtata gtggtgcatg   12840
cctgtaattc cagctactca ggagactgag gcacgagaat cacttgaacc tgggaggtgg   12900
aggctgcagt gcactgagat tgcaccactg cactccagct gggagaagg gtaagaccct   12960 gtttaaaaaa aaaaaaaaaa aagttcaaat tccagcacct aaaaataaaa attatagcta   13020
caggtctcat cacaacaaat aaaagaaaaa tgctttaaat tattcagact ttacaaaaac   13080
attttaactt tataaaaatc agttcatttc agaagaagc tagatatagt ctcctaatct    13140
tgaccttaat gaaattttta tttcttaaaa aagtagatgt atacttacag ctaaggaaat   13200
ttcaggatct tcttcaaatg aatctgtatc actctcccct gcctgataca cagtaacttg   13260
atatacctaa taaacacat tcattagcat caattcatcg ccctatttcc ttcaatcaga    13320
aggcttccta gtaataagtc ctaaacaaat atcatgtact acaatatatg agaaagcctt   13380
agacaatatc aaatagagta agtgagtgta aaggggaaa aaatggagga gagagaaatc    13440
cttacccaca atggtaaaag tcaatacaaa ggatgtttag gatgaataaa acaaaacatt   13500
cagctaggtg gttttacttc ataaataact aatatggaga tattaaataa tagggaaata   13560
gctagaaatg ttaaaggcag tcacttctgg gaaacagatc tctaagggta ctacttgact   13620
ttaactgtat gcatgtttta cttttataga aagtaagtta atattaaaac agtagttgaa   13680
ttatatgttt ttaaaagtga acagaccatt ataataagca tgttcattga ggtctattga   13740
cttcttggca attagtagta atataataat ataaatcaga tgataaagaa ctatgaaatc   13800
ctcaagtcca caaccaatg tgttagttta aacaaatcaa gaggtaaaga tttcaagtga    13860
aatctgaata atattatttc aatctcaaag tcaatgaaca tagaaaatat ttaataattt   13920
tccaatataa ttagagggga aaaaaatac tacctcatca tcttcatctg agagttcttg    13980
tccttcttca ctaaggctat aatcttctga gtcgagagat tcaacttcaa attctacact   14040
aaactgatct gaaactgaat cctgatccaa ccaatcacct gaatgttcac ttacaccagc   14100
atcaagatcc taaaacaaga aaaaaatata taacttaata aacatcaccct cttgacctct   14160 gtatctgttt cctaactcat ccctgtgcct ctgctgctgc cagcagggtg taacagttgg   14220
gggatgggcc tgctgctctg atccgggact tcccgaggga gatcggcggg cagaagacta   14280
ggccccccag ccagccatcc cggagccggt tgccacgcac atttcctcct cagatccatc   14340
ctgcatactg aaactagatt aaggtttcaa ggttattact acattatttt ccctgttcaa   14400 aacccccactg cataaaggaa aaacaccaaa gcctcttggc atcgaaagta cctacagtgt   14460
gactgtatta acatcttcgt ctgtcttcaa ctagacaccc ctcctcccctt actaaatatg   14520 gataatcccg ccagatctag attgcttcct caactaatct tggcatttca acttccacac   14580
tttccccctc taactagaat aatttcagtt tcaaaatcct attcatcctt ctttgactaa   14640
gcctttgtca ataccataac tgaaaaggct cttccacctt taattatcct tactacttgt   14700
ataataatga attatatagt ctcacacata aattatgcaa aacataattt tgcaggcatg   14760
tttctcatct gaattatata tactttgagc taaaacctgt cactcatctt tctatgtcca   14820
```

```
aattggtaga atacacgtaa caagacacaa cacttgtaat acttatgggt ttttttttctt    14880 agaaaaatgt ctcgagtcat agatacttat gttttttaat aaactttgag attttctttt    14940
aaagagcctt tagacaatta aaaaaaattc tgtagctgct catctgattc ttcgtttcag    15000
gacttcaata aattgtataa gaacctagta agaccttcag ggcaataata tttgctgtca    15060
gtggctaagg gtaggagcat atataagcag aaggctacaa ttggaaaaag tctagaagtc    15120
gggatatggc ttattctaca cttgccacta agtagctaat ttaaccttaa acaacatcat    15180
ttaacttatt ttatttattt tgagatggaa tcttgctcca tcacccaggc tggagtgcag    15240
tggcctgatc tcagctcact gcaacctaca cctcccaagt tcaagcaatt ctcctgcctc    15300
agcctcccaa gtagctggga ctacaggcgc atgccaccat gcctggctaa ttttttgtatt    15360 tttagtagag gcagggcttc accatgttgg ccaggctggt cttgaactcc tgacctcaag    15420
caattcaacc gccttggcct cccaaagtgt taggattaca ggtgtgagcc accatgcccg    15480
gccctttttt ttttgagac aagagtcttg ctctgtcacc caagatgaaa tgcagtggca    15540
tgatctcagc tcactgcaac ctccgcctcc ggggttcaag ctattctcct gcctcagcct    15600
cccaagtagc tgagattaca ggtgtccact accacacccg gctaattttt atgtttttag    15660
tggagacggg gtttcgtcat gttggctggg ctggtctcga atcctgacc tctagtgatc    15720 cgccacctcg gcctcccaaa atgctgggat tacacctgtg agccacctcg cccagcccat    15780
atcatttaac ttctaaaggc tgtagctact tcatctagaa aaggagctta gattaaatga    15840
tttccatatc tgtatcagtt ttaaaaacag aaacaaagta tattatttta cagcctctga    15900
catcaaaaga ctttttttaga gtaatgttag gaaggagagt aaaagcaaca ttcatcaagt    15960
tgcagctcaa attcctaaca agggctctac taccaatcag attagaatca caagtcaagt    16020
taggatacaa ttaacactaa caaagtaacc caacaaacca aatacttcaa ctaactaaag    16080
tctttagtgc actaattta gaataagggg gtaaatcaca agaaacatta aatctcagaa    16140
aacatactct acgtaggggg tctgcaaact gtggcccatc acccatcgac ttttataaat    16200
aaagttttat tgaacacagc catgcctatt tgttgacttg ttgtctacag ttgctcctgc    16260
attacaagag cggggctgag tagctgtgac agaaaccatg gcccggcaga gcccaaataa    16320
ttaactatgt ggctctttac agaaagtttg ccaactcctg tcctaggata ctataaaaat    16380
actataaaaa ataccatgaa aaaatgcaat attgggagtg gttttttaaag ttttggctaa    16440 tgttcgcaaa agaatgcccc agaaactatt aaattatctc tctctatata tattttttaaa    16500 atatataaaa taaatatttta aaatatatat ttatatttat ataaatagta atatatataa    16560
tatatacagg tgcctgccca tttatattta cataaatata tattttttata tttatataat    16620 tatatttta tatttatata aatatatata tttatattta tataaatata taattatata    16680
aatatatata acaatgtaat ataataatata cattaatata taatagattt ataattatat    16740
attatatatt tatacattat ttaaatataa atatatatat atatatattt tttttttttt    16800
tttttttttt tggagacaga gtctcgctct gtcacccagg ctggagtgca gtggcaccat    16860
ctcggctcac tgcaagctcc acctcctggg ttcacgccat tctcctgcct cagcctcccc    16920
agtggctggg actataggtg cccgccacca cgcccggcta atttttttgta tttttagtag    16980 agacggggtt tcgccgtgtt agccaggatg gtctcgatct cctgaccttg tgatccgccc    17040
gcctcagcct cccaaagtgc tgggattaca agcatgagcc actgcaccag acctaaatac    17100
tatatattta aaaagcatca ggctggaggt ggtggctcat gcctgtaatc ccaatactct    17160
gggagccaaa gcaggagaat cacataagcc cagcggtttg agaccagcct gggcaacagg    17220
```

```
ccaagatctc atctctgaaa aaaaaaaagt aaaaaaaatt agccaggtgt ggtggtgcac    17280
acctgtagtc ccagctaact ctcaaggctg aggaggaagg attgcttgaa cccaggaggt    17340
tgaggttgca gtaagccatg atcatgcgct gcactcccgc ctgggcaacg gagtgagaga    17400
ctgtctcaaa aatttaaaaa atatatattt ttttaagcat cagataggct tgctctgcaa    17460
agatcttaga tctttgtagt caaaaatacc tagaattgtt tgaattccaa ttgtgacaat    17520
tagttgtagg aaccttaaac aagttattta aaacccagt cttagctaaa aatgaatct      17580 gaggctgcaa agatgacaga agatcataat ataaactgca tggtgtacag tctagaacac    17640
agtcttagtt tcccacaatt tattaaaccc caaagaaaga aaagatggga gaggaatgca    17700 cttccttta  actcccttca caaactggtg aatgatgaca cccaatgatg actacaacat    17760
tctcaaatga gggaaattaa aacgaagaag aaaaaaaaac tggccctacc aaaagctttc    17820
acaactaggg acttaacctg aaaaacgaga ttttgttgtt gttgtttgag atggaatttc    17880
gttctcgttg cccaggctgc agtgcaatgg cgtgatctca gctcactgca acctccgcct    17940
cccgggttca gcgattctc  ctgtctcagc ctcctgagta gctagattac aggtgcccgc    18000
cactatgccc agctaatttt tggtattttt agtagagatg ggttttcaca acatgttggc    18060
gaggctggtc ctgaactcct gacctcaggt gatccgcccg cctgggcctt ccaaagtgct    18120
gggattacag gcatgagcca ccacgcccgg ctgagatttt ttatagatag gattttttaa    18180
gagaatgcag gacaggacta acaaaaagaa aaaagaaat  acccctctac tccacacgag    18240
ttattaagaa attattttag gcaaatggag aggaaaagtg gtccttggaa ggttttttcgt    18300 agctccagaa aaatttcttg tctagcataa aagccctggc tcttaaaggc tggcaacctt    18360
taagatgcaa atgcaagagg gtccacccaa catggcgatt cccaccgttg tcctcttgcc    18420
cttgctccat caggtaccta acagcatggc cgcccccaca taaccccgtg tgtaaaatgt    18480
catggcatcc tgcatttgtg tattaaagga ctggggtggg agggccagtt ttcttgaggg    18540
ctaaatgaca tgcctggtca aaccaatcct ctgagcccta tgcaaataag acaccacccc    18600
ctccagccgt cacataaaac tggctagtat tgtcagaatg taaggtctcc tctttcagct    18660
ttagagcccc cctccctctg tctgtgtaag ggggagcttc ttccttctgc cttctcccttt   18720 cttgcctatt aaacgctctg ctccttaaaa ccactccacg tgtgtccgtg tcgttttatc    18780
taattcaact caaaacaaaa aacctggtgt tcctctactc ctcaaagcca tatcagtaac    18840
aaggcagtgt cccaggtaca aagcaggaac aaggactcta aatatcattc agctagaatt    18900
ctgatataac tttaacaaaa actatacatt aaatagggg  ccgggcaggt ggctcacatc    18960
tgtaatccca cactttggg  aggccaaggc aggcagatca cttgaggtca ggagctcaag    19020
accagcctgg ccaacatagt gaaaccccat ctctactaaa aatacaaaaa ttagccaggt    19080
gtggtgatgg gagcctgtaa tcccagctac tcaggaggct gagacatgag aatcgcctga    19140
accggggagg tggaggttgc agtgagccaa gattgcacca ctgcactcca gcctgggaga    19200
cagagagact caatctcaat aaataaataa atagggtata ataattctct ttttaaccaa    19260
acttgtaggt tggatactca tcaagttta  attggattca attttatcac atatattcc     19320 gctcaagagc ctatttttc  cactggattt attaaatgtt ttcattttg  tcattaatga    19380 tctatctccc aatgaaggca agaaccatat ctaccttgac taccactgta tctgcagtgc    19440
catctcaact gtatggaatt tggtataaac ttaaatatct acaaatgaag aacctgctct    19500
cagactgagc aggagctcat catgccatct agcggtctac ataagtaaca gctccgttag    19560
```

```
gtacagtaac tctagagggc aggtatgcgt tcatacaatc actgctttgg aagagaaaaa    19620
aagataatac aggaagtaac aagaataggt aaaagactag gattactatc acaattggtt    19680
ccacttccta catcttctag agtactatac aatgattact aatacccaga ataatggcca    19740
tgagacactg ccatattacc aaaaaatgta tccaatcctt tggtttccgt gggcgacatt    19800
ggaagaattg tcttgggcca cacataaaat acactaacaa tagctgatga gcagaaaaaa    19860
aattgtaaaa aaaaaaatca taatatttta agaaagttta tgaatttgtg ttgggccaca    19920
ttcaaagcca tcctggcata tggcccacag gccatgggtt ggacaagctt gattaaagac    19980
atacaaaaca aaatattcca tttgtcaagc attcttgtta acaaaaaaat ttttttaccaa    20040 acttctttca gtgacatctc ttaagaaatg ctgctcacta atattttgga agtctgtatt    20100
agtaatgaga aagtactgat actctcccgt catccatgca ataataaacc tgcatttttt    20160
tttttttttt ttgagatgga gtctcgctct gtcacccagg ctagagtgca gtggcacaat    20220
ctcagctcac tgcaacctcc aactcctggg ttcgagcgat tctcctgcct caggccccca    20280
agtagctggg actgcaagca tgcgccacca cgcctggcta ttttttgtat ttcagtaaa    20340 gacatggttt catcttgttg gccatgctgg tcttgaactc ctgacctcag gtgatccacc    20400
cgcctcagcc tccgaaagta ctgattacag gcatgagcca ccgcacccag cccagtataa    20460 acctgtatt tacagcataa gtaaatagaa cttacctgat gtctagacct atttggcaaa    20520
tgttaagttc agactatgct gacttttttg ctgatggctg taataaaata tattttttact    20580 ctaaatagtc aaatttgcct taaaatgcta aaatatttaa ctgaaccaaa tttttggttt    20640
tgttcctttt ttaaaaagtg taactctcaa attctcaaac aactctatac tccaatttat    20700
ttgactgtac tattggtgca gtggtccaca aatattctct aatacataca gtgacattga    20760
taattactaa tactactact aattttacca ataccggtgt tactccacta ttttccacat    20820
ttctcacaat accttgggtt gaaggtggag atcaatatag tagttttatt ttaaagtaaa    20880
atttagcact gtgttttcta tcaatctcgt aagacacatg tacattctat ccgtatcctt    20940
attaggactg ccaggactag actttgaaca gtaagagtct tgccttactt aaaatgagaa    21000
cattaccgga ttcgatggcg tccctgtaga ttcactgcta ctgcttcttt cacaacatat    21060
ctcccttatt acacacagag ccaggctttc atcaaggaa agggaaatac tatcagattt    21120
gtggcgtttt ctttgtcgtt caccagataa ttcatctgaa ttttcttctg gatatgtaag    21180 gaaaaaaat aaattgctgt actgtgattt agaaaattga gctgttttga gtacctatttt    21240 gtacagaaac ttagtttcaa taaaattagt tcaaaagtta acactgtttt attgaatctg    21300
tccaactgtt acagcagaac actatctgtg tgtatttatt tatttgttta tttatttatt    21360
gtctgagaaa gggtcttgct ctgtcaccca ggctggagta cagaggcaca atctcggctc    21420
actgcaacct ctgcctcatg ggctcaagtg atcctcccac ctcaacctca gcctcccgag    21480
tagctggtac cataggaacg gtaccatagg aatgcaccat tttgtatttt ttgcatagac    21540
agggtttcac catgttgcct aggctgagaa tactatttt aaaaagcttt ctattcttct    21600
ttcagaactt tatctccata catcacaatt taatctatct aataaagttt ttattaacca    21660
aaaaatctag gaattttttt ctgtcaaaac caaactttaa aatataagag ctcatctgtt    21720
tttttccgaa aagagccaaa gtgtttaatt tactcatatg gtattcttaa tgtttcaatt    21780
tcttcagtac cctacacttt ttcttttgag acagagtcac actcgaccac ccaggctgga    21840
gtgcagtggt acattctcag ctcattgcaa cctctgcctc ccaggttcaa gtgattcttg    21900
tgacttcagc ttccaagtag ctgggattaa aggtgcacac caccatgcct ggataatttt    21960
```

```
tgtattttg  gtagagacag  ggtttcacca  tgttggccac  actggtctca  aactcctggc   22020
cttaagtgat  cctcctgcct  cagcctccca  aagtgctggg  attacaggcc  taagccacta   22080
agcccggctc  ttcagtaccc  tatattttaa  acagaaatca  aaaccagtaa  aaagtttcca   22140
tttcatttta  aataataaat  tatctctgaa  tgggtcagaa  tgttagacaa  atccgttaga   22200
cataaatgag  aatactacct  tatactagac  ataaaaatga  attccaggtg  gattaaagat   22260
ctaaatataa  agaacaaaac  cattcaagta  cctataacaa  aatattctta  taatgctggg   22320
gtggagaagt  atttcataat  actgcaaagt  cctcaataaa  aagactatca  agattagacc   22380
atgtcaaggt  ttacatgaca  aaataaaata  ccaaacaaaa  gttaaaaggc  aaaggtcaaa   22440
ttcgaagata  atatctgcaa  catatatagt  aaaaattacc  catagtatac  atattataca   22500
aagtcctacc  aaatcaagat  agactgtatt  ttcttttaag  gaaacaggaa  aaagcaagtc   22560
acagaagaaa  tacaaatgac  taataaacat  atgaaaaatc  ttgagtcatg  tacttgagta   22620
atagaaaaaa  aaactcttac  ctcctaggga  tcaaagaaat  gcaaagtgaa  atgatatcat   22680 tttcaccca   tgagaatgac  aaaaattaaa  atgagatagt  atcacagatt  tctgaaagga   22740
ctttttttat  cattttcttg  agacaaagtc  tcactcttgt  cccccaggct  ggagtataat   22800
ggcacaatct  cggcacactg  caacctccac  ctcctgggtt  caagcaattc  tcctgcctca   22860
gcctcctgaa  tagctgggac  tacaggtgcc  caccactgtg  cccggctaat  tttttttgta   22920
tttttagtag  agacggggtt  tcaccgtgtt  agccaggatg  gtctcaatct  cctgacctcg   22980
tgatcctccc  tcctcggcct  cccaaggtgc  tgggattaca  ggcgtgagcc  actgacctg    23040 gccgggattt  ttacgtttta  tcgagatcac  aagttctgca  cgtgagttct  taatcatgtt   23100
tgtgttccct  attttaaaa   aggtgatctt  ggccgggctg  caattataaa  taatgctgta   23160
attagtatct  ctacatataa  atctttgaat  ttttattac   atccttagga  tagattacta   23220
gaaatggagt  tactaggata  atgttaagaa  ctctaagact  ttttttttctt ttcttttttt   23280 tttttttta   agagggagtc  tcactctgta  ccccaggctg  gagtgcagtg  gtgcgacctt   23340
ggttcactgc  aacctccaca  tcccaggttc  aagcgattct  cctgcctcag  cctcccaagt   23400
agctgggatt  acaggcgcct  gccaccacac  ctggctaatt  tttgtatttt  taatagagat   23460
ggggtttcac  catgttggcc  aggttggtct  cgaactctta  acctcaagag  atccacccgc   23520
ttcggccttc  caaagtgctg  ggattacagg  tgtgagccac  cgcaccaggc  catctaagct   23580
tttttataat  ccgaaaaatt  taatcaattt  ttacccactt  ttaccaattt  acagaccaac   23640
agtttatcag  tgctaataca  caagttatta  gcactgatga  gtaaggatga  gtaaaatttt   23700 tattttact   aatttgatag  atcaaaagga  cacccttttg  gcattttta   ctatctgtaa   23760 agctaaaaat  caccaaaatt  caccctctcc  ccatatttat  tagtcattcg  tatttactgt   23820
gagaaatttt  tgtgaactgt  ctgccctttt  tgctatttga  agttttaatg  ttttccttat   23880
tgatttggga  agacttttta  tgtaatacag  atattaacag  tcaaatttaa  agtgactatc   23940
tttcaaatat  gttgtattct  attttcatt   taactttaa   actcatttga  aattcatttt   24000
ggcataaggt  acagatctaa  cttcacctt   tcccaagta   actaccattt  gttctagttc   24060
cacctctgcc  ctagacacct  ctgccttcc   tgtcttctgc  ccgcatgtac  gagattctgg   24120
tctgggttca  tttattctgt  ttcactgatc  tgacattctc  tttcatctga  atcatacggt   24180
cttagttact  gcgacttcct  caggcaacag  ccttctcgtc  tactacgtct  actaactgtt   24240
ctcaactatt  ttctctctgt  caactatttt  ctctctctct  ctttttttta  gacagtctca   24300
```

```
ctgtgtcgcc caggcggagt gcagtggcgt gatctcggct cactgtaagc tctgcctccc   24360
cagttcatgc cattctcctg cctcagcctc ccgagtagct gggactacag gcacccgcca   24420
ccacatccag ctaatttttt gtattttta g tagagatggg gtttcaccat gttagacagg   24480
atggtctcga tctcctgacc tcatgatcca cccgcctcgg cctcccaaag tgctgggatt   24540
acaggcgtga gccactgcgc ccggcccta tctcttcatt tctaaaatgc tatttacttt   24600
ctgttttaaa actcataggt atgtactacc atttattaaa aataacaatt taaaaattta   24660
actgttaagg tgactaagaa taatggtgaa aatagagttt atatgcctgt ctcctattat   24720
ctttcttttt agacgaagtc tcacacggtt acccaggctg gagtgcagtg gcgcaatttc   24780
ggctcactgt aacttctacc tcccggttg aagtgattct ccttcctcaa cctcctgagt   24840
agctggatta caagtgtgcg ccaccaggcc cagctacttt ttgtattttt tttagtagag   24900
atggggtttc accacgttgg tcaggctggt ctcgaactcc tgacctcgtg atccgccagc   24960
ctcggcctcc caaagtgccg ggattacagg cgtgagccag gcgtgagcca ccacacccca   25020
gccacctcct actatcttaa cagagagttg gctaactata aactccagtg gggcacagta   25080
aactgtgcct gctgtagtca gccagaaaaa tattgctaaa taagcaattt gtaaatcaaa   25140
taaaatcacg aatgaaaaaa actcagaggt taattcatct caaccaaaaa aagggaacaa   25200
tttaattaag tctaaaagca ctaatttcat tagagaaaga atatcaaaaa gctgtgtgaa   25260
tgcgtcaaat aaatattcat atatacctgt ctcactaatt gctctccttc tagatgaggt   25320
agatggtcta gaaaccaaat gtgaagatga aggtttctct tcctgaagct cttgtacaag   25380
gtcctaagca tttaggaaaa aaataaaata caacaaactt aacataacca gtaagctaac   25440
ttgttgtaaa taacctttcc aatttgcaaa taatattaca ttagaatgag aaatttactt   25500
agattacctt ttgatcactc ccaccttcaa ggtgacacct gttctcactc acagatgtac   25560
ctgagtccga tgattctgag agaaaagaaa aaggatcaga aacttggtgg tgggcggggg   25620
gcggcggggc gctactcagt agatatgcta tcagtctaac acaaacccctt atgcaattta   25680 acctttcaat aaacattaaa catgtatttt ccaggtggca tcctcatact aaatgttgca   25740
gatgtaaata aaataattca actttaatgt agaagagtaa agtataatca agacattaaa   25800
agactgttag ataaattagc agagagacag gagagtcatt attttggtag ggacagggag   25860
tgtctgagaa acaaagaatc aggaaatatt ttgtaggaca atatgaaaat agggctagga   25920
aaggccattc cagaccaaga aaacgccatg tgaaaaagta tccaaaagca aactaacaac   25980
agttcctgtt gcaggacacc acaagcagtt cattattact ggaatgtagg caggttcaga   26040
ctgtaaagga tcctgtggtc tagccaaagc aggactcatg ctgtcattcc cttatcactg   26100
cattcttccc cgcagatact tcagaatctt ccttaatgcg atgttgcagc cactcaccat   26160
taaaaaggat ttttgtccaa gaaatgaaac tgatttctag ctcacagaaa atattacatc   26220
cagagagcaa taatgaaccc ctaaatggta atttttaagca gaagagtgac aaatcactct   26280
agcaaaacat aagaaaaaga gggcagaggc aggaaaacca gtattagaca attgcaataa   26340
tacaaactaa aaactattaa agcctaaact aaggcatgga aaacaaattc cagagaaatt   26400
aaataggtaa aaaccaacaa gacctggtat ttgatataga aggcaaggaa gaaaggagtt   26460
aagatgattc caagattcca acttgggtga ataaatgagt ggtaccattc actaaaagag   26520
aaactttaga aagataaaca gattggatgg gaagataaca aactgagtta ttcaggcaca   26580
taggtttcat ttgtagttgg atatacagac tttgagctca aaagtcaaag tttcagagtt   26640
gggatataca gacaattatc atcaaatacc ctttactacc ccccttggaa acatttttcat   26700
```

```
cttaacagtg aactcatgcc tggacattaa cattttgaaa ttatgcatta tcatagatta    26760
attttctctt tatactatgg gtaaggcatt acactaattt tcttaagttg tacataatag    26820
gttatattgt ccaggaattt tggattagta taaacagatg ctacaaaaaa gatgtaataa    26880
aaaggaagcc ctaggctggg tgggtgcagt ggctcacact tgtaatccca gcactttggg    26940
aggccaaggt gggaggatca cctgaggtca ggagtttgag accagcctgg tcaacatggt    27000
gaaacccttt ctctactaaa aatacaaaaa ttaaccggac gtggtggcag gcacctgtaa    27060
tcccacctac tcgggaggct gaggaaggag aatcacttaa acccgggaag cagaggttgc    27120
agtgatccga gatcgcacca ctgcactcca gcctgggtga cagagtgaga ctccatctca    27180
aaaaaaaaaa agtgacaaag ttgagaacat ggaataggag ttctgaagtt aattctactg    27240
atatctaaac caaactcaga ctgcaaataa gtaatttgta agtttccatc tcaataatac    27300
aattttctta gtaatgtgcc aaagtttatt taaacaaatg aaggaatgaa tacatcaggg    27360
ttacatactt cagaaaactc aaactactac tacaaatact acaattgtat atttagctat    27420
cacacaattt cttaaagagc tttaaaacaa caggtataca tatgtaacca acctgcacat    27480
tgtacacatg taccctaaaa cttaaagtat aataattaaa aaaaaaggaa ataaaaagga    27540
tacaatctaa agctcaaaaa aaaaagagc tttaaaacaa taaaatgcca aatcatcagc    27600
ctaataacta ctttattttt gggataaaat ggagatactt ttctgggctt taaatcctaa    27660
ctttggaaga ataagtattc aattcaacac atttattaaa taccatatta ataaaacact    27720
atagtgtgtg atgcacaatg caaacctgaa taggacacag gtaacaaaaa tataaacaag    27780
tgcaacagcc agacgcagtg gctcatgcct gtaaccccta aactttggga ggccgaggtg    27840
agaatatctc ttgagctcag gtcaagacta gcctgggcaa catagcaaca ccgtctctac    27900
caaacataca gaaaaattag ccaggcgtgg tggagcacat ctgtagtccc agcaacttgg    27960
gaggctgagg gggaggatca tttgagccct ggaggtggag gatgcagtga gccaagatta    28020
ccactgcact tcaagcaggg tgacagagtg agagcccatc tcaaaaacaa acaaaaaaac    28080
ccacaagtaa aacaaagcaa ttttacaata aaatctgaat atggaataga ggaagtacaa    28140
gggagtggtc aattcattct aggaactaaa caagctcctg agaggtgttt ttttgttttg    28200
ttttgttttt gtctttttta agagatgagg tcttgctctg tcacctggac tggatggcat    28260
gatcacagtt cactacagtc ctgacctccc agcctcaaaa aatcctcctg cctcagcctc    28320
ctgagtagct aggactacag gcatgcacca ctataccaag ctgattttg tagttttgc     28380 agagttagga ttttgccatg ctgcccaggc tggtcttgaa ctcctcggct caagtgatcc    28440
tcctgcctta gcctcctaaa gtgctggaat tataggcatg agccatcaca cctggcctaa    28500
gagcatttct taactgtagt tcgaggatgg gctttaggag cagtgtagtg tattagagac    28560
agctctaagc agcactcaaa agcaaactgt gagaccgggt gcagtggctc atacctgtaa    28620
tcccaggact ttgaaggcc gaggcaggca gatcacaagg tcaggagttc gagaccagcc    28680
tggccaacat gctgaaaccc cctctctact aaaaatacaa aaattagccg ggcgtggtgg    28740
catacgcctg tagtcccatc tactcgggag gctgaggcag aagaattgct tgaacctggg    28800
aggcggaggt tgcagtgagt cgaaatcatg ccactacact ccagcctgag tgacagagca    28860
agattccttc tcaaaaaaaa aaaaaaaaaa aaagcaaact gtgtacatct cttcccaact    28920
ccatgttttt agccttcaaa tgagagtatt atactatgga agtcagcaag cacataaatc    28980
agggcttttc tcatggaaag taggttgtaa aacacttatt gacttaccca tgtatatata    29040
```

```
catgtgcatc tttctggaac aagaacccaa tgcttttatc agcttattaa agagagatgt   29100
gacccaaaaa taaccagtta agaaacggaa gtaggaacat aaaattccac ttccacaaat   29160
tggtaaacaa aattttgtct ataaccaaag aaaaagactc atccttcatc cttacacatg   29220
gtcctaccta ggtaacaata ttatttccca aagcctttca atacattttc aaggtagatc   29280
actcctaaac aggagctttt gaaattacag acctttcaaa ataaatccta actctgatat   29340
cccaagtcta aattgatcta acaggatatt taacttaca ttagaacctc agtatgtggt   29400
tttagttcat atgtacttct aataaattta tcatactttt attacaatat ttaattaaag   29460
caacttttaa agagaatcac aattataaaa catatgcaca taaacaaaaa tgtctttaaa   29520
acgtttttat ggtatttatc catgatgctc aaaattaact taccctgctg attgactact   29580
accaagttcc tgtagatcat ggtatatatt ttccttgtag acagaaaaaa aaaaaataac   29640
aagagatgta cattttagaa taaaaatttg tattaagctg gatctaacca gacttctaca   29700
tacatactta gtatgaacta ctgcacacat tcaaaaccaa atttatcatt ggcaagcttg   29760
taggcactta aaagcacaat aattagtagc acaatgatta tgtacagcta cttttaataa   29820
ttactaaagt ctctctagct gaaagatttc acactaccaa ttcctgaaat gtgctttgtt   29880
tggactttac cagaagaccc ccaaaaaatg agtatgcaag caggaagagg ttgaacatac   29940
ttattttcaa acaggaatgt ttttagctct gtgcttagta gcaaactgcc aaaaaaaagc   30000
attgagttat gcaaaatcca ttaaatacaa actgccaaaa aaactattga gttacgcaaa   30060
atccattaaa taggaatttg attataatct tgactttcat caagcttcaa cttccttttct  30120 tgatcttaaa acgtattaac agaggccggg cgcagtggct cacagacacc tgtaatccca   30180
gcacttcgga aggccgagtc cggcagatca cccgaggcct ggagctcaag accagcctga   30240
ccaacatgga gaaaccccat ctctactaaa aatataaaat tagctgggca tggtggcgca   30300
tgcctgtaat cccagctact caggagactg aggcgggata tcacttaaa cccgggaggc   30360 agaggttgcg gtgagccaag atcacgccat tgcactccag cctgggcaac aagagcaaaa   30420
ctccgactca gggaagaaaa aaaagaaact tattaacaga taaagcagta ctcattcatt   30480
caataaatac agactgaaaa cctaccacgt accagtcact ggtactatgt accagacacg   30540
ggggaaaaca aagaatgaaa cagaaatgta tatgccctca tgaagtttat atcctaacag   30600
gaggataatt catttacccc agtattcgtt gatgtcacaa tggattttc cttttgtttt    30660 taaactaagg atttaagaga gtgtttgtca caaatattg tttctcactc aatattaaga   30720
ggaaatatga atcccaacta tctttttca tccttgggaa taaggataca gcaacctaaa    30780
cccacaatat ttttaattca tatcctttc aagtcagtaa tttctcctat ttcttatctc    30840
tcaacattta gaattcaagt ccaaggaaat catacttcca aacattatcc gaagattcaa    30900
tattcagacc aggcacagtg gctcacgtct gtaatcccag cactgggga ggccaagaca   30960 ggcagatcac ttgaagtcag gagttcgaga ccagcctggc caacatggca aaaccccatc   31020
tctactaaaa atacaaaaaa ttagctgctc atagtagtgt gcacctgtaa tcccagctac   31080
tcaggaggct gaggcaagag aatcgcttga acccaggagg cagaggttgc agcctgggca   31140
acagagcaag acttcatctc aaaaaaaaaa gaaaaaaaat agaagattca atattcaata   31200
ggtaaagaaa tcaccaatat accaatatag ttattttaa aatttataaa attaaccat    31260 ataccaag gccacgtata aaatgacaac atatatggat attaaacaga agtgactcat     31320
caataaaaaa taataattat acatatattt gtaaatatata taattatatt atatgtatat   31380
tataatatat aatatacaaa ttataataca aattaagaag ctagatgaaa tttaaatata   31440
```

```
gtactatatt cataactagg ttaaaacaca cagttgcaca taatacacaa atgactggta    31500 aaaataccttt ttgttaacaa actacagtcc ttttttttcc tttacttttc ttagttttct    31560
gtcatctcct aatgttcaat aataatatat actatgttta caataataag gttgttttaa    31620
agttataaaa tcccttgctc agctgaggaa gttatgtttt ttaataaaat aaaatcccat    31680
ttaattatca tcttttcagc tatactattg agcattaaat actagcagaa gctagttaat    31740
tgtctcaggt gaacgtattc attccattta ttaatgtaat gaatgctaag gctcaacacg    31800
gattgcctgt gctaaaccaa atgtgacaaa gaattccaaa tgtaggccgg gtgtggttgc    31860
tcacatctgt aatcccagca ctttgggagg ccatggcagg tggattaccg aaggttagga    31920
gctcaagacc agcctggtca acatcgtgaa accctgtctc tactaaaaat acaaaaatta    31980
ggcatggcag caggcacctg taatcccagc tactcgggaa gccgaggcag gagaatcact    32040
tgaacccagg agacggaggt tgcagtgagc caagatcatg ccactgcact ccagcctggg    32100
ccatagagca agactccctc tcaaaacaaa caaacaaaaa aaagaataat tttagaaaaa    32160
tatatattaa aaaaattttt ttttcagatg cagttttgct cgttgcccag gctggagtgc    32220
agtggcgcaa tctcggctca cctcaaccac aacctccacc tgcctggttc aagtgattct    32280
actgcctcag cctcccgagt agctggaatt acaggcatgc accaccacac ccagctaatt    32340
ttgtattttt agtagagaca gggtttctcc atgttggtca ggctggtctc caactcccaa    32400
cctcaggtga tccacccgcc ttggcctctc aaagtgctgg gattacaggt gtgagccacc    32460
gcaccaggcc tatttctaga aatattacct gggttaaatt ctgctggtta agtgccataa    32520
tgataggtga caatgaaaat gatctccaaa ataactaagg ctcaaatgta agcctttacc    32580
acgtggtggt atactgtttc tggaataaaa agttataata gctacagcta atacttgaat    32640
gctttgtatg tgcccaaaac tatgcttttt tatacaacgt ctctcttcaa gagctttaac    32700
ctccacatga agtatttaat tatccctatt ttataaatgg ggaagcaggt ttaaaaaggt    32760
taatttatct agtcacaaaa ctagtaaatg attgggctag gtttcaaaca ctggtttata    32820
agatgccaga gctcaggttc tcaaataata tgccgcagag ctaaaaaatt aagtttcagc    32880
atgtctttaa tatgtttcaa cagttttct ctgacaaaag tgaatgaggg tagaggtgaa    32940
ctgaaatgtt agcccagatg gctttttaca atggactaaa ctgaagaatt acctgtgctc    33000
tttcacagag aagcttggca cgccaaacaa atctcctaga agatcatttg aacaatatac    33060
aatatgttgt tgcttctcat catataatcg tttagtcata atatactggc caagataaaa    33120
aagaacctga atacaaaata tgatttctga gcattaaaga aaactaaatg ttagttgtaa    33180
atacatttaa taatatccta tttatctgaa taggggtaaa caaccaggaa ccatatccac    33240
aactatgtag aacaaccatt ttgtacttag aagctacttt tggctgggcg cagtggctca    33300
cacctgtaat cccagtactt cgggaggccg aagcggatgg atcacgaggt caggagataa    33360
agaccatcct ggtcccatct ctactaaaaa tacaaaagtt agccaggcat ggtggcagac    33420
acctgtaatc ccagctatta gggaggctga ggcaggagaa ttgcttgaac ccaggaggtg    33480
gaggctgcag tgagccgaga ttgcgccact gcactccggc ttaagcaaca gagtgagact    33540
tcatctcaaa aaaaaaaaaa aaaaaaaaa aaaagctac ttttaagcct tttccattta    33600
atttgacaga agcagaaata actgcttctc tatttactta agcaaacctt aaaatgtgag    33660 gttttttcc ttgtagactt taactctgcc cagatactta gatactaaca tattaggaag    33720
ggaaaaggca gcaaaataaa aaactgatag ccaaaaaagt tgcagaaaca aaaatcaact    33780
```

```
aaaatatggc agtggtctgg agccacttag taaatagtca taaatactat aaacctcaat    33840
agcctctgag gtcaccagag gaggaagaca gaaaaacaat caatcaatga cagctacaaa    33900
acagtttgag agaattctga gaatgaaata aaccctctaa ggtatcaatt tactccatat    33960
tatgataaat aatcaaaata atgactttga accattaata aaagttaaat tatattccct    34020
gtgctgcatt aagacaagaa gttggcaata cattttaag atatccagat ataaacctat     34080
taacaactac ctaaatacat atggcatttt acagtttaca atgtactttt ataagtatta    34140
tctcattctg atatttcata agattattat cactgtatta gaaatgaaga aattgcgttg    34200
ggcacagtgg ctcacacctg taaatctagc actttaggag gccgaggtaa gcagatccct    34260
tgagcccagg agttccagac cagcctgggc aacatagtga aactccatct ctacaaaaaa    34320
atacaaaaat tagccaggca tagtggtaca agcctgtagt cctagctact gcagacactg    34380
aggtgggagg atcacctgag cccacgaggt ccaggctgca gcgagcagtg atcatgccac    34440
tgcactccag cctgggcaag agagtgagaa actgtcacat aaaaaaaaaa aaaaaaaaaa    34500
aaaagaagaa gaaactggcc ccagctcttc tgactcttaa tccaacgctc tttttactac    34560
ccatactagc tttcactacc ttcctgtgtg ccccagaaca aagatcctat aactgagaac    34620
tatatcagac aatacataca ctactgttac atagtttagc ataagcattc taagtcttta    34680
tgatggcctt ggccaatttt ctcatttcta tctactgcta aatccatact tttttgtttc    34740
cttaactgat tatccaatga taataaggtc aatcccaaat tagccttaaa aataccattt    34800
aacctggccc tttcctacaa acactgtctt tggatttaac tggctaagca ggcatcggcc    34860
ttaaaggaat attcttatgt gactgtggat tggacagatt gctgtccagc agtgggaaag    34920
gaaaaaggaa gagaacttag atttattcta ccaaacatcc tttaaggaag tttctaaaag    34980
tatagctgga gaggaaaaag aaaaatggaa gctcttcctg ccccactata ccgttgtaag    35040
aaagaaactt aaatgtttta agtaatctga gtcccataaa ctaagtggga gagacagaga    35100
acaggcatat ttcaatcaca ctgaaaattct gcctaaggtt gctcaatctg tcactgaaaa    35160
tcatgcttct gtgcacaaat ttaaaggtgg ggaatgcatt aaaatgctgg aaccattaga    35220
tagaatatat ggtcatgaat cagctcacct ctatcccaga aagatcagta tactgtactc    35280
atgtatctct agtgcagaag ttcttaacct gggatccagg gatgcccaag aagtccttgg    35340
atagaattca gggggtccat taatttggat gggaaaaaaa aaattctatt cttatttca     35400
caaacttcta actagaattt agcttttcct tcgattataa atgtaggcaa caaatcacaa    35460
cagtattaat acctgtgatt tcatcaccaa caaaaatcag aggtgttttc ctatcatact    35520
gtacttatgg caaacatttc aaaatatgac ttatattcct cactatatca agataatatt    35580
tattggccag gcatggtggc tcatgcctat aatcccagca ttttgggagg ccaaggcaag    35640
tggatcacct gagactagga gttcaagacc agcctggcca acatggagaa accccatctc    35700
tactaaaaag acaaaaaatt agccaggcgt ggtggcaggt gcctataatc ccagctactt    35760
ggaagggtaa ggcagaagaa gggcttgaat ctaggaggcg gaggttgcag tgagctgaga    35820
tcgtgccact gcactccagc ttgggtgaca gagcgagact tcgtctcaaa aacaaaaaa     35880
acattatatt tattatatct tcttctaaat cttagtattt attatgttaa taacaaaagc    35940
acacatatca caaactagtt tactatttg gtaaccgtat tttagtatgt ttcctttgta    36000
attctataca ttttatttca tacatttaaa aacatgattc tgggaaggag tctaccaaag    36060
ggttgacagc ataaaatggt caagcaccct tacggggctt ccatttatct gagttcctag    36120
ctgagaaatg aaactcgagt ataattagaa ttttcagctt taaaatatag tccaaacgac    36180
```

```
cacaaaatta aatgttgctg cttaatgaaa aatccttcta tatggccaat ttctccacat   36240
ggtcttgaaa actttaagta tggctacatg taactagtga gatactactt atctcttgat   36300
tcagcttacc tctttcatag tataagtgtc tttttgtgca ccaacagact ttaataactt   36360
caaaagcaat ggctttggtc taacctataa agagaaaaga actgctatta tacttccaaa   36420
attatcccag aactataggc cctgcagcaa acatatccat caagttcaat aaagggggatt  36480 tggaaaaaat gctggggagg atctaatcat tatgcaagta tcatggaatc atcaagtatc   36540
agttgtgatc acagacagta tccaatccaa aagagcaaag attactttt ccttcagcta    36600 tttatattac ctgcttactg ccttacaaac aaccataaat tactgagatc caatgagctt   36660
accgtactga tccaacgagc ttattgcaag ctaacttaga gaatcaaaga gaaatgaata   36720
aatctttaga gtgggtcctg ttatcaatct tctctttcta aagattaggt tcctgaaggc   36780
tagagaacct aactaactaa cccaagctga caagggtaat taagaacaga tcagagataa   36840
caacccaggt ccctcaacta caactcagca ttttcttcct actatatcat gctgcctctt   36900
agttagtcta catttcaaat atctacttga caaacattta ttgagcttct actatgcact   36960
ggacagtggt aggtactgca aaagaaatta caaataagac atatgacctg tatgcaagga   37020
gcctgccaac tagattaggg gtcaattttt ttctgtaaag agccagactg taagtatttt   37080 aagctttca tacaaatggt tctatccaag taaaaagcat ggctactatg taaaccaacg    37140
ggcatggttg cattccagta aaattttcct tacagaaaga aaggcagctg gctgggagag   37200
gtggctcttg cctataaccc cagcactttg ggagacagtg ctagaggttt gcttgaggct   37260
aggtgttcaa gaccagcctg gccacactg agagactcca cctctacaaa aaaaatttaa    37320
aaactaaaac aaaaacaggt aacaggccaa agttggctga caggctaaca tttgcctgcc   37380
ccttatctag aggttttaca aatggtcttg agaaaaataa ttgtcatggg ggagggggaat  37440 gtaatatact atgcactttc tccccttcctt ttggtttatc aaaatctgca aaactcaagt  37500
atctttacag cttgccacta ccacacaaac tggtacctct gcacctctct ttaatatgcc   37560
ccggtcctct gtctaacttt aaaatctgac agcaccccca ttgggatgc cttaaaaaca    37620 gatttttaaa aattgcctat ttccagctaa tcaataaaac aaatattatt taacaattga   37680
aaaatttaaa atacatatag aattgaatta ttaattttc tgatcactttt ttttttttttt  37740 aactgtgctt acatatgcac tttacttca ggctaaagaa tggactctct caaaaaagat    37800
ttaaaaataa cctttttct cctgaatttt tattatatgc tatattagct tcaaattaga    37860
taaaataatt caaagtaaaa atctgtaatg gaagccaggt gcagtggctc aggtctgtaa   37920
tcccagcact ttgggaggcc gaggcaggca gatcacctga ggtcaggagt gtgagaccag   37980
cctggccaac acagtgaaac tccgtctcta ttaaatatac aaaaattacc caggtgtggg   38040
ccaggcgcag tggctcatgc ctttaatccc agcactttgg gaggccaaga caggcagatc   38100
aggaggtcag aagttcaaga ccagcctgga caacatggtg aaaccctatc tctactaaaa   38160
gtacaaaaat tatccgggtg tggaggtggg tgcctgtaat cccagctact cgggaggctg   38220
cggcagaatt gcttgaaccc aggaagcaga ggttgcagtg agccgagatc atgccactgc   38280
actccagcct gggcaacaga ccaagactca gtctcaaaaa aaaaaaaaaa aaaaaatctg   38340
taatggaaag ccatcagtat attagtgact aaaagacat gtattaatga gaaacagct    38400 ataaaagata atagcatttg taatcttaca ttgaagaaca agaaggtaaa ttacaggtga   38460
agatctaaat atttaaaaaa tttaaatcta gaagaaaata taggaatata tttgcaagat   38520
```

```
cttgggacag gagagttctt ccaaagcatg atatgaaatt caaaagccaa caaattttac    38580
ttcacagaat tgttctcaat ggggaaaaga caacataaaa ttaaatgcta cattagtaaa    38640
caacaaaagt taaatatact tgaaacacat agagctactc caattactaa gaaaaatttt    38700
aaaaaactaa aaggaaaatg gacagataag actaggcaag tcccagaaga aataaatgac    38760
ttaacaaaat ggaggcctgg tgcagtgatt cacgcctgta atcccagcac tttgggaggc    38820
cgaggcaggc agatcacctg aagttgggag ttcaagacca gcctgaccaa catgaaaaaa    38880
ccccatctct actaaaaata caaaattagc tgagcgtggt ggcgcatgcc tgtaatccca    38940
gctactccag aggctgaggc aagagaatcg cttgaacccg tgaggcagag gttgcaatga    39000
gacaagatct cgccattgca ctccagcctg gcaacagga gtgaaactct gtctcaaaaa    39060
aaacaaaaac aaaaacaaaa aggaaaggtg cccagcctca ccaagaaact agagaaaaat    39120
gaatttaaac aatggtacag tacctttat caaaaaaata gtaataataa taaagaggc    39180 caggcgcagt gactcacgcc tgtaatccca gcactttggg aggccgaggc gggcggatca    39240
ccaggtcagg ggatcaagat catcctggct aacatggtga aaccccgtct ctactaaaaa    39300
tacaaaaaat tagccgggcg tggtggtggg cgcctgtagt cccagctact cgggaggctg    39360
aggcagggga atggcgtgaa cccggggaac ggagattgca gtgagccgag attgtgccac    39420
tgcactccag cctgggagac agagcaagac tccgcctcaa aaaaataat aataataata    39480 attaaagatt ggtgatattc agtattggca ggagtgaaac tgttagagcc ttttggtgag    39540
caagttacca gtagcaatca aatagtaaaa ttgagaactc aggagttcta attctctaaa    39600
atctttttct tttcttttt ttttttttag acggagtttc gctcttatcg cccaggctgg    39660
agtgaaatgg cgcaatcttg gctcaccgca acctctgcct cctgggttca gcgattctc    39720 ctgccccagc ctcctcagca ggggattata gcgcgcgcc accatgcccg actaatttt    39780 gtatttttag tagagacagg ttttcaccat gttggccagg ctagtcttga actcctcatc    39840
tcaggtgatc ggtccgcctt ggcctcccaa agtgatggga ttacagggt gagccaccga    39900 ggccagccta taattctata aaatctttct tacagaaata gtcacacggg atgcatgtac    39960
aaagcggcac tatctgtaat actcaaaaac aggaggcaat ttttaaaaac ctatcagtaa    40020
aggcataaat aattttaaa atggtatact catgctgtgg aatactatgc agccattaaa    40080
aagaattctg tagactttat ttattgcaa ggatgcaagt cacagaacaa ctacagtttc    40140
atcttgttag tacaacaaac aggacaataa catagattta aattcaaatg taaatatatg    40200
tgggtacgca cacaaaaaat ctaaaaggaa acatggagca aaaagcctgg aattttcagg    40260
ttttacttta aaatttctct aatgacaaaa atctttaaaa caagcacgaa taacttttt    40320 gacttttaga aaccattttt aaaaattaaa tactgggagg tcaaaaagga aaaaaaatc    40380 agtcacgtaa caaacgtaac ttcaaccacg cttaacaatg taatggaact aattttaaa    40440 gcaaatgtgg caaatggcta aaaaaatact gaccagttct taacagtttt taactccacg    40500
cagttacgcc agaggtagca cactttaagc tatgcacata caatttattt tacagagcca    40560
tgctacaatt gaggtatacg aaatttagtt tatcacttca taaaataaat tattcttaaa    40620
agttacacga gacaaaaata ctaaccaggg tctcttgttc cgaagctgga atctgtgagg    40680
tggttacagc accatcagta ggtacagaca tgttggtatt gcacatttgc ctacaaggaa    40740
aaaaaagaca cgatgaaaac tggaaatcat gaaacatctg tggaaaatac atcatatata    40800
aagaacataa acaacagtta aaactaaagc tacaagcaag tcggtgctta cctggatcag    40860
cagagaaaaa gtggcgtgcg tccgtgccca caggtctacc ctccaatcgc cactgaacac    40920
```

```
agctgggaaa atgcatggtt taaatagccc cagctggaga caagtcagga cttaactcct   40980
tttactgcag tttcggaacg tgtctgaact tgaccagctc aagaggaaaa gctgagtcaa   41040
cctgcccact gaaccggccc aatcccgccc agactacgcg cagcgttcac actagtgacc   41100
cgacaggcac ctgcgatcat ccggacctcc cgcgccgaag cggccccgca gcccccggcc   41160
cccgtgacct ttaccctgaa ctcccgcgga gacctccgaa ccaccccac ccccaccgcc    41220
gcgagagccg tccgaaatcc cgccctcctc cctggcggcg actgcctagc cccagtccaa   41280
caaaacctcc gcaaagccac gtgcccatg cccgcgccc cgcgcccga gccccagcc      41340
acgaaccgca caaggctgc gaacgggcag aggctgggaa ccagcgatag aggggacacc    41400
gtcagagccc agacccaaaa gtgaccgctc gctgccgggc cagtacctgc tcctcaccat   41460
ccggggtttt cgcgcttgga gtcggggtc cctcaagact ccccagtttc cttcacgggg    41520
cgcgcggaag cacgacgccc tgggcctcgg ggatcattcc actctccggg ccagggcact   41580
gggcgctcgt acgcactaat ccggggaggg acggtgctcc tggctgcgaa agcagcagga   41640
tctcggtcag aggggtcgcg gccgcccctc gggctcggct tcttgctcca tctttccgac   41700
acacagggcc acacaggccc cagaagcagc caagctcgcc gcggtgcctc ggtgcgcgcc   41760
ccctaccgcc cgaggggagc gcgcgggtcg tcgcggcgca tccgggcatt tgtgcgcgcg   41820
cacacaaccg gccccgcttc cgccaattgg gtccggggct cggccgcacc acctccggga   41880
tgatggagtg gggggtgtcg ccccgcgggc gcggcgggct gtgaggcggg gtggggtgt    41940
tggccgcgag ctgagagggt ggggctcggc ctggcgcgga gccagcaagg tttggcgctg   42000
tgacactcct ttagccgttg cgctatgttt gtatttcttg tgtttacact tcccgcccgc   42060
ggtggaaact gcgacaaatg cggatctccg tgtcgctgtt accaaaaaga aaccaaaatt   42120
aacagctgtt taatatatta agcccactcc accagccgct ggagttgtac ccaaatgagt   42180
tattttaagg cctgttttta aaaaagatta aaaatagcac ttaaggcagg cttatacacc   42240
ggtgcataca gctgttctgg ttggagaacg aagatgctgg ttaccgttgg cggggagggg   42300
agcggttact ctgcgctttt agaatgtttg ggtttgctg ggcgcggtgg ctcacgcttg    42360
taatcccatc actttgggta ggccgaggcg ggtggatcac ttgaggtcag gagttcaaga   42420
ccaacctggc caacatggga aacgccgtct ctactaaaaa ctacaaaaat tagtcgggcg   42480
tggtggcggt cacctgtaat cccagctact ctactccgga ggctgaggca ggacaatcct   42540
gtgaacccgg gaggcagagg ctgcagtgag ccaagatcat gccattgcac tccagcctgg   42600
gcgacagggc aagactctca aaaaacaaa acaaagtttt gggtttgtta atctacacat    42660
tcattatcat taaatatat acttatatat tatgcactca ttctgactca cctactttcc    42720
cacagagatg tggcaaaaac gttttgatg cggtctcata aattgaggac ataaagaatt    42780
gagttagcta aacccaaaaa cacagccatt gcaagaagg aacacgtttc ttctctggcc    42840
agtaagtgat tagctccttg tgaacaagga ccttttttta taaagttata tccttccctt   42900
ctgcagcttt ttttttttta taaagttata tccttccctt ctcccgcttc ccagcctacc   42960
agaaaggaaa cttccttaaa catagtggtc actcagttga tttaagttga ttgccaatat   43020
tattaactta agagatttaa tatgtggctt ttaaaaagat aatctcatct tcatcagatc   43080
atatacagtg gggtttctaa tagactcagt gcttgaccct ggatgaaaga aaatctcaag   43140
cagtgagaaa atgtaagcat gaaaagataa gtgataggct gcgcacggtg gctcacgctt   43200
gtaatcccag cactttggga ggctgaggtg ggtggatcac gaggttagga gttcgagacc   43260
```

```
agcctggcca agatggtgaa accttgtctc tactaaaaat acaaaaatta gccgggcccc    43320
gtggcgggcg cctgtaatcc tagccacttg ggaggctgag gcagaagaat cgcttgatct    43380
cgggaggcag aggttgcagt gagcggagat cgcgccactg cagtccagcc tgggtgacag    43440
agcaagactc catctcagaa gaaaaaaaaa aaaaagaga taagtgatag aggttgatat     43500
ttgttaaata tcaagtgaac gaatgggttt gtgctataaa agttcagaga cagaattaat    43560
tgcttagtaa atgctggagg cagttcacaa aggcctcaga gatcacacat attttgtgtc    43620
ttgaaagatg gtgagactta aataaaagca gagaatattc caggcacaag aaaattatca    43680
aaaaatacag aaaggaaaat ataagaggac tgtttgagat acaataaata aatccgtttg    43740
acttgcatga aagtcaagaa gaagttttaa gaacttggag tctccttaaa tgccaagcaa    43800
ggaaatttgg gctttcgaca gagtagacat tagaagcata aaaacaagtg atttgcttca    43860
aactgtattt taacaggacc accaagagta gattcaaact cagaatagtc gggccggctg    43920
ccttctggac cgactttccc ccttctcatt ggccttgtgc tttgaaaaaa ttatcttgac    43980
aaaattatta gagcagaaaa aaaaaggcag aactgataag attagtcctt ttctaatgga    44040
accagaaaag aagggtcaga aatgaaggca gaagggagaa gcggggtgg gggagagaga    44100 gagaagtaaa aaggattcac tcaagaacct ggtattcaaa actacgtgta ccagcactac    44160
cacagcagta tgactcagtg tccacctaaa gcatgatgat actgcttacc aaaaaagtc     44220 tggagggaat gaaaagttgg gttagtttta agttatgggt cacagaacag aattcggtgg    44280
taaaaagctt aggctgggaa cagagcttga aacagcaaag gaatgagagg aacgaccaaa    44340
aagccaagga ccatatagtg atgtctgaaa aatcagaatc aggtaataat attgaatact    44400
gcaaaagtca gagaaaatgt ggaaataaga aagcaagcga tctggaaagt ggcgagtaag    44460
atggaatatg aggaggttgc tgagagctgg gaggagacgg cagacagcgg ggaaatagac    44520
gtctggaaaa aaaactgaag atcacacaga aagcaggaaa ttcaaatctc ccaaagtgcc    44580
cattgtgatt caggatgata atttccccc gggacccct ccacaggtcc gcatcctcaa      44640
gaggcccacc agcaacggtg tggtcagcag ccccaagtcc gctagcaggc ccgcccttcc    44700
agtcaagtcc ctggcacagt gggaagccga gtacaccgag gccaggaagc ggatcctggg    44760
cagcgccaac ccgaggagaa gcaggagaaa cccatcctcg ataggtcttc ctctgatctt    44820
cttcccttca ggccaaccag gatctcctaa cccgaagaca gcagacagcc caataatgtg    44880
atcagacagc ctctgggtcc tgatgggtca cacggcttca aacagcgcag ataaatgcag    44940
gcaagaagag atggcgcgac tgccgcgtca acgcgtcctg ggtcgtccgc caagggttgc    45000
actaccgtgg cagacagctg gacttgagca gcgggaactt gacttacttg cctggtgatc    45060
cccgttgctc cgcccactgt gaccttgaat cccatgcact gtgacctccc ccttctcct    45120 ccttcccact gtgattggca ctttgacaag gactgtccca agtcaatgga aagggaaaaa    45180
gggtgagggt taggagaagg ttgggggaa cccaccaatt actcagagta gagagtcaga     45240
cagggccagc aatagcggtt tatcatgctc attaatttgg gatttcaaaa cacaaatgaa    45300
ctcacaccta cccaccccca agtgcatgtc atcacttaaa aagtgagttc catttgaaaa    45360
aaaagaaagc aaaactacctg ctcactctaa agcagttgc tgttgtttgt gactttgcca    45420
tttaaaaaaa tacagaccag ctgctgctgt ttgcttgcat tccacagtta tcttgtgtca    45480
ctttgccctt tgttgtgctt acttgaagtt tctctagagg caaactgctt atttctagta    45540
gcgttgttct tgatgcccaa gaggtgttcc aagaggttga gatactttga gtgtctttat    45600
attctctggg acctaaactc tgcaaacaag gctcacacct gtaatcccag cactgtggga    45660
```

```
ggccaaggct ggaggatcta ttgaggccaa gagtttgaga ccagcctgag caacatggcg    45720
aaaccctgtc tctataaatt gcaaaaaaaa attagccagg cgtggtggca ctcacctata    45780
gtcctagcta cttgggagcc agagctggga ggatggcttg agcccggata ggttgtggtg    45840
tgatcctgcc actgcactcc agcctatgtg acagagtgag accatgtctc aaggggaaaa    45900
aaaaaagtct acaacagact tatcttgacc caagggccac ttcgtacttg tatttattag    45960
tcataactaa tcttttgtct ttcttttttt tttttttttg agacggagtc tcactctgtc    46020
acccaggttg gagtgcagtg gcacgatctc agctcattgc agcctccacc tcctgggttc    46080
aagtgattct cctgcctcag cctcccgagt agctgggatt acaagcttgt gccaccatac    46140
ccggctaatt tttgtatttt tagtagagac gggatttcac tatgttggcc aggctggtct    46200
cgaactcctg gcctcaggtg atccacccgt ctcaccctcc caaaatgctg ggattacagg    46260
cgtgagccac tgtgcctggc cacaactaat ctttaaagca tggtgaaaac taaacaagat    46320
ttagctcaga accgtgttt agaatgctga gtttcacaat atttatgaga ccatctaaaa    46380
ttacagaagt agttcaaatt ccttatgtct ttccaaacat ctggaactga atagtgttat    46440
ttaaaaggca aaatccgggc cggacgcagt ggctcacgcc tgtaatccca gtactttggg    46500
aggccaagac aggcagatca ctgaaggtca ggagtttgag accagcatgt aaaacccgt     46560 ccctgctaaa aatacaaaaa ttaggcgggc atggtggtgc aagcctgtaa tctcagctgc    46620
tcgggaggct gaggcagcag aatctcttga acctgggagg cagatgttgc agtgagccga    46680
gatcgcgcca ctgcactcga gcctgggcgg cagagcaaga ctctgtcctg aaaataaaa     46740 aagtaaaaaa taggccgggc atggtggctc atgcctgtaa tcccaccact ttggcagggt    46800
gaggcgagtg gatcacctga ggccaggagt tcgagaccag cctggccagc atggtgaaac    46860
cctgtctcta ctaaaaatac aaaaaattag ccgggtatgg tggtgcacgc ctgtaatccc    46920
agctactcca gaggctgagg caggagaatt gcttaaacct gggaggcaga gatcatgcca    46980
ctgcgctcca gcctgggaga cagagtgaga gtgagactcc atctcaaaaa ataaataaat    47040
aaataaagta aaaataaaa agcaaaatcc cagcaagtag tgaatacaaa gacttttgt     47100 ttttactttg aaaattaatc aacttttgt ttgactgaaa catacagaaa cattcacaga    47160
acaattaata ttcaacaaaa gaaaccaccg cctcaagttc ttctgctctg aagaacaaaa    47220
aaagaaaaaa agaaaccact acccagaatt cacatttgtc attcctgcat caaacatatt    47280 tttttttatta tttatttatt tatttttgaa acagagtctt gctctgtcgc ccacactgag    47340
tgcagtgagc caagattgta ccactatgcc tggctaatct ttagtatttt tagtagagat    47400
ggggttttac catgttggcc aggctggtct caaactcccg acctcaagca tccacctgc    47460 cttggcctcc caaaatgcta ggattacagg tgtgagccac tgagcctggc ctaaataaat    47520 tttttaatg aaacattgct taaaaatta aatttcact gttattcttt atcccattcc     47580
cctcccttct cttgataatg atcaatttga tgcctgtcca ctaagtctgt gttttataca    47640
ttcactgtaa atttatgaat ccataaacaa cacggacagt aggctgcata cctataagag    47700
gacttgctgg gcaacagaat agtaaaccct agagtaagtt tcaatatgta acaggaaag    47760 ctctctttat cttttcagt attgttttgg ctcttcctgg atgttaactt ttagaaccag    47820
tttgtctaat tcacaaaaag aatcctcttg ggattttgct tttcattgca ttggattgtt    47880
agactaattt gacttatttt cagtatgaat tcttcccaga taagaacatg atatatcact    47940
ccatttttag gtctctctta acatccttta ataatgcttt attgtttcct ccttaaagct    48000
```

```
gttgtatgtt tggctggctt ttttctgaag tgctttataa gttttattgc tgtttttaaa    48060
ttacacctt  taaaattttc  ttttcttttt  ttttgagatg  gagtttcgct  ctgtcaccca    48120
ggctggagtg  cagtggtgcg  atcttggctc  actgtaagct  ccgcctcccg  ggttcatgcc    48180
attctcctgc  ctcagcctcc  ggagtagctg  ggactacagg  cgcctgccac  cacgcccggc    48240
tatttttttt  ttgtattttt  agtagagaca  aggtttcacc  gtgttagcca  ggatggtctc    48300
gatcttctga  cctcgtgatc  cgcccacctc  ggcctcccaa  agtgctggga  ttacaggcgt    48360
gagccaccat  gcccagccgt  aacatttat  tttctatttg  gttattgcta  acatatgaaa    48420
caattactca  ttttttgtgtt  ttgatcttat  agccagccag  caatactgct  tttttgttct    48480
ttctgttttt  gtttttttgtt  ttttgggttt  tttttgagac  ggagtctcac  tctgtcaccc    48540
agacgggagt  gcagtggcac  aatctcggct  cactgcagtg  tctgcctccc  tggttcaaag    48600
gattcttctg  ccttagcctc  ctgagtatct  ggcactacag  gtgcgtgcca  ccacacctgg    48660
ctaattttta  tattttttact  agagatgggg  tttcgccatc  ttggccaggc  tggtctcgaa    48720
ctcctgacct  cgtgatccac  ccaccttggc  ctcccaaagt  gctggattta  caggctgtat    48780
tttgtttttgt  tatacagtac  tattagtttt  tcagtagatg  ctcttggatt  ttctatgtta    48840
ataatatcat  atgcaaaaat  cactaacttg  tctcttcctt  aaacctcttt  ttcattttct    48900
tacaaccatt  ggaatggaat  agtagcaatg  atagtgggca  tcctcatctt  attcatgaca    48960
ttagtaaaaa  tgcttttaaa  atgtgatgtt  tgctgtaaat  tttaggtaga  tgctctttat    49020
tacataaaag  tttccttcta  ttcctggttt  tttgagctta  taaaaagta  tgaatcagtg    49080
ttcagttta  tacactgctt  ttttatgcac  ctagaaatga  ccctgtggct  tttctccttt    49140
aatctgtcta  tgtggtgaga  ttatattgat  agatttccaa  tattgacctt  ccttgtttta    49200
ctcagataaa  attctactta  gttacaatag  atctctttttt  ttggacattt  atgaactgaa    49260
tttttaagag  gaaaaatatt  acacaatgat  atgggagcat  aattgagttc  ctgctcttag    49320
aagataacaa  atatttcaga  gatttttagta  ggaatattgc  cctgttaaga  acgctcaatt    49380
ctctaaagct  aagttcaaat  aaggcccaat  tcttggcctg  agactctggt  tcccacaagg    49440
gcaatacagg  ctgaactggt  ttgataactt  ttaccattga  gagttttttt  tttctttttg    49500
agacggagtt  ttgctcttat  tgcccaggct  ggagtgcaat  ggcttgatct  cggctcagtg    49560
caacctccgc  ctcccagata  caagtgattc  tcctgtctca  gcctccgaag  tagctcagat    49620
tacaggcatg  tgccaccaca  cccagctaat  ttttttgtatt  tagtagagac  atgtttcatc    49680
atgttagtca  ggctggtcgt  gaactcctga  cctcaggtga  tccacccgcc  tcagcctccc    49740
aaagtgctgg  gattataggc  gtgcgccact  gcacccggcc  acgtttaaga  gttttaagga    49800
aggaccagga  ataatagagg  tcatcttttc  gtggaacgaa  gagtttataa  tctcccagct    49860
gacctaaatc  tgagatctgt  gatcgtatct  agtctgaaag  ttacagagcc  attcagctgg    49920
cagaagaaag  gtagtgaagt  tgaacagcat  ccccactctt  tggggtggaa  aggttgctgg    49980
agtttccccc  agattaagtg  gttcctggag  aagatggaag  gagtataagc  agttctgctg    50040
gtaactccta  aaatggccac  tacctgggta  atagaaccct  ggaagcaaaa  gacatagaat    50100
atctattggt  agaatgtgct  ggactaggga  gaaagaagtt  gagcttcatt  catataccccc    50160
tgctcaactt  cctaccagga  ccatgccacg  agtctttctg  gagaaatatc  atttggacac    50220
ctgccagatg  aagagaactg  gtggtcaatt  ggtaataatc  agagaaactg  gacaaccaa    50280
cagaaaggga  cagaaatgtt  tcccatgatc  tagttgaggt  tgttcataca  atgaaccaca    50340
gttatgtcct  gctaataaaa  gggcaactaa  ttttgaaggg  caattatgta  aagaaatgta    50400
```

-continued

```
attttcctct ccttcctcct tgccacccca actggtatcg ggatggcagg agtcatgtgt  50460
ggttttctat ggctgtgtaa caaattacca taaatgtagt agcttaaagc aacacaaatt  50520
attagctcac agtccatata tcagaaatcc aggtaggctc acctggttcc tctgctccag  50580
gtgtcataaa gcctaaatca aggtgtgggc cagcttgggc tcttaaggat ctagggaaga  50640
acctgctttc tagcttattc aaattgtcag ccaaattcag ttccttgtgg ttgtaggacg  50700
gtagtcccct ttttcttgct agcagtgagg accactctca gctcctgaag gcttcctgca  50760
ttccttgcta cacactcccc tccatcttca agccagcaac agggtgttga atcacccttg  50820
tgctttgaac ctgacttact ctcctgctat cagccagaaa aaaactctga cttcaaaggc  50880
tcatgtgatt tgatgaggcc aacccagatc atctcccttt tgccatgtaa tgtaacagaa  50940
tgatgggagt aatatctcct catattcaca ggttcctccc acgcttaaag gggaggggat  51000
catccatagg caaggtcact gggagtcatt cttggaatt                         51039
```

MODULATION OF HUMAN MOUSE DOUBLE MINUTE 2 HOMOLOG ACTIVITY

PRIORITY CLAIM

This application is a divisional application of application Ser. No. 13/116,140, filed Nov. 20, 2011, which is a divisional application of application Ser. No. 12/795,864, filed Jun. 8, 2010, now issued U.S. Pat. No. 7,964,357, issued Jun. 21, 2011 which is a continuation application of application Ser. No. 10/608,403, filed Jun. 27, 2003, now issued U.S. Pat. No. 7,754,424, issued Jun. 13, 2010 under 35 USC §120, the contents of each which are incorporated herein by reference.

FIELD OF THE INVENTION

The invention is directed to isolated genomic polynucleotide fragments from the human chromosome 12q13-q15 region that particularly encode human carboxypeptidase M and human mouse double minute 2 homolog, vectors and hosts containing these fragments and fragments hybridizing to noncoding regions as well as their reverse complements t. The invention is further directed to methods of using these fragments to obtain human carboxypeptidase M and human mouse double minute 2 homolog and to diagnose, treat, prevent and/or ameliorate a pathological disorder.

BACKGROUND OF THE INVENTION

Chromosome 12q13-q15 contains genes encoding, for example, interleukin 22, a protein tyrosine phosphatase, interferon-gamma, carboxypeptidase M and the human mouse double minute 2 homolog; the last two of which are discussed in more detail below. The chromosome 12q13-q15 region is known to be aberrant in tumors such as sarcomas (Oliner et al., Nature 358: 80-3, 1992).

Human Carboxypeptidase M

Human carboxypeptidase M is a cell membrane-bound basic carboxypeptidase believed to act by activating, inactivating and modulating excitatory peptides such as the anaphylatoxins and kinins (Tan et al., J. Biol. Chem. 264: 13165-70. 1989). Its expression is increased as monocytes differentiate into macrophages (Rehli et al., J. Biol. Chem. 270: 15644-9, 1995). It is also widely distributed as an ectoenzyme of specialized epithelia and endothelia. Its ability to convert anaphylatoxins to their less active C-terminal des-Arg forms protects against complement-linked tissue damage.

Human Mouse Double Minute 2 Homolog

Human mouse double minute 2 homolog plays a key role in modulating actions of p53 (Oliner et al., supra), in part by targeting p53 for destruction (Ries et al., Cell 103: 321-30, 2000). Over-expression of this oncogene increases tumorigenic potential. The human mouse double minute 2 homolog is over-expressed in both sarcomas and some leukemias. In addition to its ability to in effect neutralize p53, it reacts also with a retinoblastoma protein.

SUMMARY OF THE INVENTION

The invention is directed to isolated genomic polynucleotides, said polynucleotides obtainable from the human chromosome 12q13-q15 region having a nucleotide sequence at least 95% identical to a sequence selected from the group consisting of:

(a) a genomic polynucleotide encoding a polypeptide selected from the group consisting of human carboxypeptidase M depicted in SEQ ID NO:1 or human mouse double minute 2 homolog depicted in SEQ ID NO:2, or variants of SEQ ID NOS:1 or 2;

(b) a genomic polynucleotide selected from the group consisting of SEQ ID NO:3 which encodes human carboxypeptidase M depicted in SEQ ID NO:1 and SEQ ID NO:4 which encodes human mouse double minute 2 homolog depicted in SEQ ID NO:2, or variants of SEQ ID NOS: 3 or 4, (c) a polynucleotide which hybridizes to any one of the polynucleotides specified in (a)-(b) and (d) a polynucleotide that is a reverse complement to the polynucleotides specified in (a) to (c)

as well as nucleic acid constructs, expression vectors and host cells containing these polynucleotide sequences.

The invention further relates to a polynucleotide comprising:

(a) a genomic double stranded polynucleotide set forth in SEQ ID NO:3 encoding human carboxypeptidase M set forth in SEQ ID NO:1 and the polynucleotide set forth in SEQ ID NO:4 encoding human mouse double minute 2 homolog set forth in SEQ ID NO:2;

(b) a polynucleotide that hybridizes to one strand of the polynucleotide of (a) and (c) a reverse complement of (a) and (b).

as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (a) with an adjuvant and (c) obtaining antibody from said immunized host animal.

The invention is further directed to a nucleic acid molecule or reverse complement thereof comprising a sequence of nucleotides which specifically hybridizes to noncoding regions of said polynucleotide sequences of SEQ ID NO:3 (human carboxypeptidase M gene) or SEQ ID NO:4 (human mouse double minute 2 homolog gene). These sequences may be used to modulate levels of human carboxypeptidase M and human mouse double minute 2 homolog in a subject in need thereof and specifically for the manufacture of a medicament for prevention, treatment or amelioration of a medical condition. As defined herein, a "polynucleotide fragment" may be a nucleic acid molecule including DNA, RNA and analogs thereof including protein nucleic acids and mixtures thereof and may include a probe and primer. Such molecules are generally of a length such that they are statistically unique in the genome of interest. Generally, for a probe or primer to be unique in the human genome, it contains at least 14 to 16 contiguous nucleotides of a sequence complementary to or identical to a target sequence of interest. These polynucleotide fragments can be 20, 30, 50, 100, 150, 500, 600, 1000, 2000 or more nucleic acids long. Probes and primers may also be referred to as oligonucleotides. As defined herein, a "reverse complement" is a molecule encoding a sequence complementary to at least a portion of an RNA molecule or to a genomic DNA segment and may be used interchangeably with "antisense oligonucleotide". The sequence is sufficiently complementary to be able to hybridize with the RNA or DNA, preferably under moderate or high stringency conditions to form a stable duplex or triplex. A "reverse complement" also includes peptide nucleic acid reverse complement sequences.

The invention is further directed to kits comprising these polynucleotides and kits comprising these sequences. In a specific embodiment, the sequence(s) are attached to a substrate. In a specific embodiment, the support is a microarray. The microarray may contain a plurality of sequences hybridizing to non-coding sequences. As defined herein, a "plurality" of sequences is two or more sequences. Alternatively, the microarray comprises non-coding sequences as well as coding sequences.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to detect a pathological condition or susceptibility to a pathological condition in a subject comprising (a) isolating genomic DNA from said subject;

(b) detecting the presence or absence of a variant in said genomic DNA using a probe or primer derived from a polynucleotide hybridizing to non-coding region(s) of a human carboxypeptidase M gene and human mouse double minute 2 homolog gene; and (c) diagnosing a pathological condition or susceptibility to a pathological condition based on the presence or absence of said variant.

Probes or primers derived from SEQ ID NO:3 (human carboxypeptidase M gene) or SEQ ID NO: 4 (human mouse double minute 2 homolog gene) may be used to identify variants including but not limited to mutations, duplications, translocations, polysomies and mosaicism on the human carboxypeptidase M gene or on the human mouse double minute 2 homolog. Therefore, the invention is also directed to a method for identifying variants of SEQ ID NO:3 and 4 comprising (a) isolating genomic DNA from a subject and (b) determining the presence or absence of a variant in said genomic DNA using the probes or primers.

DETAILED DESCRIPTION OF THE INVENTION

The invention is directed to isolated genomic polynucleotide fragments that encode human carboxypeptidase M and human mouse double minute 2 homolog, which in a specific embodiment are the human carboxypeptidase M and human mouse double minute 2 homolog genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The genes encoding human carboxypeptidase M and the human mouse double minute 2 homolog are disposed in the chromosome 12 genomic clone of accession number AC025423, 150579 base pairs, at, respectively, nucleotides 1-99860 and 99541-150579.

The polynucleotides of the invention have at least a 95% identity and may have a 96%, 97%, 98% or 99% identity to the polynucleotides depicted in SEQ ID NOS:3 or 4 as well as the polynucleotides in reverse sense orientation, or the polynucleotide sequences encoding the human carboxypeptidase M or human mouse double minute 2 homolog polypeptides depicted in SEQ ID NOS:1 or 2 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 3 or 4. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The term "variant" also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. The term "variant" also encompasses naturally occurring variants such as single nucleotide polymorphisms (SNPs).

The amino acid sequences of the variant polypeptides may differ from the amino acid sequences depicted in SEQ ID NOS:1 or 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human carboxypeptidase M or human mouse double minute 2 homolog genes. These include but are not limited to an expression control element, an intron, a 5'-non-coding region, a 3'-non-coding region and splice junctions (see Tables 1-2, as well as transcription factor binding sites (see Table 3). The polynucleotide fragments may be a short polynucleotide fragment which is between about 20 nucleotides to about 50 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600, 2000 or about 5000 nucleotides in length may be used.

TABLE 1

EXON/INTRON ORGANIZATION OF THE HUMAN CARBOXY-PEPTIDASE M GENE (cDNA ACCESSION NO. XM_006768) IN SEQ ID NO: 3, 99680 BASE PAIRS; NUCLEOTIDES 1-99680 IN THE GENOMIC CLONE OF ACCESSION NO. AC025423 (FORWARD STRAND CODING).

| EXON | NUCLEOTIDE NO. | AMINO ACID NO. |
|---|---|---|
| 1 | 16641-16796 | 1-52 |
| 2 | 63585-63686 | 53-86 |
| 3 | 77522-77692 | 87-143 |
| 4 | 79077-79262 | 144-205 |
| 5 | 79982-80152 | 206-262 |
| 6 | 82429-82581 | 263-313 |
| 7 | 90406-90555 | 314-363 |

TABLE 1-continued

EXON/INTRON ORGANIZATION OF THE HUMAN CARBOXY-PEPTIDASE M GENE (cDNA ACCESSION NO. XM_006768) IN SEQ ID NO: 3, 99680 BASE PAIRS; NUCLEOTIDES 1-99680 IN THE GENOMIC CLONE OF ACCESSION NO. AC025423 (FORWARD STRAND CODING).

| EXON | NUCLEOTIDE NO. | AMINO ACID NO. |
|---|---|---|
| 8 | 92799-93038 | 364-443 |
| STOP CODON | 93039-93041 | |

TABLE 2

EXON/INTRON ORGANIZATION OF THE HUMAN MOUSE DOUBLE MINUTE 2 HOMOLOG GENE (VARIANT OF ACCESSION NO. NM_002392) IN SEQ ID NO: 4, 51039 BASE PAIRS; NUCLEOTIDES 99541-150579 IN THE GENOMIC CLONE OF ACCESSION NO. AC025423 (REVERSE STRAND CODING).

| EXON | NUCLEOTIDE NO. | AMINO ACID NO. |
|---|---|---|
| STOP CODON | 10089-10091 | |
| 10 | 10092-10664 | 491-301 |
| 9 | 13189-13266 | 300-275 |
| 8 | 13954-14109 | 274-223 |
| 7 | 21007-21168 | 222-169 |
| 6 | 25288-25383 | 168-137 |
| 5 | 25508-25576 | 136-114 |
| 4 | 29565-29615 | 113-97 |
| 3 | 32995-33126 | 96-53 |
| 2 | 36310-36384 | 52-28 |
| 1 | 40646-40726 | 27-1 |

TABLE 3

TRANSCRIPTION FACTOR BINDING SITES ON GENES THAT ENCODE CARBOXYPEPTIDASE M (CpM) AND THE HUMAN HOMOLOG OF MOUSE DOUBLE MINUTE 2 (huMDM2)

| BINDING SITES | CpM | huMDM2 |
|---|---|---|
| AP1FJ_Q2 | 60 | 25 |
| AP1_C | 16 | 11 |
| AP1_Q2 | 39 | 13 |
| AP1_Q4 | 24 | 12 |
| AP4_Q5 | 47 | 27 |
| AP4_Q6 | 22 | 14 |
| ARNT_01 | | 4 |
| BRN2_01 | 29 | 6 |
| CAAT_01 | 7 | 4 |
| CDPCR3HD_01 | 19 | 7 |
| CEBPB_01 | 26 | 6 |
| CMYB_01 | 7 | |
| CREL_01 | 15 | 4 |
| DELTAEF1_01 | 196 | 98 |
| FREAC7_01 | 30 | 29 |
| GATA1_02 | 40 | 25 |
| GATA1_03 | 63 | 21 |
| GATA1_04 | 109 | 46 |
| GATA1_05 | 21 | 13 |
| GATA1_06 | 33 | 26 |
| GATA2_02 | 59 | 35 |
| GATA2_03 | 20 | 19 |
| GATA3_02 | 30 | 23 |
| GATA3_03 | 18 | 20 |
| GATA_C | 61 | 15 |
| GFII_01 | 23 | 8 |
| HFH2_01 | 20 | 13 |
| HFH3_01 | 32 | 13 |
| HFH8_01 | 23 | 7 |
| HNF3B_01 | 10 | 7 |
| IK1_01 | 12 | |
| IK2_01 | 216 | 63 |

TABLE 3-continued

TRANSCRIPTION FACTOR BINDING SITES ON GENES
THAT ENCODE CARBOXYPEPTIDASE M (CpM) AND
THE HUMAN HOMOLOG OF MOUSE DOUBLE
MINUTE 2 (huMDM2)

| BINDING SITES | CpM | huMDM2 |
|---|---|---|
| LMO2COM_01 | 86 | 23 |
| LMO2COM_02 | 85 | 23 |
| LYF1_01 | 45 | 41 |
| MAX_01 | 8 | 4 |
| MYCMAX_02 | 8 | |
| MYOD_01 | 5 | |
| MYOD_Q6 | 49 | 21 |
| MZF1_01 | 187 | 61 |
| NF1_Q6 | 10 | 5 |
| NFAT_Q6 | 134 | 71 |
| NFY_Q6 | 16 | |
| NKX25_01 | 48 | 35 |
| NKX25_02 | 30 | 9 |
| NMYC_01 | 16 | 10 |
| OCT1_01 | 3 | |
| OCT1_02 | 6 | |
| OCT1_06 | 3 | |
| OCT1_07 | 5 | |
| OCT1_Q6 | 5 | |
| RORA1_01 | 8 | 9 |
| S8_01 | 183 | 128 |
| SOX5_01 | 76 | 29 |
| SRY_02 | 38 | 27 |
| STAT_01 | 11 | |
| TATA_01 | 28 | 22 |
| TATA_C | 20 | 8 |
| TCF11_01 | 182 | 51 |
| USF_01 | 16 | 10 |
| USF_C | 16 | 10 |
| VMYB_02 | 7 | 11 |
| XFD2_01 | 11 | 8 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 12 genomic clone of accession number AC025423 has been discovered to contain the human carboxypeptidase M gene and the human mouse double minute 2 homolog gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC025423 was compared to the human carboxypeptidase M cDNA sequence, accession number XM_006768 and the human mouse double minute 2 homolog cDNA sequence accession number NM_002392, one of several splice variants.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human carboxypeptidase M gene or the human mouse double minute 2 homolog gene may be accomplished in a number of ways. For example, if an amount of a portion of a human carboxypeptidase M gene or the human mouse double minute 2 homolog gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 15 and preferably 40, nucleotide fragment of the sequences depicted in SEQ ID NOS:3 or 4. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous human carboxypeptidase M or human mouse double minute 2 homolog polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:3 or 4 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human carboxypeptidase M or human mouse double minute 2 homolog polypeptide.

A gene encoding human carboxypeptidase M or human mouse double minute 2 homolog polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments that contain the desired sequences.

Nucleic Acid Constructs

The present invention also relates to nucleic acid constructs comprising a polynucleotide sequence containing the exon/intron segments of the human carboxypeptidase M gene (nucleotides 1-99680 of SEQ ID NO:3) or human mouse double minute 2 homolog gene (nucleotides 1-51039 of SEQ ID NO:4) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 3 or 4 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (VIIIa-Komaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention. Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Preferred terminators for yeast host cells are obtained from the genes encoding *Saccharomyces cerevisiae* enolase, *Saccharomyces cerevisiae* cytochrome C(CYC1), or *Saccharomyces* cerevisiae glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention. Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention. Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase. Useful polyadenylation sequences for yeast host cells are described by Guo and Sherman, 1995, *Molecular Cellular Biology* 15: 5983-5990. The control sequence may also be a signal peptide coding region, which codes for an amino acid sequence linked to the amino terminus of the polypeptide which can direct the encoded polypeptide into the cell's secretory pathway.

The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention. An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109-137. An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene. Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, METS, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-56-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell. For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM§1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, 293, H9 and Jurkat cells, mouse NIH3t3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, carboxypeptidase M activity can be determined by measuring the release of the C-terminal arginine of bradykinin or a synthetic acyl-dipeptide such as benzoyl-Ala-Arg. The human homolog of mouse double minute 2 may be detected by its ability to bind p53.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the human carboxypeptidase M or human mouse double minute 2 homolog polypeptides produced according to the method of the present invention may be used as an immunogen to generate any of these antibodies. Such antibodies include but are not limited to polyclonal, monoclonal, chimeric, single chain, Fab fragments, and a Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the human carboxypeptidase M or human mouse double minute 2 homolog polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the human carboxypeptidase M or human mouse double minute 2 homolog polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the human carboxypeptidase M or human mouse double minute 2 homolog polypeptide.

Antibody fragments that contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab)$_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Substrate

In a specific embodiment, the polynucleotides of the present invention, particularly, the polynucleotide fragments for hybridizing to non-coding regions of SEQ ID NOS:3 or 4 may be attached to a substrate or reverse complements of said fragments. A substrate may be solid or porous, planar or non-planar, unitary or distributed. The polynucleotide may be attached covalently or applied to a derivatized surface in a chaotropic agent that facilitates denaturation and adherence by presumed noncovalent interactions, or some combinations thereof.

In a more specific embodiment, the substrate is a microarray. "Microarray" as defined herein is a substrate-bound collection of a plurality nucleic acids, hybridization to each of the plurality of bound nucleic acids being separately detectable. The microarray may comprise a plurality of polynucleotides hybridizing to a non coding region of SEQ ID NO:3 or 4. Alternatively the microarray may comprise a polynucleotide(s) hybridizing to said non-coding region and/or coding regions of SEQ ID NO:3 or 4.

Uses of Polynucleotides

Diagnostics

Polynucleotide fragments containing noncoding regions of SEQ ID NO:3 or 4 may be used as probes for detecting variants from genomic nucleotide samples from a patient. The variants may be allelic variants or substitution, insertion or deletion nucleotide variants. Genomic DNA may be isolated from the patient. Alternatively the polynucleotide fragments may be used to monitor expression of SEQ ID NO:3 or 4 from samples from a patient. A mutation(s) may be detected by Southern blot analysis, for example, by hybridizing restriction digested genomic DNA to various probes between 10-500 nucleotides in length, preferably between 20-200 nucleotides in length, more preferably between 20-100 nucleotides in length and most preferably between 20-50 nucleotides in length and subjecting to agarose electrophoresis. Alternatively, these polynucleotides may be used as PCR primers between about 10-100 nucleotides in length and be used to amplify the genomic DNA isolated from the patients. Methods for performing primer-directed amplification (routine or long range PCR) are well known in the art (see, for example, PCR Basics: From Background to Bench, Springer Verlag (2000); Gelfand et al., (eds.), PCR Strategies, Academic Press (1998)). Single base extension (see, for example, U.S. Pat. No. 6,004,744) may be used to detect SNPs. Additionally, primers may be obtained by routine or long range PCR that yield products containing contiguous intron(s)/exon sequence(s) and products containing more than one exon with intervening intron(s). The sequence of the amplified genomic DNA from the patient may be determined using methods known in the art. Such probes may be between 20-5000 nucleotides in length and may preferably be between 20-50 nucleotides in length.

Thus the invention is directed to kits comprising these polynucleotide probes. In a specific embodiment, these probes are labeled with a detectable substance.

In one embodiment, the probes are in solution. In another embodiment, the probes are attached to a substrate. In a specific embodiment, the probes are contained within a microarray and are separately detectable. The probes or primers of the present invention could be used to identify patients with or having a propensity for sepsis (SEQ ID NO:3-carboxypeptidase M gene) or for sarcoma or leukemias (SEQ ID NO:4-human mouse double minute 2 homolog gene).

Antisense Oligonucleotides and Mimetics

The antisense or reverse complement oligonucleotides or mimetics of the present invention may be used to decrease levels of a polypeptide. For example, human carboxypeptidase M has been found to form des-Arg9-bradykinin, an agonist of the B1 receptor activated by sepsis. Therefore, the human carboxypeptidase M antisense oligonucleotides of the present invention could be used to inhibit formation of des-Arg9-bradykinin. Human mouse double minute 2 homolog antisense sequences may be used to treat sarcomas and leukemias in which the gene is over-expressed.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human carboxypeptidase M modulates actions of anaphylatoxins and kinins and human mouse double minute 2 homolog plays a role in cell proliferation. Therefore, the human carboxypeptidase M gene may be used to modulate or prevent complement-linked tissue damage, in subjects in need thereof, for example, those exhibiting allergic reactions to a given substance. The human mouse double minute 2 homolog gene may be used to stimulate cell proliferation in subjects in need thereof, for example, for wound healing and those suffering from neurodegenerative or neuromuscular diseases, ischemic stroke, anoxia, ischemia/reperfusion damage and intoxication septic shock.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes: a) Biological agents derived from viral, bacterial or other sources and b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous polyA addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN™ and LIPOFECTACE™, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Feigner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4_spermidine cholestryl carbamate (GL-53) and 1-(N-4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class 1 molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for modulating levels of human mouse double minute 2 homolog activity in a subject in need thereof comprising administering to said subject an amount of an isolated genomic nucleic acid molecule, said nucleic acid molecule selected from the group consisting of:
(a) a nucleic acid molecule consisting of a nucleic acid sequence which has at least 99% identity to the nucleic acid molecule of SEQ ID NO:4 that encodes a polypeptide that has human mouse double minute 2 homolog activity and
(b) a fragment of the nucleic acid molecule of (a), said fragment comprising at least nucleotides 41738-9502 of SEQ ID NO:4 and which encodes a polypeptide having human mouse double minute 2 homolog activity effective to modulate said human mouse double minute 2 homolog levels.

2. A method for modulating levels of human mouse double minute 2 homolog activity in a subject in need thereof comprising administering to said subject an amount of an isolated nucleic acid molecule 20-51039 contiguous nucleotides in length consisting of a reverse or forward strand of a region of SEQ ID NO:4, wherein said region is selected from the group consisting of a 5'-non coding region between nucleotides 51039-41739 of SEQ ID NO:4; a 3'-non-coding region between nucleotides 9503-1 of SEQ ID NO:4; a contiguous intron-exon region between nucleotides 41738-9502 of SEQ ID NO:4, wherein a sequence segment between nucleotides 41738-9502 of SEQ ID NO:4 encodes human mouse double minute 2 homolog depicted in SEQ ID NO:2; a contiguous exon-intron region between nucleotides 41738-9502 of SEQ ID NO:4, wherein a sequence segment between nucleotides 41738-9502 of SEQ ID NO:4 encodes human mouse double minute 2 homolog depicted in SEQ ID NO:2; an intron depicted in nucleotides 36385-40645, 36309-33127, 32994-29616, 29564-25577, 25507-25384, 25287-21169, 21006-14110, 13953-13267, and/or 13188-10665; a region comprising a dinucleotide of the following group: 41739-41738, 40645-40646, 36309-36310, 36384-36385, 32994-32995, 33126-33127, 29564-29565, 29615-29616, 25507-25508, 25287-25288, 25383-25384, 25576-25577, 21006-21007, 21168-21169, 14109-14110, 13953-13954, 13266-13267, 13188-13189, 10664-10665 and/or 9504-9503; a transcription binding site selected from the group consisting of

| BINDING SITES | huMDM2, location in SEQ ID NO: 4 |
|---|---|
| AP1_C: | 36-46, 2876-2886; |
| AP4_Q5: | 7944-7980; |
| AP4_Q6: | 7943-59, 8924-8940, 9294-9310; |
| ARNT_01: | 1682-1706, 2193-2217, 9201-9225; |
| BRN2_01: | 1040-1058, 7803-7821; |
| CAAT_01: | 3292-3306; |
| CDPCR3HD_01: | 6522-6540; |
| CEBPB_01: | 1424-1438, 3917-3931, 4178-4192, 4787-4801, 6855-6869; |
| CREL_01: | 5630-5642; |
| DELTAEF1_01: | 83-95, 6328-6340; |
| FREAC7_01: | 2757-2773, 5154-5170, 5823-5839; |
| GATA1_04: | 4846-4858, 7017-7029; |
| GATA1_05: | 8464-8476; |
| GATA2_02: | 6045-6057, 6073-6085, 6142-6154; |
| GATA2_03: | 2489-2501, 3323-3335, 3384-3396, 7393-7405: |
| GATA3_02: | 3264-3276, 6870-6882: |
| GATA3_03: | 40-52, 5729-5741, 6529-6541, 6874-6886, 7041-7053, 7589-7601; |
| GATA_C: 7 | 349-7361, 8188-8200; |
| HFH2_01: | 1743-1759, 7995-8011; |
| HFH3_01: | 502-518, 1739-1755, 4160-4176, 9402-9418, 9418-9434; |
| HFH8_01: | 8184-8200; |
| IK2_01: | 951-963, 3588-3600; |
| MZF1_01: | 1202-1210, 1447-1455, 4997-4005, 5424-5432; |

-continued

| BINDING SITES | huMDM2, location in SEQ ID NO: 4 |
|---|---|
| NF1_Q6: | 1480-1500, 8166-8182; |
| NFAT_Q6: | 4190-4208, 6009-6027; |
| NKX25_01: | 741-755, 1648-1662, 1885-1899, 1984-1998, 3609-3623, 4928-4942, 5060-5074, 5889-5903, 8850-8864, 9190-9204; |
| NKX25_02: | 2584-2599, 2970-2984, 4644-4658, 5179-5193, 6482-6496; |
| NMYC_01: | 2560-2572; |
| RORA1_01: | 220-238, 2638-2656; |
| S8_01: | 4644-4656, 4842-4854, 4845-4857, 5200-5212, 5371-5383, 5735-5747, 6482-6494, 6541-6553, 6544-6556, 6772-6784, 7270-7292, 7273-7285; |
| SOX5_01: | 1355-1371, 1430-1446, 3094-3110, 3155-3171, 4669-4685, 4692-4708, 4789-4805; |
| SRY_02: | 4164-4180, 5665-5681; |
| TATA_01: | 1261-1277, 2574-2590, 2723-2739, 2733-2749, 2770-2786, 4199-4215, 4206-4222; |
| TATA_C: | 5900-5916, 7456-7472, 7702-7718, 7917-7933; and |
| XFD2_01: | 7702-7218, 7917-7933; | a transcription binding site selected from the group consisting of

| BINDING SITES | huMDM2, location in SEQ ID NO: 4 |
|---|---|
| AP1_C: | 12109-12119, 12695-12705, 22600-22610, 24166-24176, 31311-31321, 35234-35244, 39184-39194; |
| AP1_Q2: | 11952-11962, 12068-12078, 14798-14808, 21748-21758, 22613-22623, 23676-23686, 26562-26572, 30046-30056; |
| AP1_Q4: | 12695-12705, 31311-31321, 35234-35244, 36295-36305, 38784-38794, 39188-39198; |
| AP4_Q6: | 31635-31651; |
| BRN2_01: | 13448-13466, 14764-14782, 28094-28112, 40027-40045; |
| CAAT_01: | 11288-11302, 15054-15068; |
| CDPCR3HD_01: | 11286-11304, 13284-13302, 20846-20864, 29344-29362; |
| CEBPB_01: | 29241-29255; |
| CREL_01: | 36091-36103, 38873-38885; |
| DELTAEF1_01: | 18083-18095, 20385-20397, 26955-26967; |
| FREAC7_01: | 11982-11998, 15187-15202, 16523-16539, 16529-16545, 16587-16603, 16604-16620, 16676-16642, 16633-16649, 16644-16660, 16650-16666, 16657-16673, 16673-16689, 16762-16778, 21332-21348, 25689-25700, 26529-26545, 27767-27783, 29495-29511; |
| GATA1_02: | 10916-10928, 15775-15789, 18162-18174, 26088-26100, 32518-32530; |
| GATA1_03: | 28012-28024; |
| GATA1_04: | 11153-11165, 11630-11642, 13778-13790, 17439-17451, 19300-19312, 21606-21618, 22743-22755, 23747-23759, 25806-25818, 26529-26541, 29424-29436, 30455-30467, 32761-32778, 33352-33364, 33960-33972, 36101-36113, 40007-40019; |
| GATA1_05: | 11590-11602, 26550-26562, 36737-36749; |
| GATA1_06: | 18772-18784, 23054-23066, 35568-35580, 37855-37867; |
| GATA2_02: | 20755-20767, 30830-30842, 34755-34767, 36285-36297, 39143-39155, 39641-39653, 40586-40598; |
| GATA2_03: | 13535-13547, 22711-22723, 23161-23173, 25028-25040, 27237-27249, 36277-36289; |
| GATA3_02: | 11558-11570, 16470-16482, 17225-17237, 19619-19631, 22156-22168, 22443-22455, 24713-24725, 27619-27631, 32716-32728, 34124-34136, 34163-34175, 36832-36844, 38403-38415; |
| GATA3_03: | 10869-10881, 11515-11527, 13845-13857, 17221-17233, 18952-18964, 20050-20062, 40171-40183; |
| GATA_C: | 15848-15860, 18899-18911, 23640-23652, 29072-29084, 30881-30893, 33198-33210, 37472-37484, 38621-38633; |
| GFI1_01: | 35469-35481, 35492-35504; |
| HFH2_01: | 15939-15955, 24636-24652, 25866-25882, 32171-32187, 35372-35388, 39457-35473; |
| HFH3_01: | 13340-13356, 19218-19234, 21328-21344, 21336-21352, 21344-21360, 28062-28078, 32125-32141; |
| HFH8_01: | 14133-14149, 22578-22584; |
| HNF3B_01: | 13150-13166, 16505-16521, 25264-25280, 29443-29459, 37654-37670; |
| IK2_01: | 11547-11559, 17144-17156, 18961-18973, 23883-23895, 27617-27629, 28908-28920, 29241-29253, 30752-30764, 34768-34780; |
| LYF1_01: | 12319-12331, 19191-19203, 37226-37238, 39430-39442; |
| MAX_01: | 22974-22986, 33339-33351; |
| MZF1_01: | 26105-26113, 35187-35195; |
| NF1_Q6: | 12048-12064, 33334-33354; |
| NFAT_Q6: | 13295-13313, 14157-14175, 14311-14329, 14414-14432, 18269-18287. 19326-19344, 20801-20819, 21177-21195, 22537-22555, 23861-23879, 25392-25410, 25879-25897, 27524-27542, 30636-30654, 30718-30736, 31525-31543, 33655-33673, 34726-34744, 34917-34535, 34990-35008, 35979-35997, 36479-36493, 36577-36595, 37154-37172, 40224-40242, 40365-40383; |

| BINDING SITES | huMDM2, location in SEQ ID NO: 4 |
|---|---|
| NKX25_01: | 12041-12055, 12340-12354, 12471-12485, 12742-12756, 12877-12891, 13849-13863, 18995-19009, 21440-21454, 21883-21897, 28426-28440, 30964-30978, 32033-32047, 32265-32279; |
| NKX25_02: | 10998-11012, 12711-12725, 14131-14145, 14726-14740, 16024-16038; |
| NMYC_01: | 18753-18765, 18754-18766, 23076-23088, 30534-30546, 34400-34412; |
| RORA1_01: | 13134-13152, 22966-22984, 24934-24952, 33341-33359, 34760-34778; |
| S8_01: | 11000-11012, 11977-11989, 12048-12060, 12051-12063, 13747-13759, 13923-13935, 13926-13938, 14676-14688, 14679-14691, 16026-16038, 16313-16325, 16316-16328, 17515-17527, 20756-20768, 20759-20771, 23154-23166, 23157-23169, 25198-25210, 25201-25213, 26651-26663, 27508-27520, 27511-27523, 29450-29462, 29478-28490, 29775-29787, 29778-29790, 29813-29825, 29816-29828, 31329-31341, 31677-31689, 31680-31692, 31732-31744, 31735-31747, 36137-36149, 36140-36152, 36812-36824, 36815-36827, 37413-37425, 38679-38691, 39474-39486, 39477-39489; |
| SOX5_01: | 27397-27413, 27572-27588, 28100-28116, 29230-29246, 29439-29455, 30690-30706, 31595-31611, 33871-33887, 34113-34129, 34624-34640, 37668-37684, 38582-38598, 39124-39140, 40410-40426; |
| SRY_02: | 20016-20032, 22410-22426, 27329-27345, 29162-29178, 29499-29515, 30646-30662, 31503-31519, 35928-35944, 37324-37340; |
| TATA_01: | 32722-32738, 32729-32745, 32807-32823, 33825-33841, 34120-34136, 35433-35449, 36593-36609; |
| TATA_C: | 11015-11031, 11817-11833, 13635-13651, 14930-14946; |
| TCF11_01: | 18543-18549, 22574-22580, 31281-31297, 31489-31505, 38754-38770; |
| USF_01: | 23075-23087, 32577-32589; |
| VMYB_02: | 11526-11538, 17384-17396, 18400-18412, 19549-19561, 22188-22200, 40486-40508 and |
| XFD2_01: | 16620-16636. 18153-18169, 22102-22118, 23141-23157. |

And a transcription binding site selected from the group consisting of

| BINDING SITES huMDM2, 1 | location in SEQ ID NO: 4 |
|---|---|
| AP1_C: | 44584-44594, 49069-49079: |
| AP1_Q2: | 42174-42184, 45217-45227, 48422-48422, 50447-50457; |
| AP1_Q4: | 42702-42712, 50806-50816; |
| AP4_Q6: | 42117-42133, 42118-42134, 42244-42260, 45432-45448; 45433-45449, 46609-46625; |
| BRN2_01: | 42310-42328, 44022-44040, 47514-47532, 48900-48918, 48967-48985; |
| CAAT_01: | 44866-44880; |
| CDPCR3HD_01: | 45671-45689, 49219-49237; |
| CREL_01: | 42437-42449, 49797-49809; |
| FREAC7_01: | 47026-47042, 47292-47308, 47658-47674; |
| GATA1_02: | 43482-43494, 48926-48938, 49284-49296; |
| GATA1_03: | 47371-47383; |
| GATA1_04: | 43054-43066, 43162-43162, 43967-43979, 45464-45476, 45916-45928, 47763-47775; |
| GATA1_05: | 49319-49331, 49459-49471; |
| GATA1_06: | 47590-47602; |
| GATA2_02: | 42660-42672, 43475-43487; |
| GATA2_03: | 43714-43726, 50948-50960; |
| GATA3_02: | 49155-49167, 49844-49856; |
| GATA3_03: | 42202-42214, 44810-44822, 48438-48450, 49136-49148, 49337-49349, 49869-49881; |
| GATA_C: | 44011-44023, 45256-45268, 45823-45835, 47915-47927, 49201-49213, 49573-49585; |
| GFI1_01: | 46606-46618, 47063-47075; |
| HFH3_01: | 47030-47046, 47284-47300, 47288-47304; |
| IK2_01: | 45275-45287; |
| LYF1_01: | 44564-44576, 46991-47003, 49567-49579; |
| MAX_01: | 43234-43246, 48726-48738; |
| MZF1_01: | 41772-41780, 42290-42298, 42295-42303, 44507-44515, 45105-45113, 45203-45211, 49948-49956, 50774-50782; |
| NF1_Q6: | 50209-50229; |
| NFAT_Q6: | 42061-42079, 44418-44436, 46399-46417, 47974-47992, 49267-49285, 49964-49982, 50392-50410; |
| NKX25-01: | 42394-42408, 43507-43521, 46115-46129; |
| RORA1_01: | 45073-45091, 48718-48736; |
| S8_01: | 43552-43564, 45214-45226, 47160-47172, 48419-48431, 49295-49307, 50379-50391; |
| SOX5_01: | 43716-43732, 46351-46367, 47156-47172, 47774-47790, 47868-47884, 47974-47990, 48915-48931, 50323-50339; |
| TATA_01: | 45588-45604, 47625-47641, 48026-48042, 48659-48675, 49056-49072, 49079-49095, 49152-49168; |

-continued

| BINDING SITES huMDM2, 1 | location in SEQ ID NO: 4 |
|---|---|
| TCF11_01: | 49115-49131; |
| VMYB_02: | 42010-42022, 42279-42291, 44651-44663; and |
| XFD2_01: | 42870-42886, 42910-42926. |

\* \* \* \* \*